(12) United States Patent
Reindel

(10) Patent No.: US 7,531,003 B2
(45) Date of Patent: May 12, 2009

(54) WRIST IMPLANT APPARATUS AND METHOD

(75) Inventor: Eric S. Reindel, Encinitas, CA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 345 days.

(21) Appl. No.: 10/666,680

(22) Filed: Sep. 18, 2003

(65) Prior Publication Data

US 2004/0117025 A1 Jun. 17, 2004

Related U.S. Application Data

(60) Provisional application No. 60/411,824, filed on Sep. 18, 2002.

(51) Int. Cl.
*A61F 2/42* (2006.01)
(52) U.S. Cl. .................................. 623/21.12
(58) Field of Classification Search ............... 623/21.12
See application file for complete search history.

(56) References Cited

U.S. PATENT DOCUMENTS

| 5,314,485 | A | 5/1994 | Judet |
| 5,702,470 | A | 12/1997 | Menon |
| 6,168,630 | B1 | 1/2001 | Keller et al. |
| 2003/0216813 | A1 * | 11/2003 | Ball et al. ................ 623/21.12 |

OTHER PUBLICATIONS

European Search Report for PCT/US0329828 dated Jun. 2, 2006.

International Preliminary Report for PCT/US03/29828 dated Jan. 3, 2007.
European Patent Office Office Action Dated Oct. 26, 2007 for European Patent Application No. 03759390.2-2310.
Communication under Rule 71(3) EPC dated Jun. 18, 2008 for European Patent Application No. 03759390.2-2310.

\* cited by examiner

*Primary Examiner*—David Isabella
*Assistant Examiner*—Jonathan R Stroud
(74) *Attorney, Agent, or Firm*—Jenkins, Wilson, Taylor & Hunt, P.A.

(57) ABSTRACT

Prosthetic wrist implants and methods are provided. The prosthetic wrist implant includes a radial component including a base member having an upper bearing surface and a lower surface having an elongated radial stem for fixation to a radius bone. The elongated radial stem can be in an off-center position in relation to a center of the lower surface. A carpal component is also provided including a substantially planar base member having an upper surface and a lower surface with at least one socket protrusion extending therefrom, and may further included an elongated carpal post member for fixation to one or more carpal bones. An articulating bearing component for placement between the radial and carpal components is provided and includes an upper surface defining at least one socket recess and a lower bearing surface for cooperative engagement with the upper bearing surface of the radial component. The socket protrusion of the carpal component is adapted to linearly engage the socket recess of the bearing component to desirably limit rotational and translational movement of the carpal component relative to the bearing component.

32 Claims, 50 Drawing Sheets

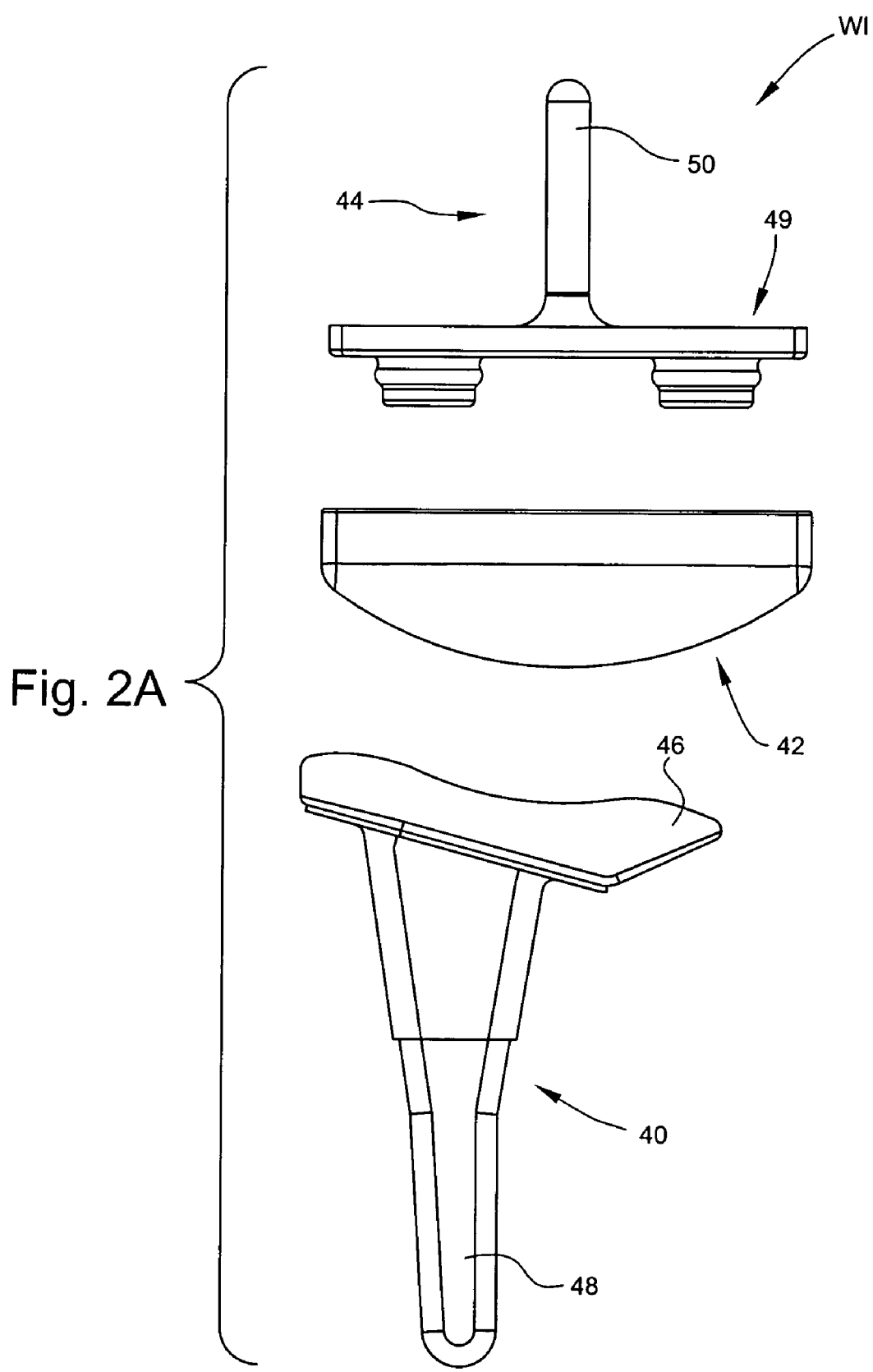

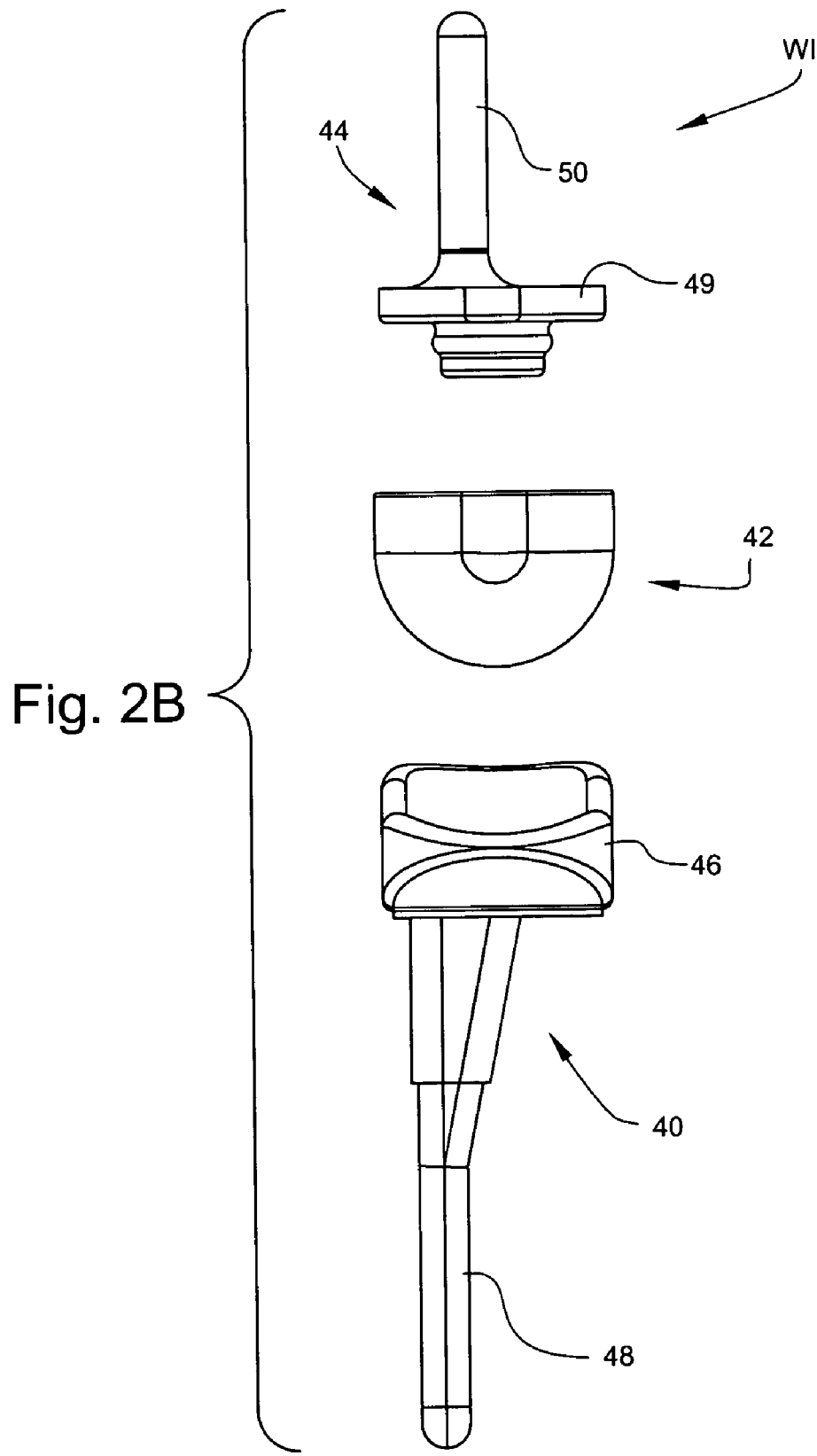

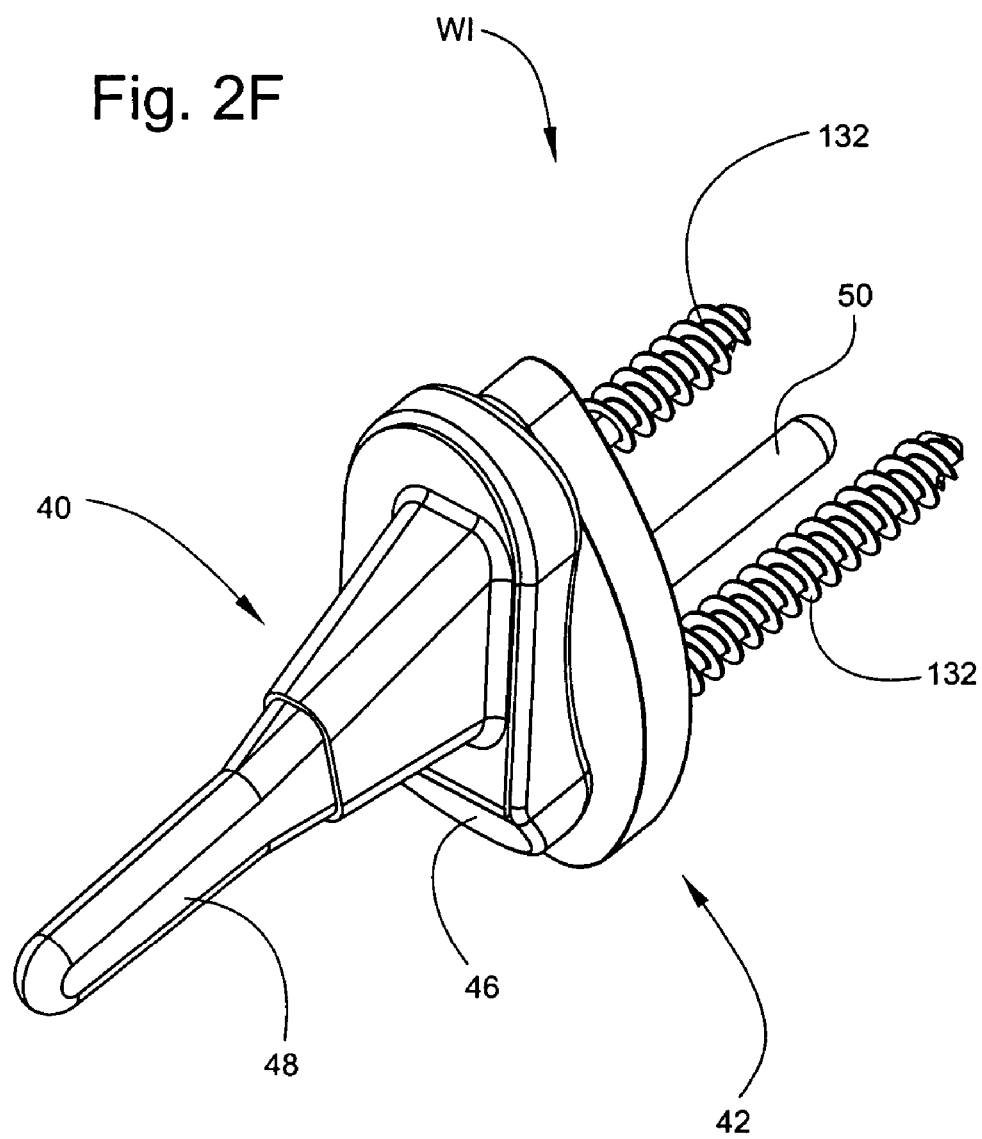

EXTRA-SMALL

SMALL

MEDIUM

LARGE

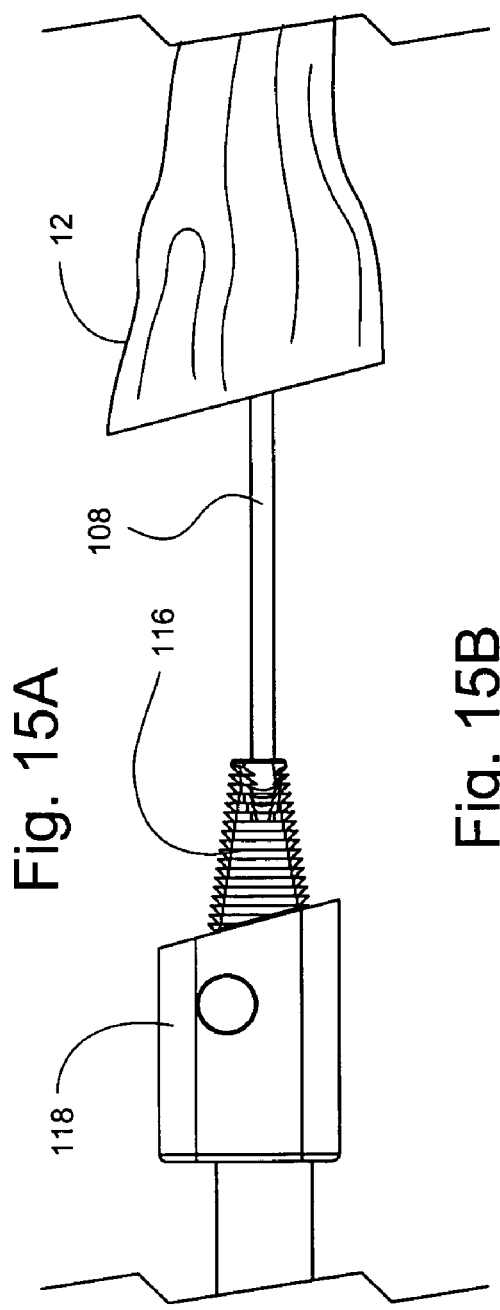
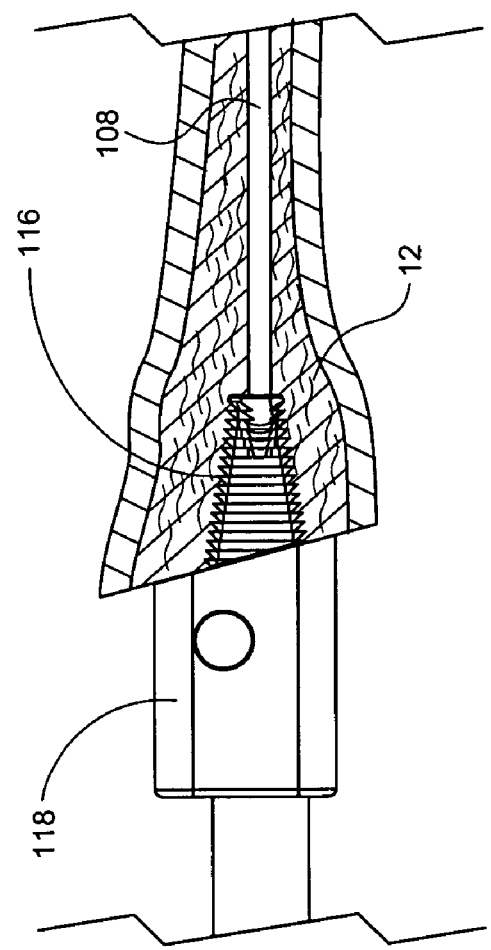

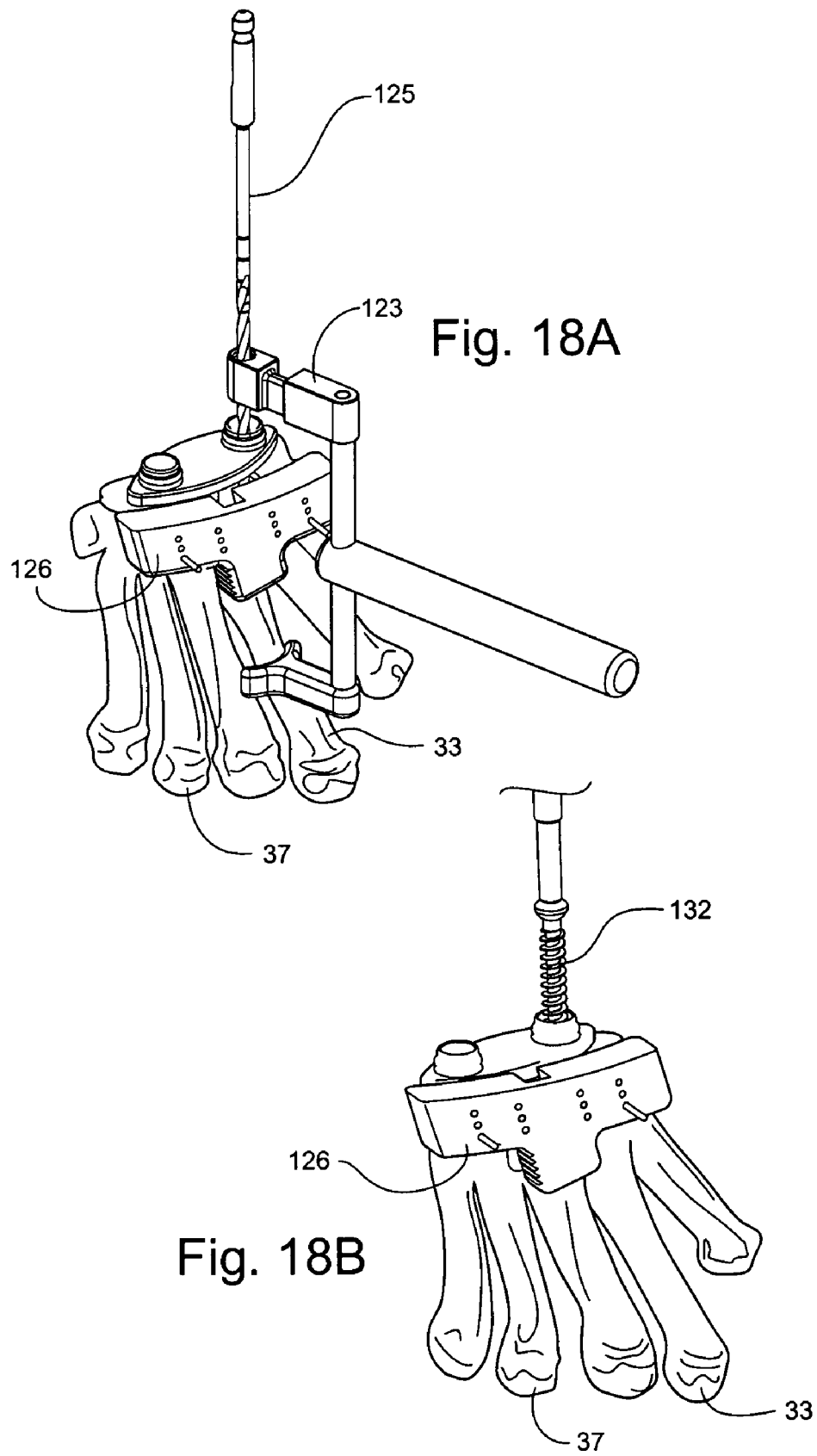

7,531,003 B2

WRIST IMPLANT APPARATUS AND METHOD

RELATED APPLICATIONS

This application claims the benefit of U.S. Provisional Patent Application Ser. No. 60/411,824, filed Sep. 18, 2002; the disclosure of which is incorporated herein by reference in its entirety.

TECHNICAL FIELD

The present subject matter relates to prosthetic implants and more particularly to wrist implant apparatuses and methods utilizing a wrist implant with a geometry that closely matches that of the natural wrist, which minimizes bone resection, and which can be installed in a manner to minimize future implant failure.

BACKGROUND ART

The replacement of degenerated natural joints with man-made prosthetic replacements is well known, including the replacement of the wrist joint. Prior to the introduction of prosthetic joint replacement, patients with wrist diseases such as radio-carpal arthritis were often treated with a fusion procedure. Fusion typically involved an implantable joint replacement that prevented articulation of the wrist. Fusion however, proved to be less than satisfactory since it left the patient with no movement in the wrist.

Existing prosthetic wrist implants have a number of drawbacks. Because of the size needed to achieve the necessary strength, wrist implants have typically required excessive amounts of bone to be resected. For example, in these implants relatively large and lengthy implant stems were inserted into the radius and carpal bones. This significantly weakened the bones making them more susceptible to post-operative fracture. Furthermore, once fracture occurs, because of the significant loss of bone due to resection, there may not be enough bone left to permit a satisfactory fusion procedure. This may leave a patient without any avenue of treatment, not even fusion.

Another drawback with prior prosthetic wrist implants is that they do not provide the patient with acceptable functionality. Part of the problem is that these implants have not adequately matched the geometry of the natural wrist. As a result, flexion and extension of the hand return to a natural position, and range of motion have all been less than optimum, and the patient is left with less functionality of the implanted wrists than with a natural wrist.

Another difficulty with prior wrist implants involves the means of attaching the implant to the radius and carpal bones. If the attachment is not secure enough, or the implant itself is not strong enough, the stability of the attachment may not be adequate under normal use of the wrist. Because of this, larger implants and implant stems have been used to attach the implant components into the bone. However, as discussed above, this results in more resection and weakening of the bone. As a result of the above issues, existing prosthetic wrist implants have not always achieved adequate levels of patient satisfaction and have sometimes resulted in unacceptable complication rates.

Another problem with wrist implant procedures is the unavailability of special instruments for performing the implant operations. Tools currently available make excavation of a hole, which is cut into the bone to position the implant, difficult and imprecise. As a result, malrotation of the tool can occur which results in misalignment of the implant. Further, specialty guides are unavailable to assist in alignment of a cutting blade during resection of the bone into which the implant is to be fitted. The absence of a guide during the actual resection requires the surgeon performing the resection to "eyeball" the area to be resected. This may result in excess bone material being removed during the resection.

A final problem with prior art wrist implants is the manner in which the implant is pieced together and functions, and the potential to limit the life of the implant due to particle contamination. U.S. Pat. Nos. 5,702,470 and 6,059,832 each describe a prosthetic wrist implant comprising a prosthetic wrist implant disposed between a patient's radius and carpal complex bones. The implant includes a radial implant component, a carpal bone implant component, and an articulating bearing member that is fastened to the carpal bone implant and slidingly engages the radial implant. While these prior art devices may work for their intended purposes, two primary areas could be improved. First, the articulating bearing member of these prior art patents is designed to connect laterally (sideways from the dorsal plane) onto the carpal bone implant component through the use of slots on the bearing member that connect with tabs on the carpal implant. This joining action requires the surgeon to use a large, cumbersome tool to grasp both the bearing member and the carpal implant and slide them together laterally for a tight fit. Second, once the bearing member and carpal implant are joined, the metal surface of the carpal implant is exposed underneath the bearing member. At extreme flexions of the wrist, the metal radial implant can rub against the metal exposed portion of the carpal implant, causing the shedding of metallic particulate matter. This metal particulate matter can contaminate surrounding tissue and lead to cell degeneration and death. Once surrounding tissue is damaged, the implant is loosened and eventually this loosening can lead to implant failure.

Thus, it would be desirable to provide improved prosthetic wrist implants, and methods that overcome some or all of the above-discussed problems. In particular it would be desirable to provide wrist implants with a geometry which matches that of a natural wrist and which affords the patient a natural range of motion, natural flexion and natural extension of the hand. Furthermore, it would be desirable to provide prosthetic wrist implants that are small enough to minimize the bone resection required. It further would be desirable to provide wrist implants that function in a manner so as to minimize effort required to join functioning components of the implants and to also minimize the chances of metal-on-metal contact of implant components and subsequent implant failure. It would also be desirable to provide an improved methods for attaching prosthetic wrist implants which provide a stable and strong attachment to the bone without requiring excessive loss of bone through resection or drilling.

SUMMARY

The prosthetic wrist implants and methods disclosed herein combine a number of positive design features to provide optimal range of motion with acceptable flexion and extension of the hand. This is accomplished by incorporating an implant with a unique geometry matching that of the natural wrist. For example, an inclined articular surface of a radial component of the implant mimics the articular surface of a radius. In addition, a carpal component and bearing component of the wrist implant are designed to linearly engage with the use of simple tools so that the bearing component completely covers certain exposed portions of the carpal component, eliminating metal-on-metal contact between the radial component and the carpal component and minimizing future implant failure. The wrist implant empowers the surgeon the option to select the best method of implant fixation for the patient by utilizing either bone cement for cement fixation or implant interference fit for press-fit fixation. The carpal plate is primarily secured to the carpus bones by way of screws with the addition of either bone cement of press-fit fixation methods. The radial implant is secured to the distal radius bone by either bone cement of press-fit fixation methods. This, coupled with a range of implant sizes, from extra-small to large, allows the surgeon to determine and select the optimal fit with minimal bone resection. These aspects result in a stronger attachment as well as stronger bone structure post-operatively.

In accordance with one embodiment of the presently disclosed subject matter, a prosthetic wrist implant comprises a radial component including a base member having an upper bearing surface and a lower surface having an elongated radial stem for fixation to a radius bone. The elongated radial stem can be in an off-center position in relation to the centerline of the lower surface. The wrist implant also includes a carpal component including a substantially planar base member having an upper surface having an elongated carpal post member for fixation to one or more carpal bones and a lower surface with at least one socket protrusion extending therefrom. Additionally, the wrist implant includes an articulating bearing component for placement between the radial and carpal components, the bearing component having an upper surface defining at least one socket recess and a lower bearing surface for cooperative engagement with the upper bearing surface of the radial component. In the preferred embodiment, the socket protrusion of the carpal component is adapted to linearly engage the socket recess of the bearing component to desirably limit rotational and translational movement of the carpal component relative to the bearing component.

A method for implanting a prosthetic wrist implant in a wrist area is also provided comprising surgically opening a patient's wrist area and exposing a radius bone and carpal bone complex bones, resectioning the radius bone, broaching the radius bone, selecting a radial component and positioning the selected radial component within the radius bone broach and adjacent to the radius bone so that the lower surface of the radial component abuts the resected radius bone. The method also includes resectioning the carpal bone complex, selecting a carpal component and positioning the selected carpal component adjacent to the carpal bone complex so that the upper surface of the carpal component abuts the resected carpal bone complex. Once the radial and carpal components have been secured to the radius bone and carpal bone, respectively, the method includes selecting an articulating bearing component and linearly engaging the bearing component with the carpal component to desirably limit rotational and translational movement of the carpal component relative to the bearing component. Finally, the wrist area can then be surgically closed.

Accordingly, it is an object to provide improved prosthetic wrist implants and methods designed to minimize effort required to join functioning components and to also minimize wear and dislocation on implant components that can result in implant failure.

An object having been stated hereinabove, and which is addressed in whole or in part by the present subject matter, other objects will become evident as the description proceeds when taken in connection with the accompanying drawings as best described hereinbelow.

BRIEF DESCRIPTION OF THE DRAWINGS

FIGS. 2A-2G are side elevation, front elevation, and perspective views of the components of an embodiment of the wrist implant apparatus;

FIGS. 15A and 15B are perspective views showing radius broaching;

FIGS. 18A and 18B are perspective views showing trial carpal implant component installation;

DETAILED DESCRIPTION

The present subject matter discloses prosthetic wrist implants and methods. The prosthetic wrist implants and methods disclosed herein minimize bone resection and allow natural articulation of the hand. An implant is utilized with a geometry that matches that of a natural wrist to afford a normal range of motion to the patient and also is designed to linearly engage and minimize future implant failure. An inclined articular surface of the radial component of each implant mimics the articulate surface of the distal radius bone. The small size and method of attachment of the implants minimize bone resection. The carpal component and bearing component are designed to linearly engage with the use of simple tools so that the bearing component can completely cover certain exposed portions of the carpal component, eliminating metal-on-metal contact between the radial component and the carpal component and minimizing future implant failure. The wrist implant may utilize screws, bone glue, or press-fit properties for attachment of the carpal component, the radial component, or both, and provides a stable and strong attachment with minimal bone removal.

Figure 1:
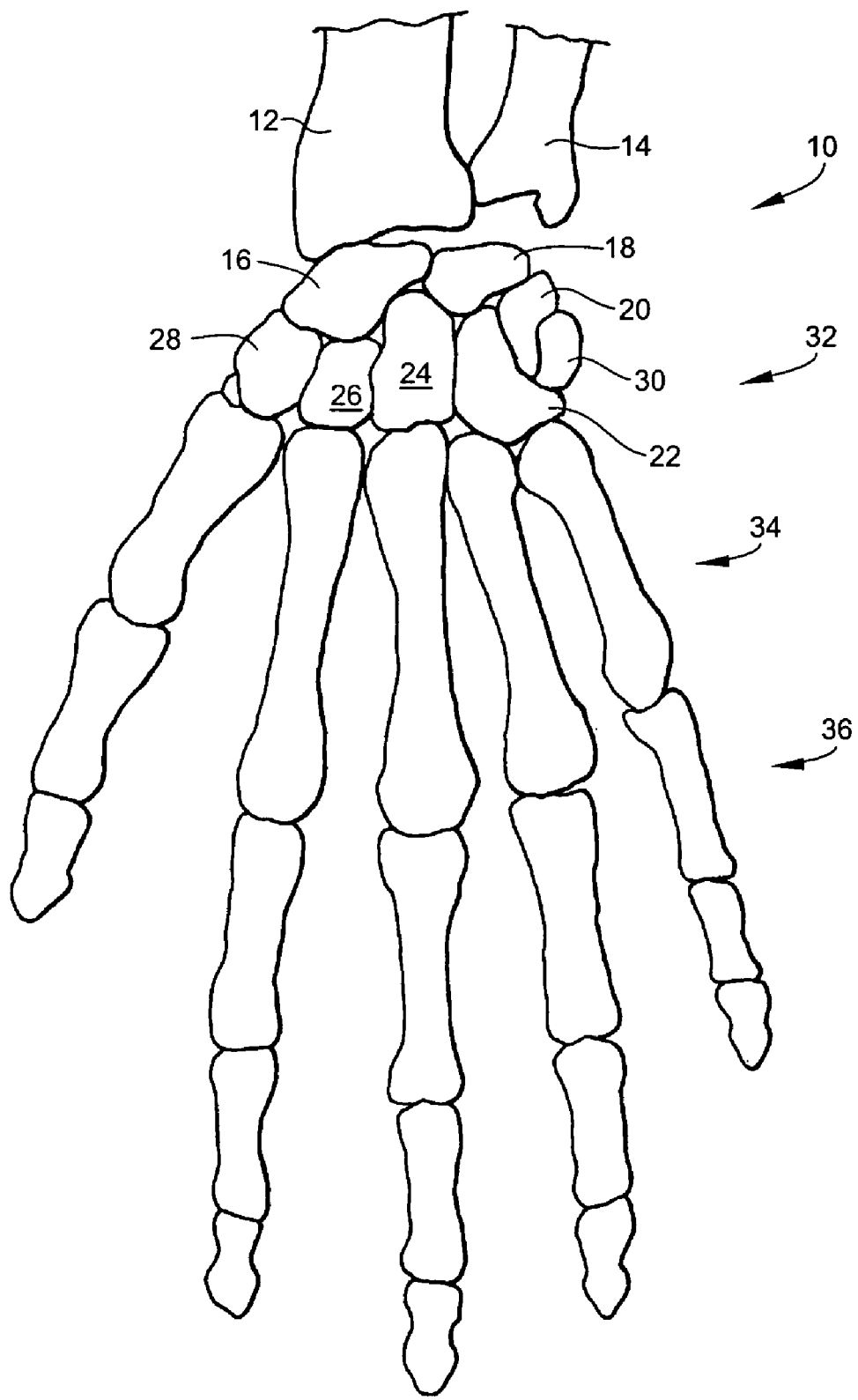
FIG. 1 is a drawing of the bones of the left hand dorsal surface.

Referring now to FIG. 1, the bones of the left hand are shown viewing the dorsal surface and including portions of the radius and ulna. In particular, FIG. 1 shows the bones of the wrist 10 including the radius 12, the ulna 14, the scaphoid 16, the lunate 18, the triquetrum 20, the hamate 22, the capitate 24, the trapezoid 26 and the trapezium 28 bones. Pisiform bone 30 is also shown. These eight bones 16-30 make up the carpus bone complex 32 of the hand. Additional bones that will not be discussed in detail include the metacarpal bones 34 and the phalanges bones 36.

It will be appreciated that scaphoid 16 and lunate 18 bones articulate with radius 12 to provide motion of the wrists. In a variety of wrists disorders, such as radio-carpal arthritis, patients may experience discomfort, pain and difficulty in moving the wrist. Prior surgical treatment of this condition involves fusion, which, as discussed previously, will prevent articulation of scaphoid 16 and lunate 18 bones with radius 12. In this procedure, a patient may have pain alleviated, but is left without motion of the wrists.

Subsequently, prosthetic wrist implants have been developed to provide an artificial articulating surface for the wrists. However, previous implants have suffered from a number of drawbacks such as those discussed above, including limited range of motion and excessive bone resection which significantly weakens the bones in question and subjects them to a greater likelihood of fracture. Additionally, prior art prosthetic wrist implants have had cumbersome methods of apparatus assembly and have experienced dissimilar metal-on-metal contact between apparatus pieces, resulting in generation of metal particulate debris and implant failure.

Figure 2C:
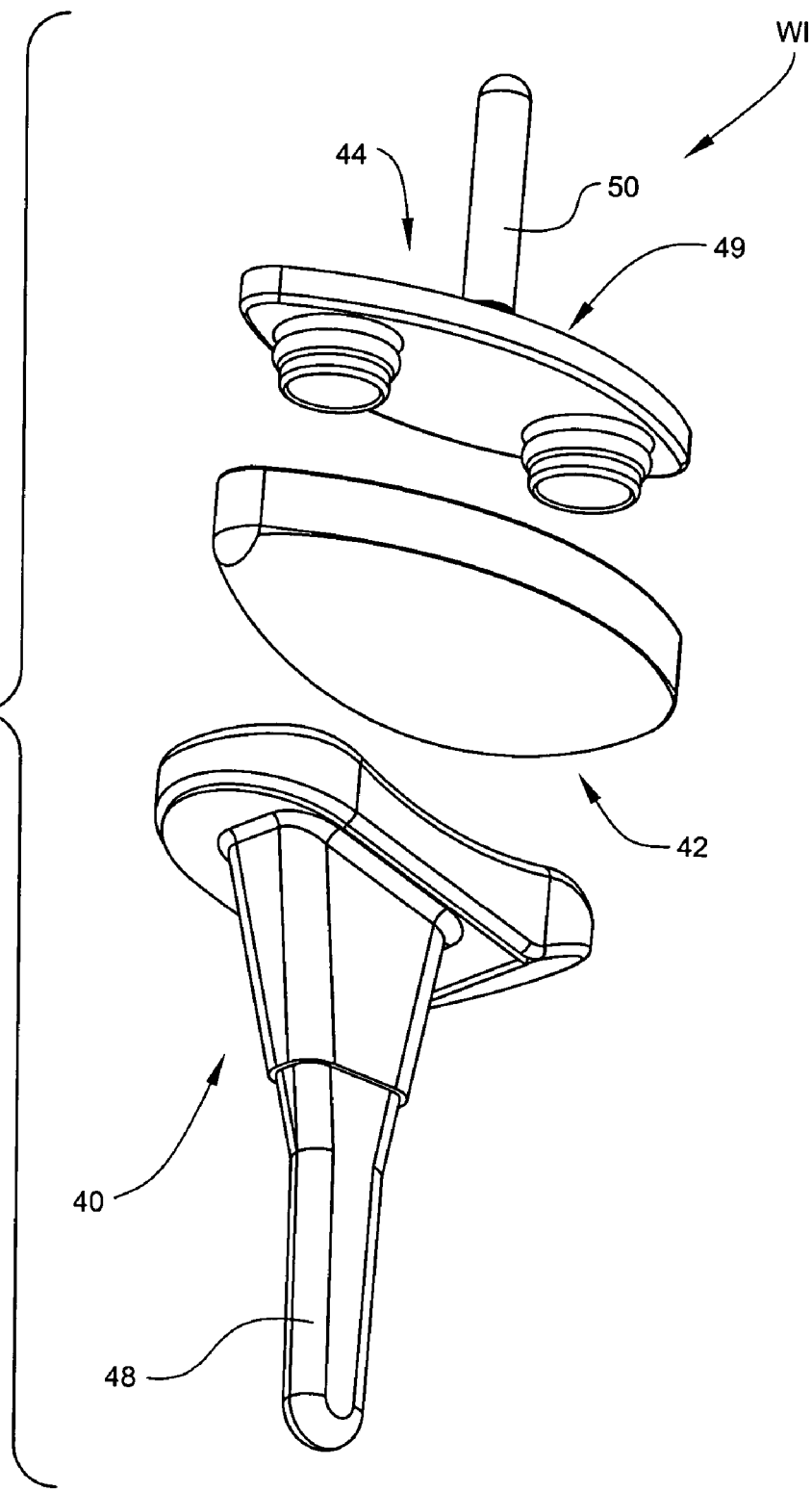
Figure 2D:
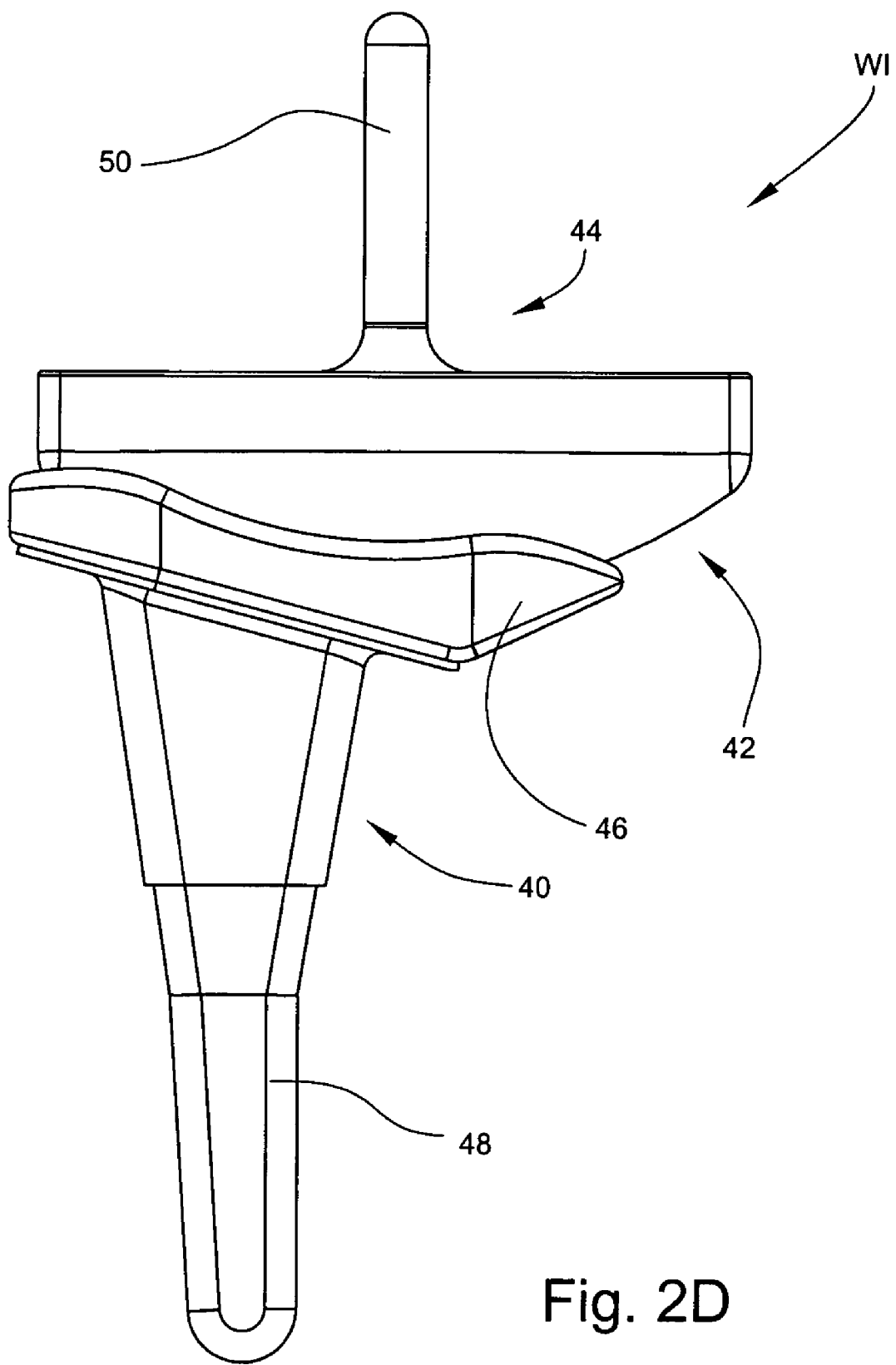
Figure 2E:
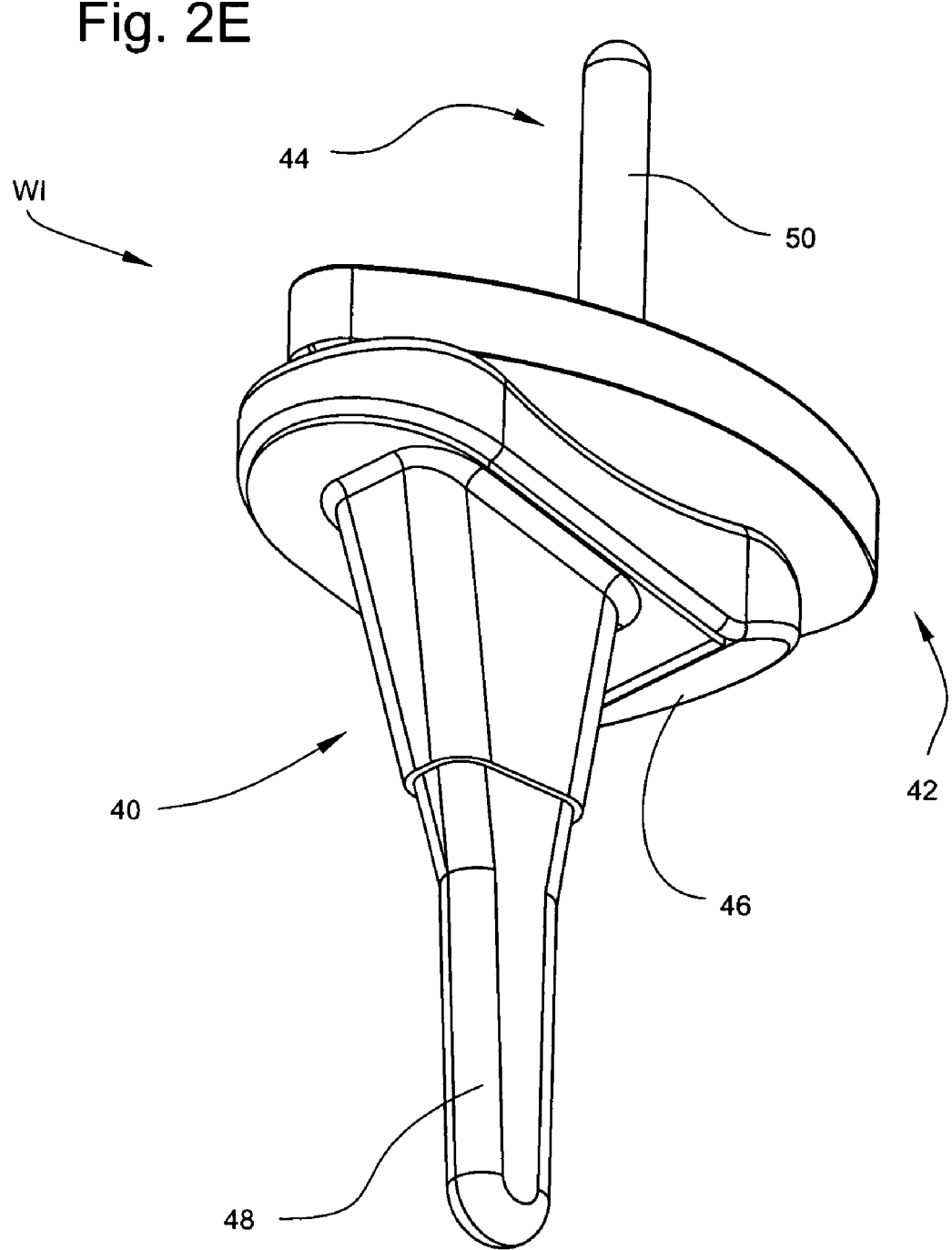
Figure 2G:
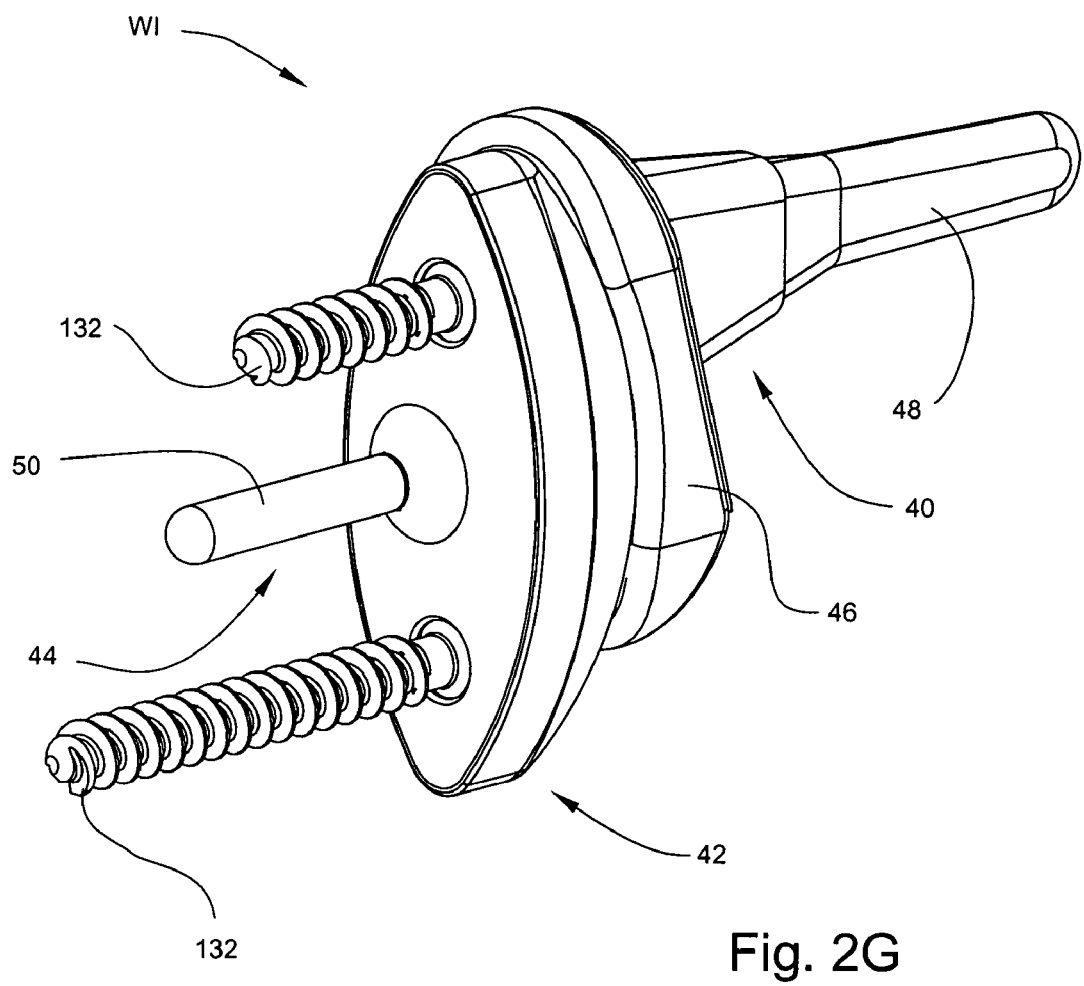

Referring now to FIGS. 2A and 2B one embodiment of the wrist implant apparatus of the present invention, generally designated WI, is shown. In FIG. 2A, a side view of wrist implant WI shows three components including: a radial implant component, shown generally as 40, that can be inserted into the distal radius bone 12 after bone osteotomy; a carpal implant component, shown generally as 44, that can be inserted into the proximal carpus bone complex 32 after bone osteotomy; and an articulating bearing component, shown generally as 42, that can connect rigidly to carpal component 44 and articulate unconstrained with radial component 40. Similarly, FIG. 2B shows these three components in a front view. It is notable that, as best as seen in the side view, radial implant component 40 of prosthetic wrist implant WI incorporates a bearing guide base member 46 which is tilted with respect to the axis of radius bone 12 into which a radial stem 48 is inserted. Carpal implant component 44 includes a planar base member 49 and a post member 50 that is inserted into the capitate 24 of carpus bone complex 32. As shown in FIGS. 2C-2E, bearing component 42 is mounted ridgedly to planar carpal base member 49 and provides a low friction surface that is articulated against bearing guide base member 46. As shown in FIGS. 2F and 2G, wrist implant WI may further include bone screws 132 for fixation of carpal implant component 49, primarily to hamate 22, and trapezoid 26 of carpus bone complex 32.

Figure 3A:
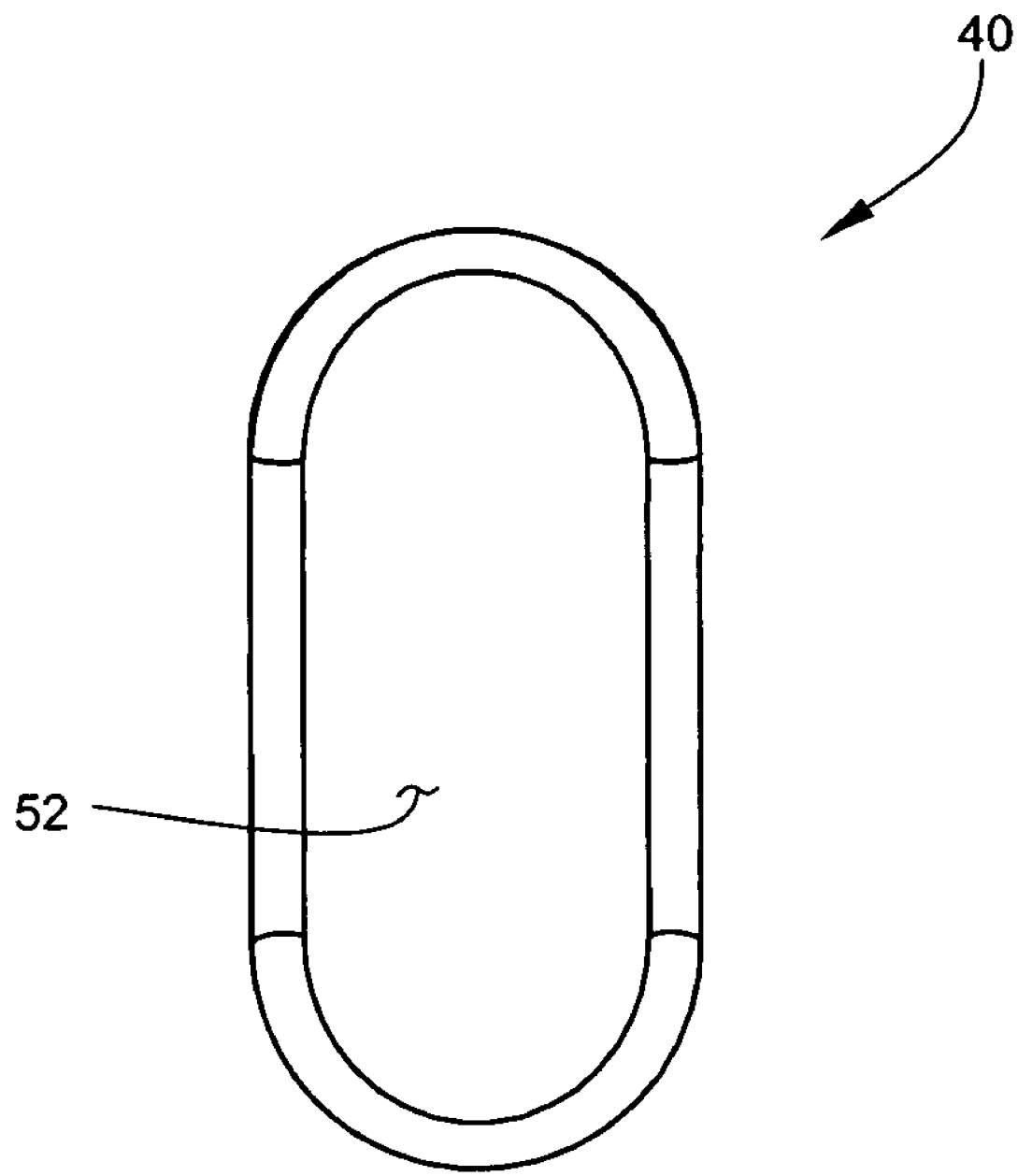
FIGS. 3A-3G are various views of the radial implant component of the wrist implant apparatus.
Figure 3B:
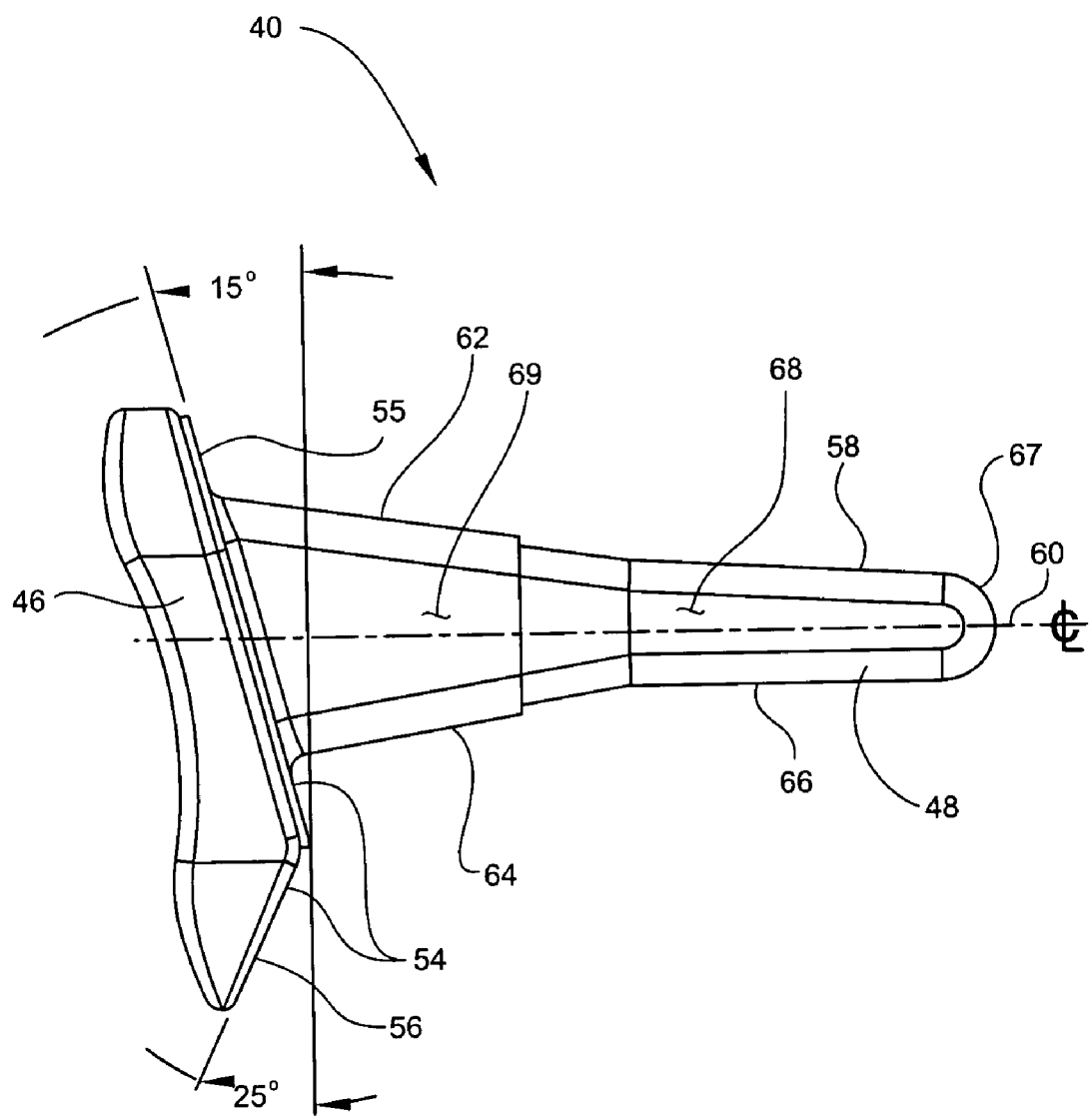
Figure 3C:
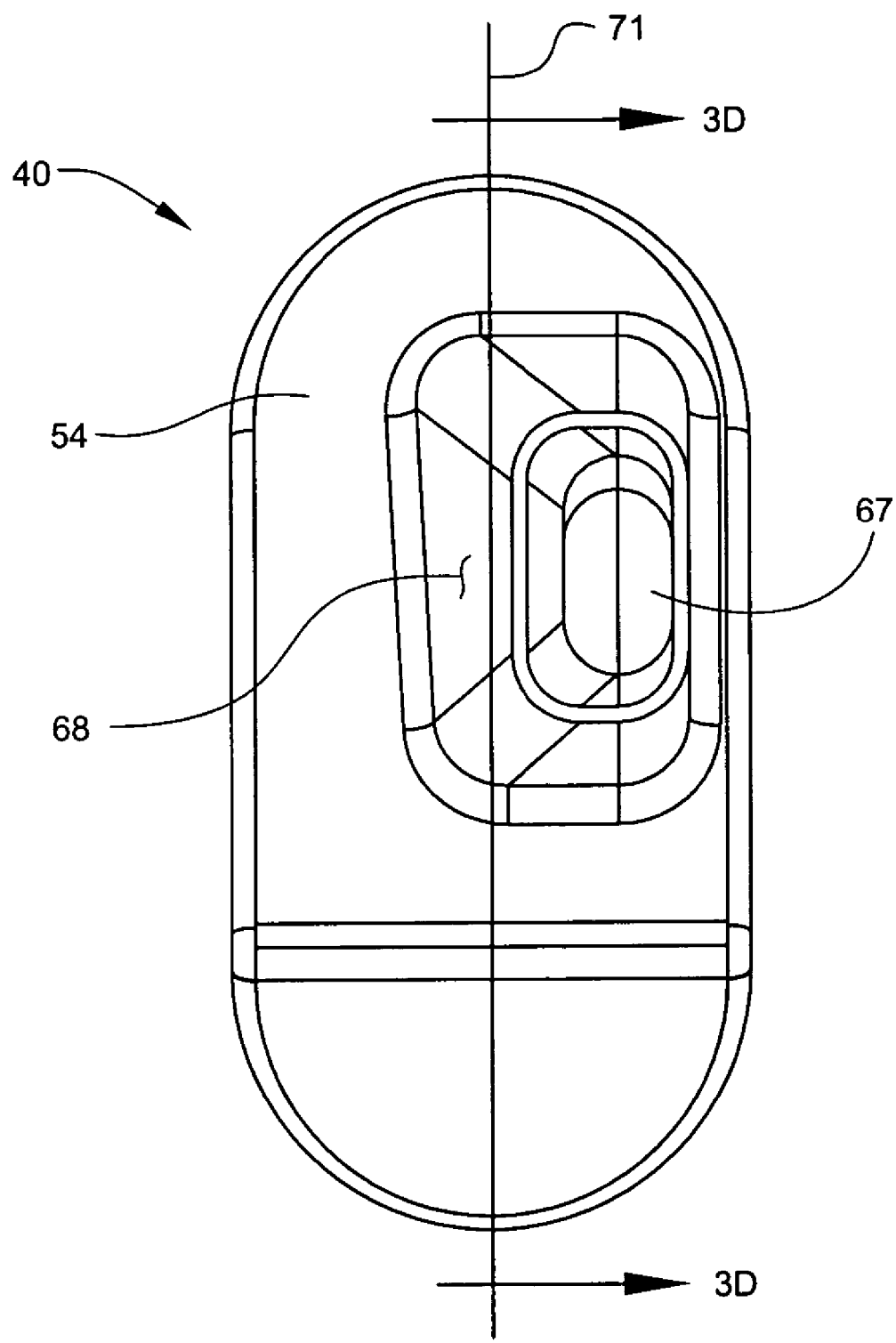
Figure 3D:
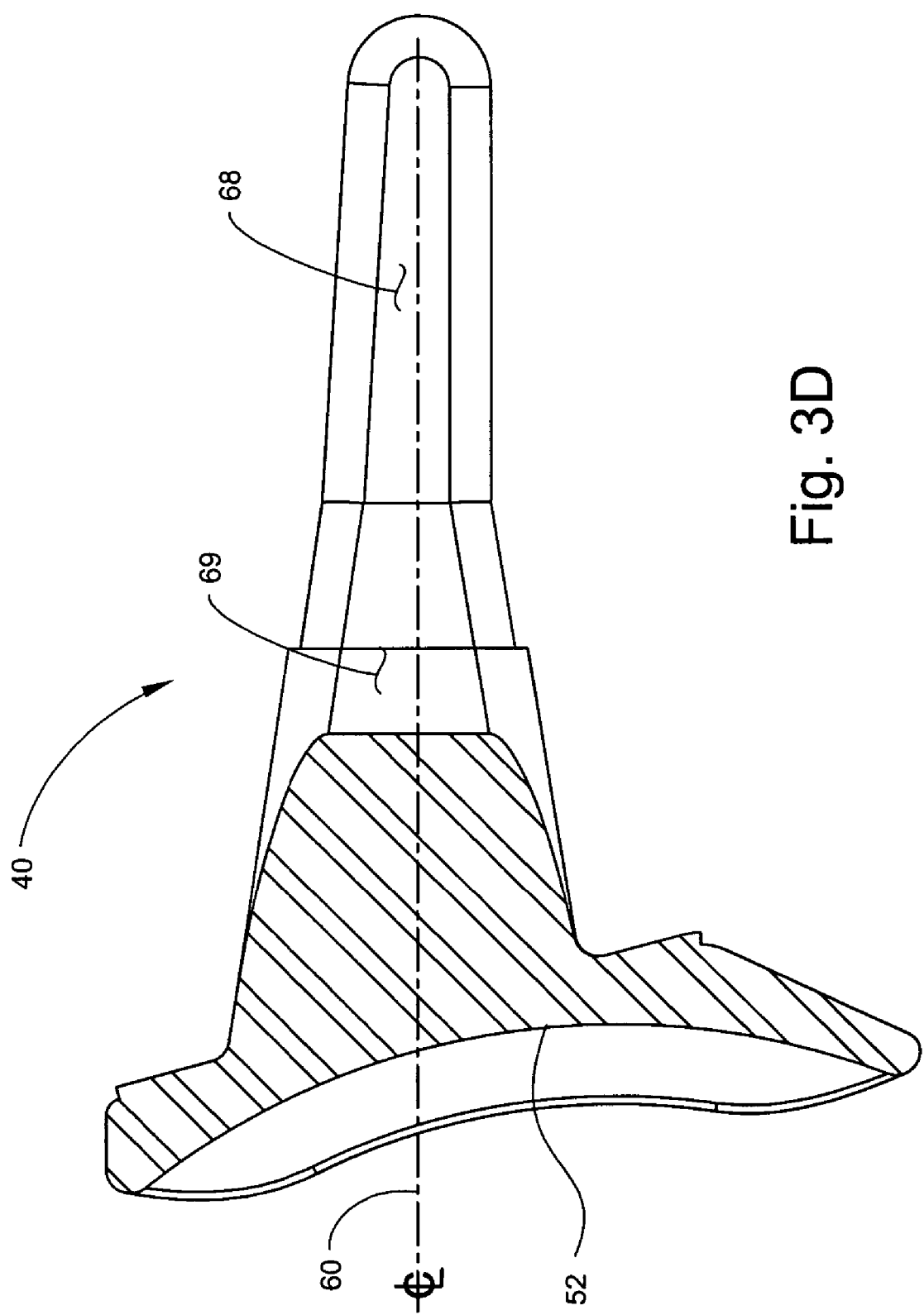

Referring now to FIGS. 3A-3E, one embodiment of radial implant component 40 is shown in more detail. FIGS. 3A-3D show bearing guide base member 46 that includes an upper bearing surface 52 and a lower surface 54. Upper bearing surface 52 is substantially concave or curved in a preferred embodiment. As shown in FIG. 3D, this curved surface 52, in the preferred embodiment, can have a major radius preferably ranging from about 26.0 to about 35.3 mm and is highly polished to allow direct contact with carpal bearing component 42 as will be described in more detail below. Lower surface 54 can include a first flat portion 55 and a second flat portion 56 tilted at an angle with respect to first flat portion 55. First flat portion 55 of bearing guide base member 46 is preferably disposed at about a 15 degree angle to a plane perpendicular with respect to the axis of the radius 60 wherein first flat portion 55 abuts against the surface of radius bone 12 as described in more detailed below. Second flat portion 56 of bearing guide base member 46 is preferably disposed at about a 25 degree angle to a plane perpendicular with respect to the axis of the radius 60. The angling of first flat portion 55 and second flat portion 56 allows radial component 40 to be placed in the patient's wrist without resecting or cutting ulna bone 14.

As shown in FIGS. 3B and 3C, an elongated radial stem or post 48 is attached to and extends from lower surface 54. Radial stem 48 further includes a lower stem section 68 and an upper stem section 69. Stem 48 also is preferably generally tapered from lower surface 54 at surfaces 58, 62, 64, and 66 as shown in FIG. 3B. As shown in FIG. 3C, radial stem 48 preferably tapers down from its attachment from the shape shown at upper stem section 69, where it is attached to lower surface 54, down to a rounded end portion 67. Additionally, radial stem 48 is axis-symmetrical and is preferably dorsal off-center from radial centerline 71 preferably in the amount ranging from about 3.35 to about 4.60 mm as needed for either a right or left radial bone. This offset axis-symmetrical radial stem 48 improves alignment for right or left wrist placement in order to improve radial component 40 stability in the intramedullary canal of radius bone 12 and to improve surgical technique.

Figure 3E:
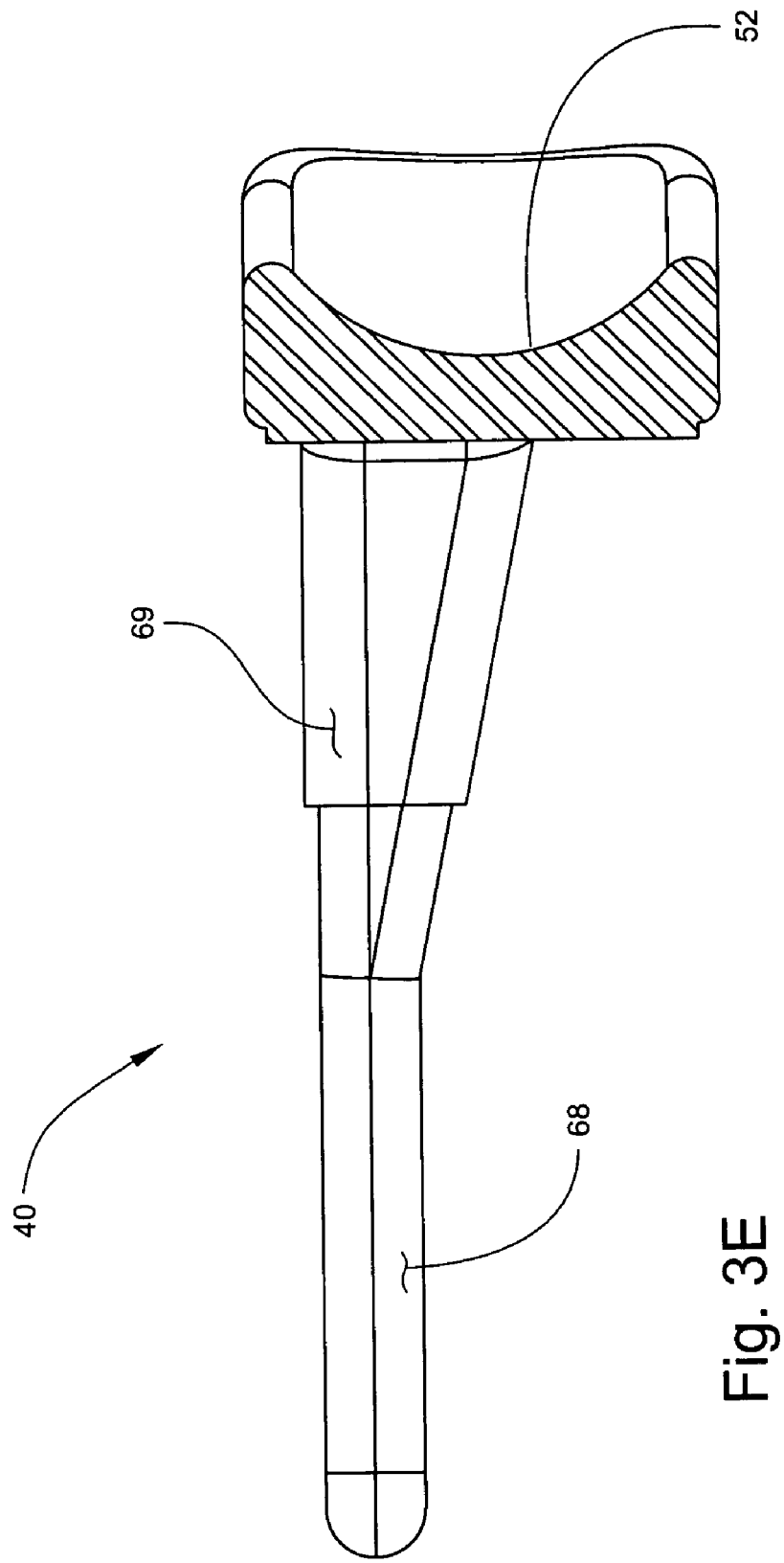

FIG. 3E is a side sectional view of the radial implant component 40 showing that upper bearing surface 52 along the side axis has a minor radius preferably ranging from about 7.10 to about 9.75 mm. In the preferred embodiment, radial implant component 40 is made of cast material such as CoCrMo as per specification ASTM F75. However, it will be appreciated by those skilled in the art that other materials having sufficient strength and biocompatibility may also be employed.

Figure 3F:
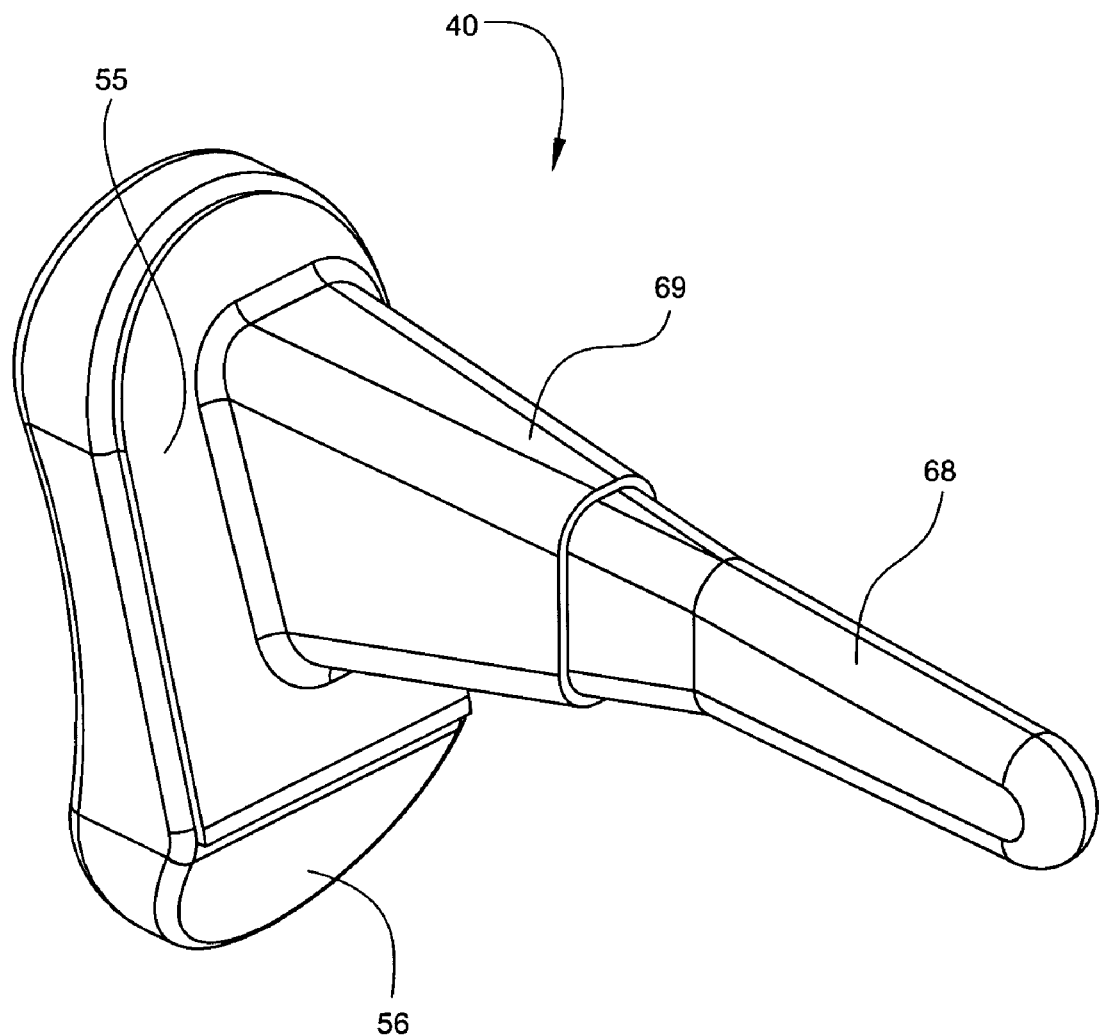
Figure 3G:
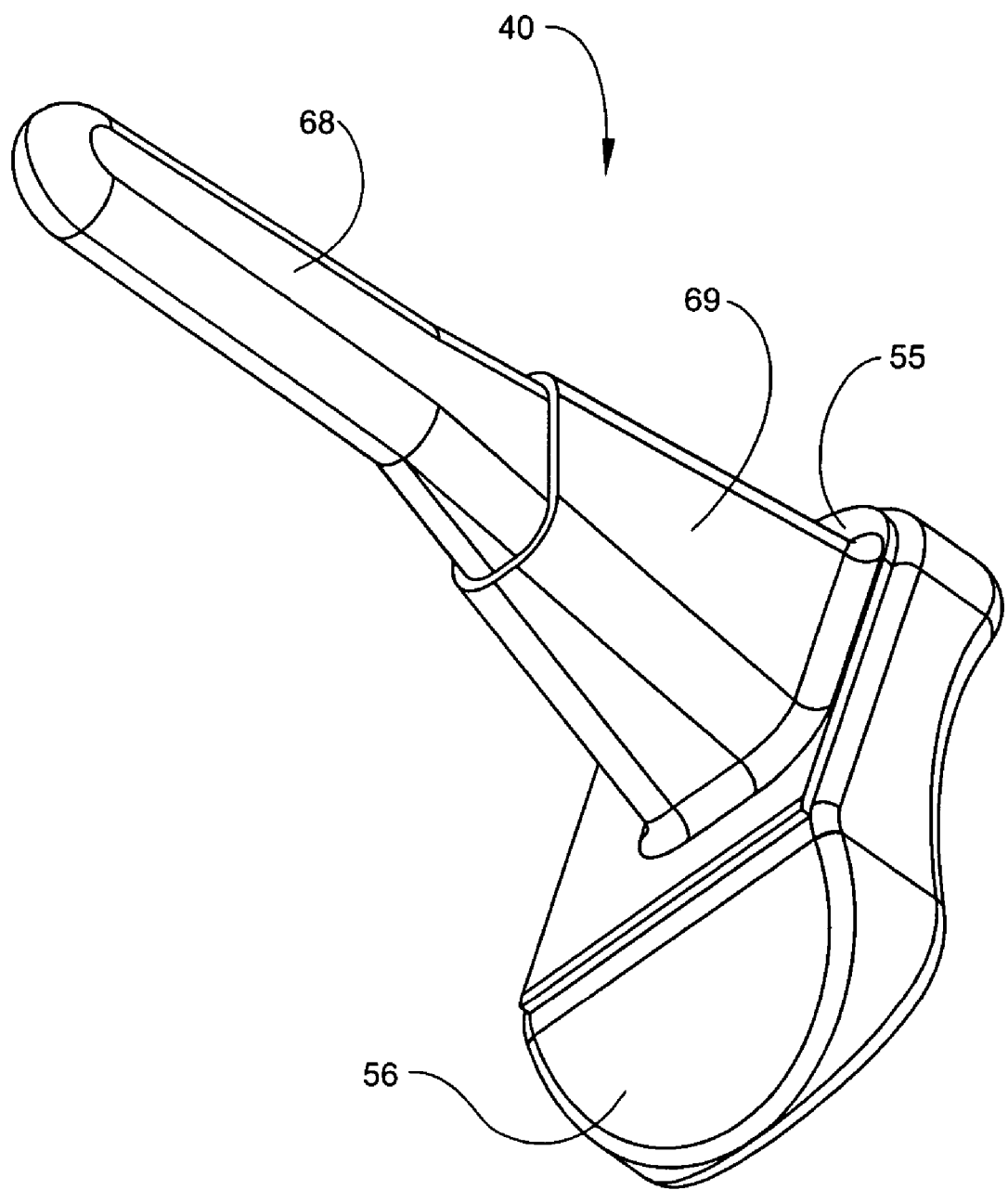

Referring to FIGS. 3F and 3G, as can be appreciated by those of skill in the art, portions of radial component 40 may further preferably contain a porous coating of CoCrMo alloy spherical powder as per ASTM F75 and F1377 requirements for the aid in osteointegration of the implant and to aid in allowing radial component 40 to be in a press-fit relationship with radial bone 12. The porous coating can comprise metal beads defined by sieve size −50+75 consisting of two layers with a coating thickness (average) of 0.4276 mm (0.0168 in) wherein the porous coating is bonded to the substrate of radial component 40 by a sintering process. Typically, the beaded porous coating will cover upper stem section 69 of radial stem 48 and will also cover first flat portion 55 of lower surface 54, as these portions of radial component 40 are in contact with cancellous bone within radial bone 12. In order to accommodate the different wrist sizes found in a variety of patients, radial component 40 can be made is four sizes ranging from extra-small to large.

Figure 4A:
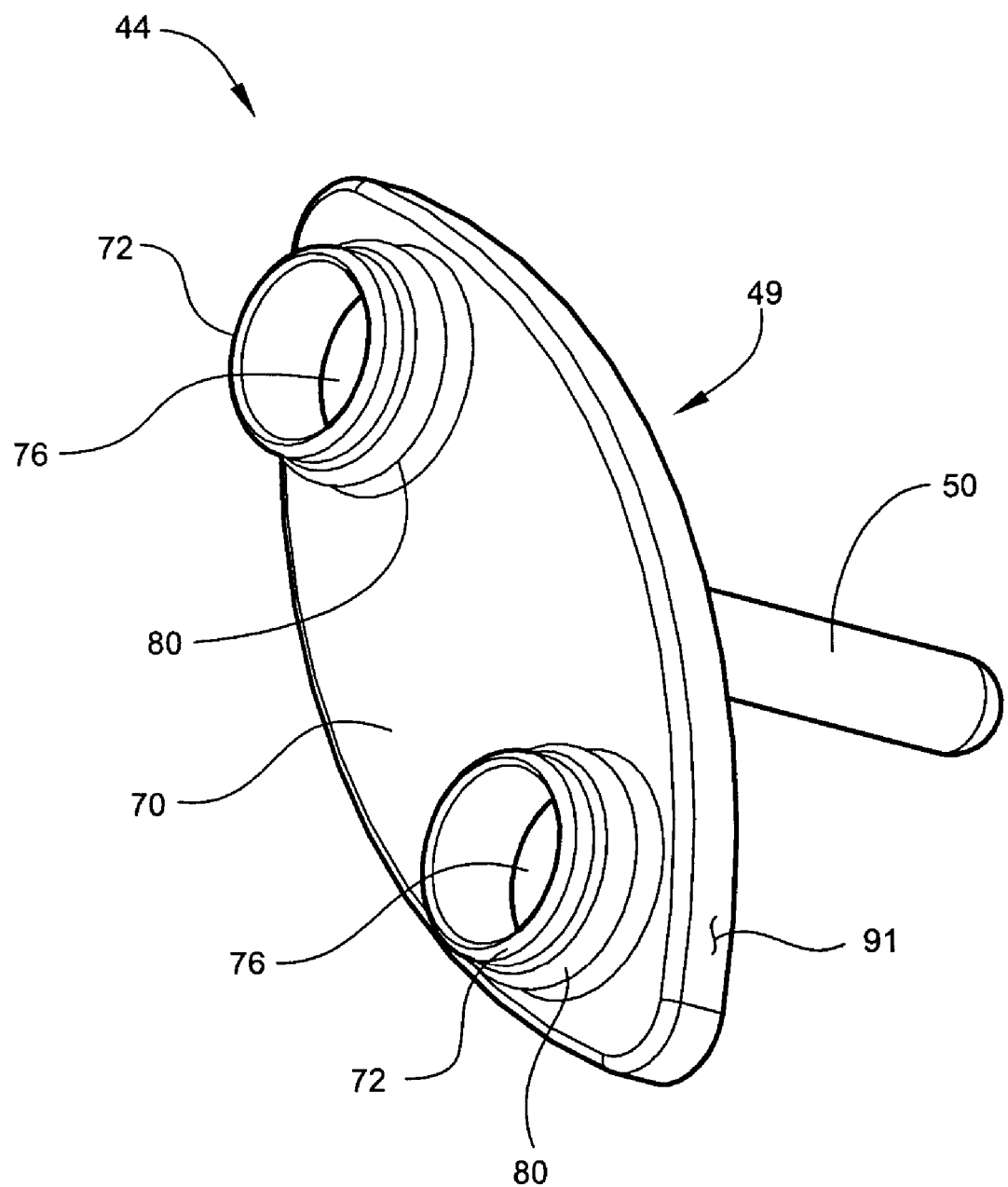
FIGS. 4A-4F are various views of the carpal implant component of the wrist implant apparatus.
Figure 4B:
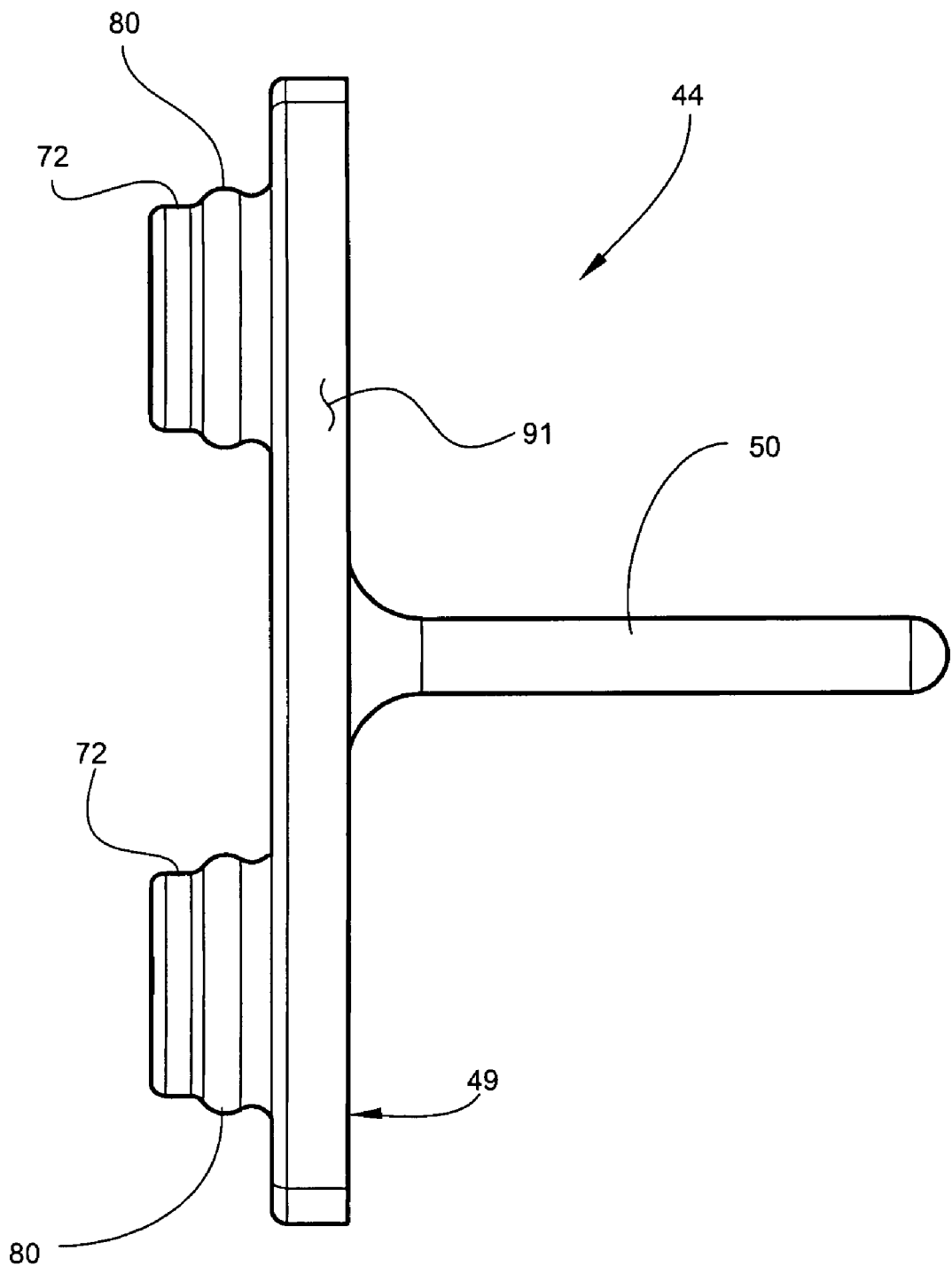
Figure 4C:
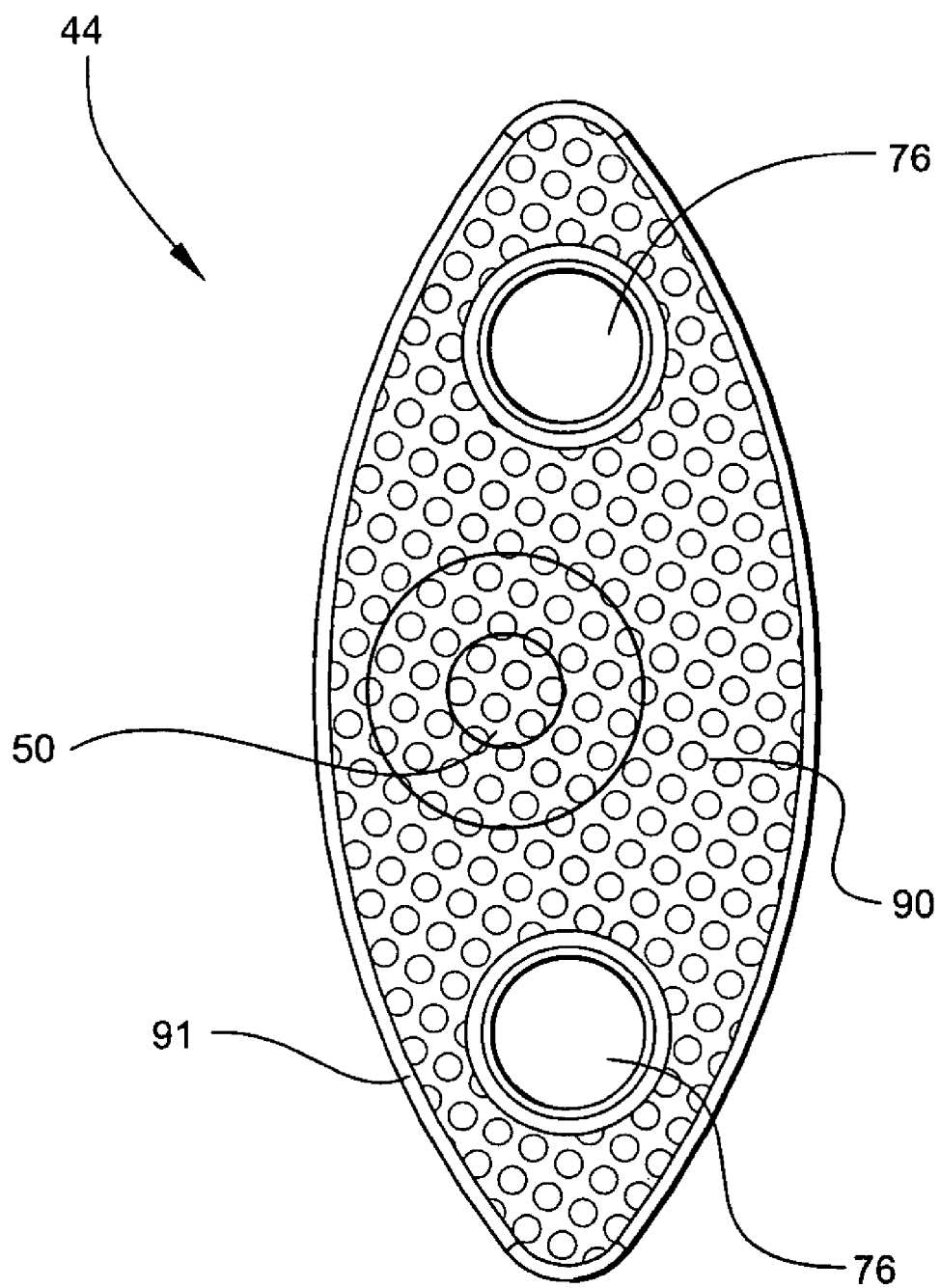

Referring now to FIGS. 4A-4F, an embodiment of carpal implant component 44 is shown. As shown in FIGS. 4A-4C, carpal component 44 includes a planar base member 49 including a lower surface 70, and upper surface 90, and outer edge 91. While lower surface 70 has at least one, preferably cylindrical, locking socket post or protrusion 72 attached to and extending therefrom, lower surface 70 is shown in an advantages embodiment having two locking socket protrusions 72. Locking socket protrusions 72 also preferably have tapered holes 76, with spherical radii at the base of the hole, through which attachment screws 132 (described below) can be inserted into carpal bone complex 32. As shown in more detail in FIG. 4B, locking socket protrusions 72 preferably each include a raised socket ring or external lip 80 which surrounds the circumferences of socket protrusions 72. In the preferred embodiment, each socket ring 80 is configured to engage with a groove in a socket recess in carpal bearing component 42 as described in more detail below.

Figure 4D:
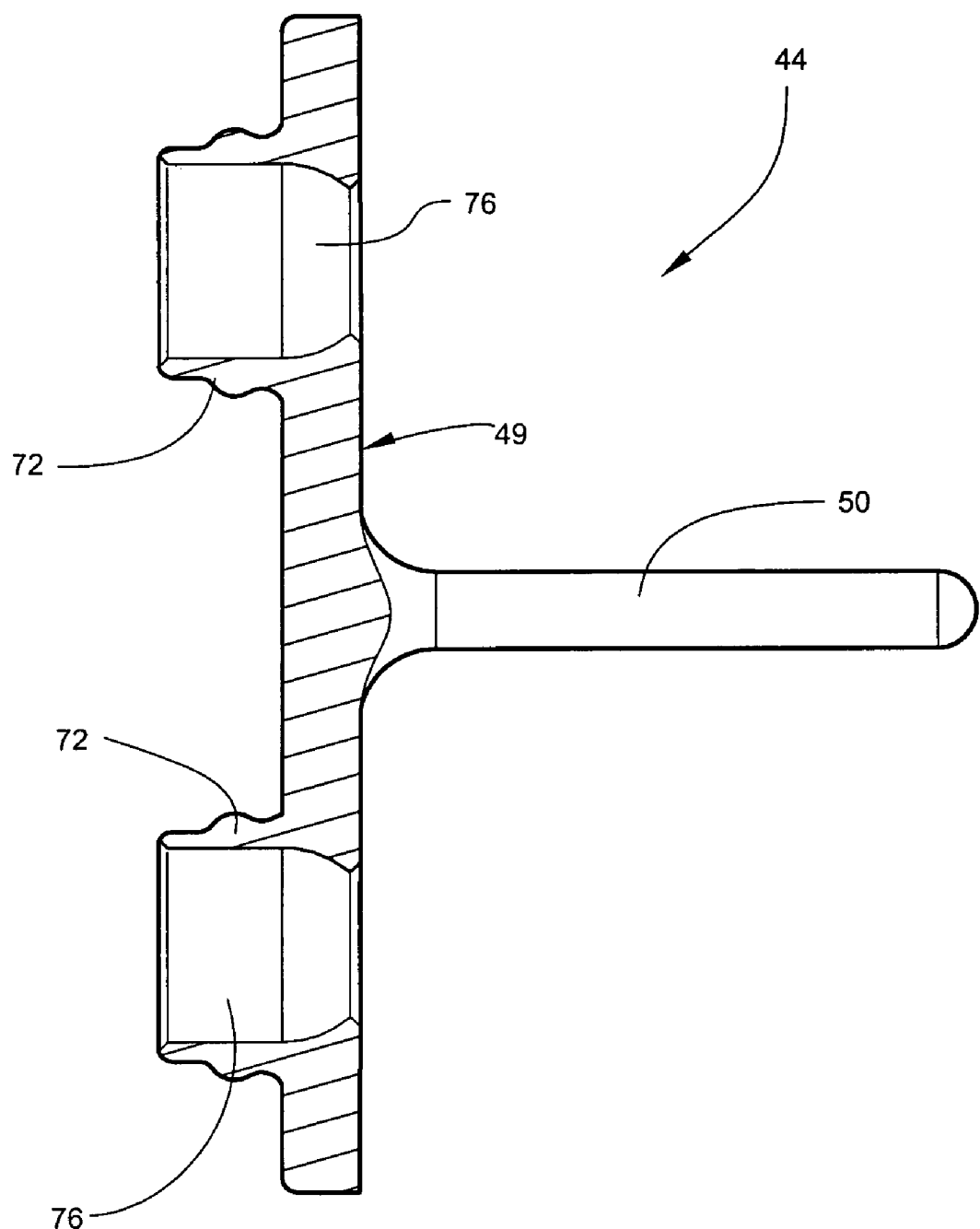
Figure 4E:
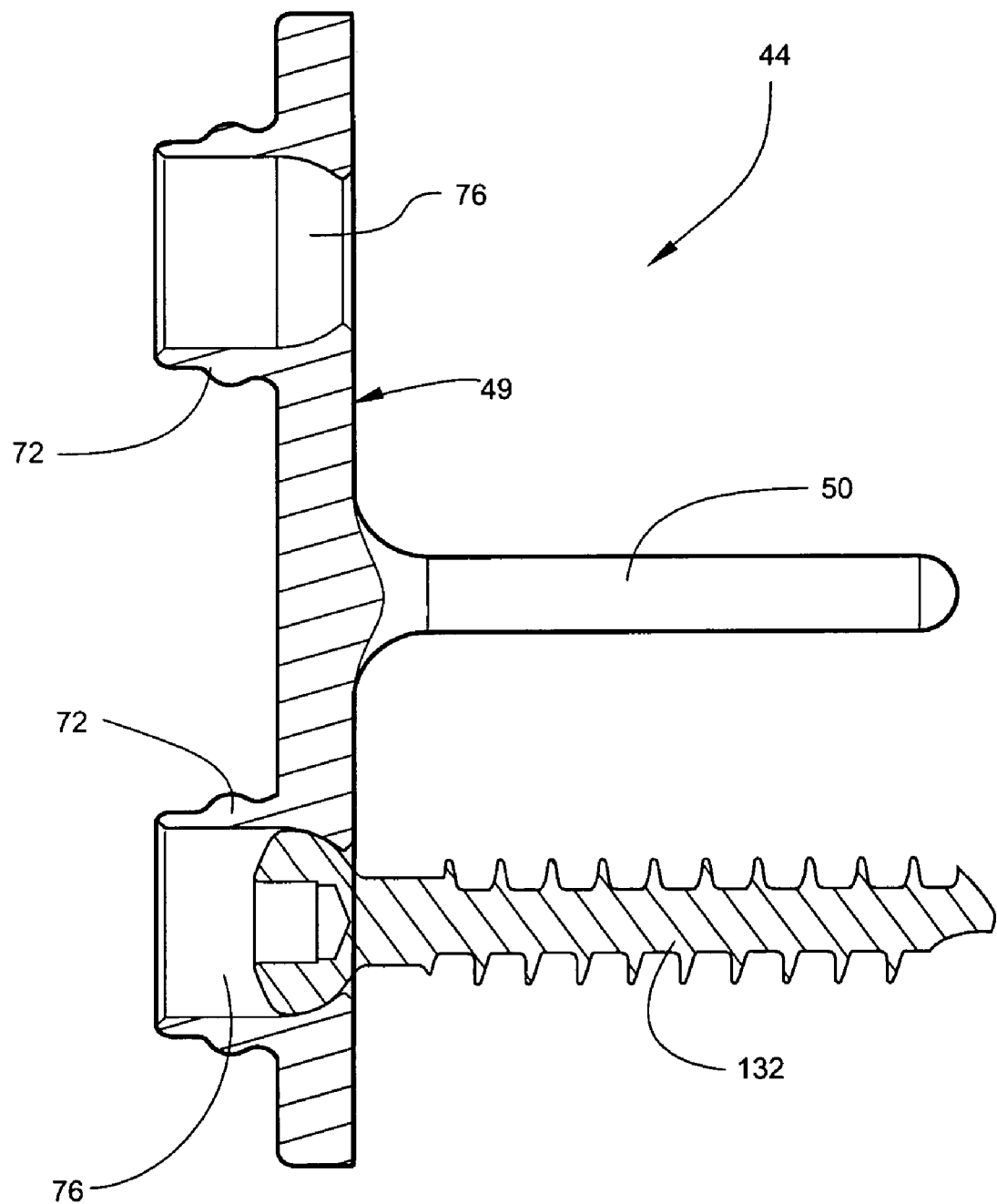
Figure 4F:
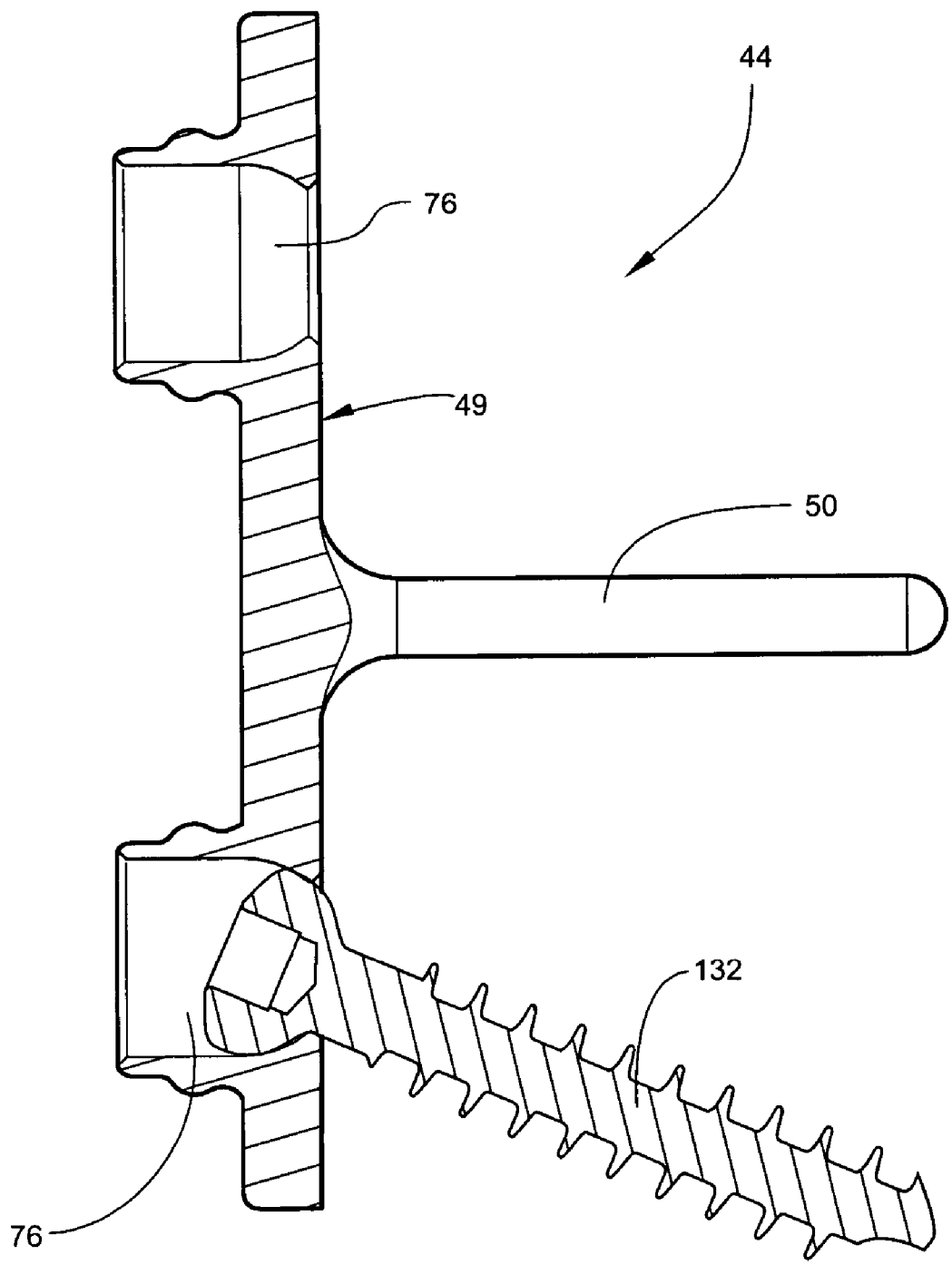

Elongated carpal post member 50 protrudes preferably perpendicularly from upper surface 90 of carpal implant component 44. FIG. 4C shows the location of tapered holes 76 and post 50 of a preferred embodiment when viewed from upper surface 90 of carpal implant component 44. Referring now to FIG. 4D, carpal post 50 is shown including a porous beaded coating of Commercially Pure (C.P.) Grade 2 Titanium spherical powder as per ASTM F67 and F1580 requirements, which serves to secure post 50 into carpal bone complex 32 once it is implanted by enhancing the press-fit relationship between post 50 and carpal bone complex 32 and by aiding in osteointegration of the implant. The porous coating can be metal beads defined by sieve size −50+70 and be applied in two layers with a coating thickness (average) of about 0.386 mm (0.0152 in), covering the entire carpal post 50 and may additionally cover the entire surface of upper surface 90 (FIG. 4C). The porous coating is bonded to the substrate of carpal post 50 by a sintering process.

As described in more detail below, post 50 is preferably inserted into capitate bone 24 and may include bone screws 132 (FIGS. 4E and 4F) that are inserted into holes 76 are screwed into hamate 22 and trapezoid bones 26. Carpal implant component 44 is preferably made of titanium such as Ti-6A1-4V ELI as per specification ASTM 136, although it will be appreciated by those skilled in the art that other materials having sufficient strength and biocompatibility may also be employed. In order to accommodate the different wrist sizes found in a variety of patients, carpal component 44 can be made in multiple, such as four, sizes ranging from extra-small to large.

Figure 5A:
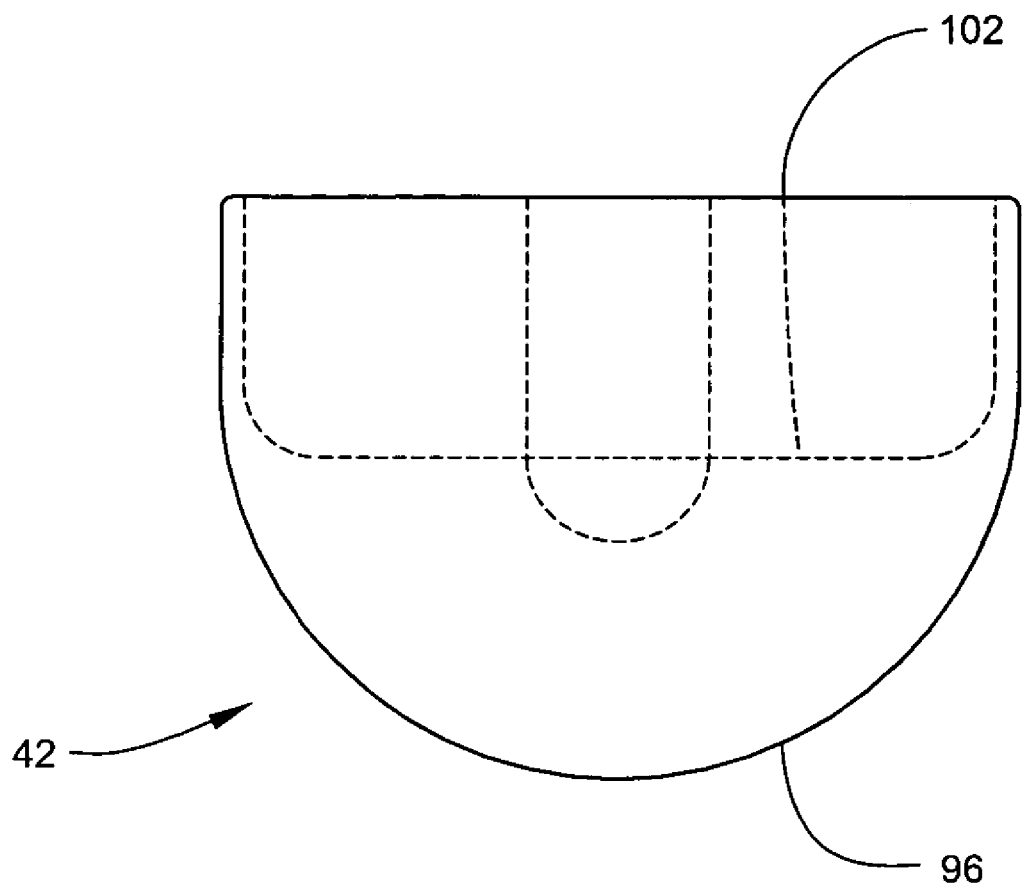
FIGS. 5A-5E are various views of the articulating bearing component of the wrist implant apparatus.
Figure 5B:
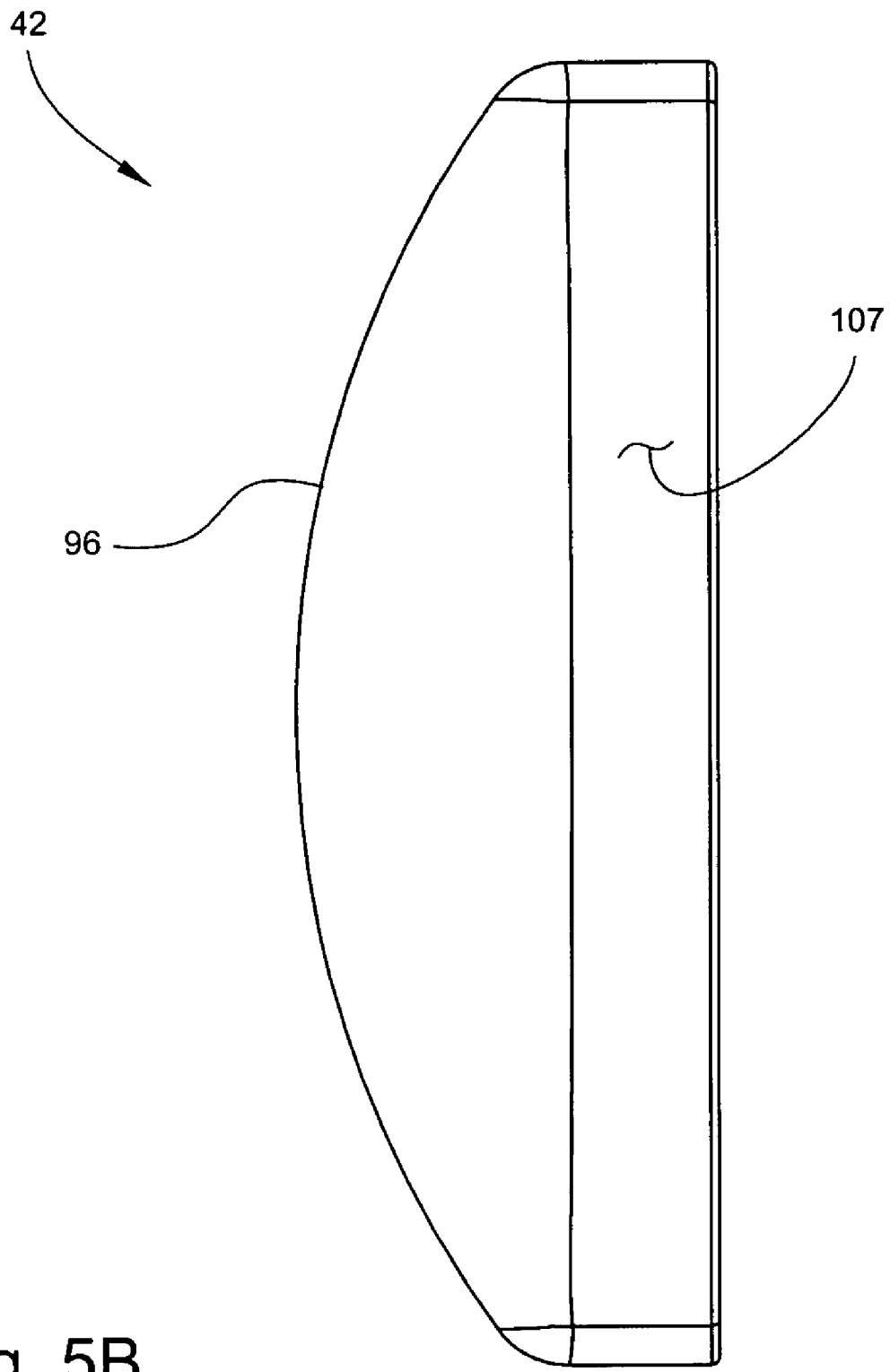

Referring now to FIGS. 5A-5E, a preferred embodiment of articulating bearing component 42 is shown. Bearing component 42 imitates the articulation of lunate 18 and scaphoid 16 bones and is adapted for placement between radial component 40 and carpal implant component 44. Bearing component 42 as seen in FIG. 5A in side end view includes an at least substantially planar upper surface 102 and preferably has a convex articulating lower bearing surface 96 which, in a preferred embodiment, can have a minor radius ranging from about 7.10 to about 9.75 mm. The convex radii of lower bearing surface 96 is designed to match the corresponding concave radii of upper bearing surface 52 of radial component 40. These matching radii allow a total line (surface to surface) contact between bearing component 42 and radial component 40 during all implant rotations (radial-ulnar and flexion-extension) and torsional rotation. This constant surface-to-surface contact between bearing component 42 and radial component 40 results in superior stability of the apparatus and decreased material wear.

As shown in FIGS. 5A-5E, carpal bearing upper surface 102 includes an extended skirt 107 around the perimeter of and extending from upper surface 102. Skirt 107 may be constructed continuously around the perimeter of upper surface 102 or may be constructed intermittently with gaps around the perimeter of upper surface 102. Additionally, skirt 107 comprises a skirt upper edge 105 defined as the edge of the skirt extended furthest away from upper surface 102. As will be described in more detail hereinbelow, when bearing component 42 is fully engaged with carpal component 44, skirt 107 at least substantially surrounds carpal component outer edge 91 and skirt upper edge 105 is disposed upon a plane that is at least substantially coplanar with upper surface 91 of planer base member 49 of carpal component 44.

Figure 5C:
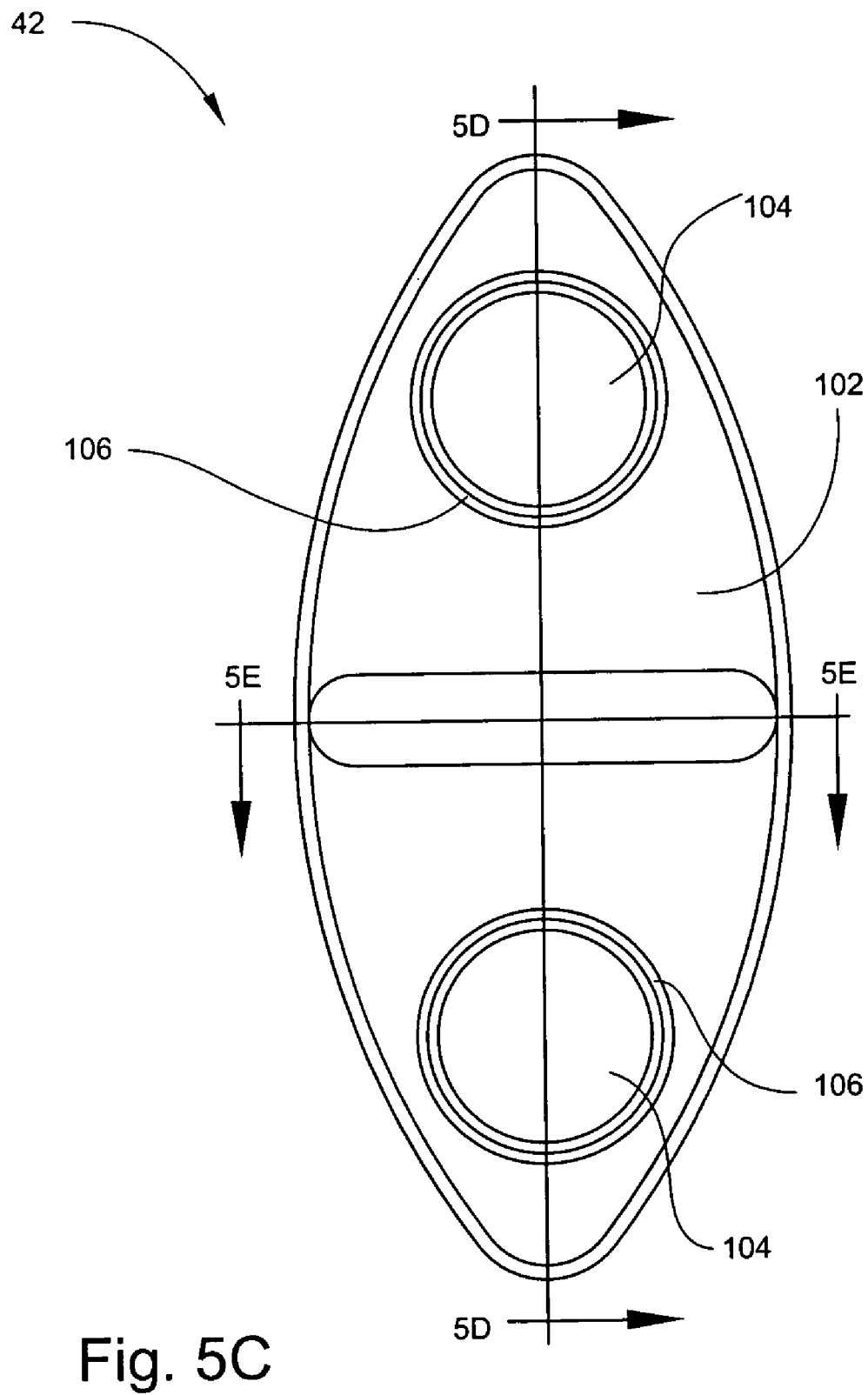
Figure 5D:
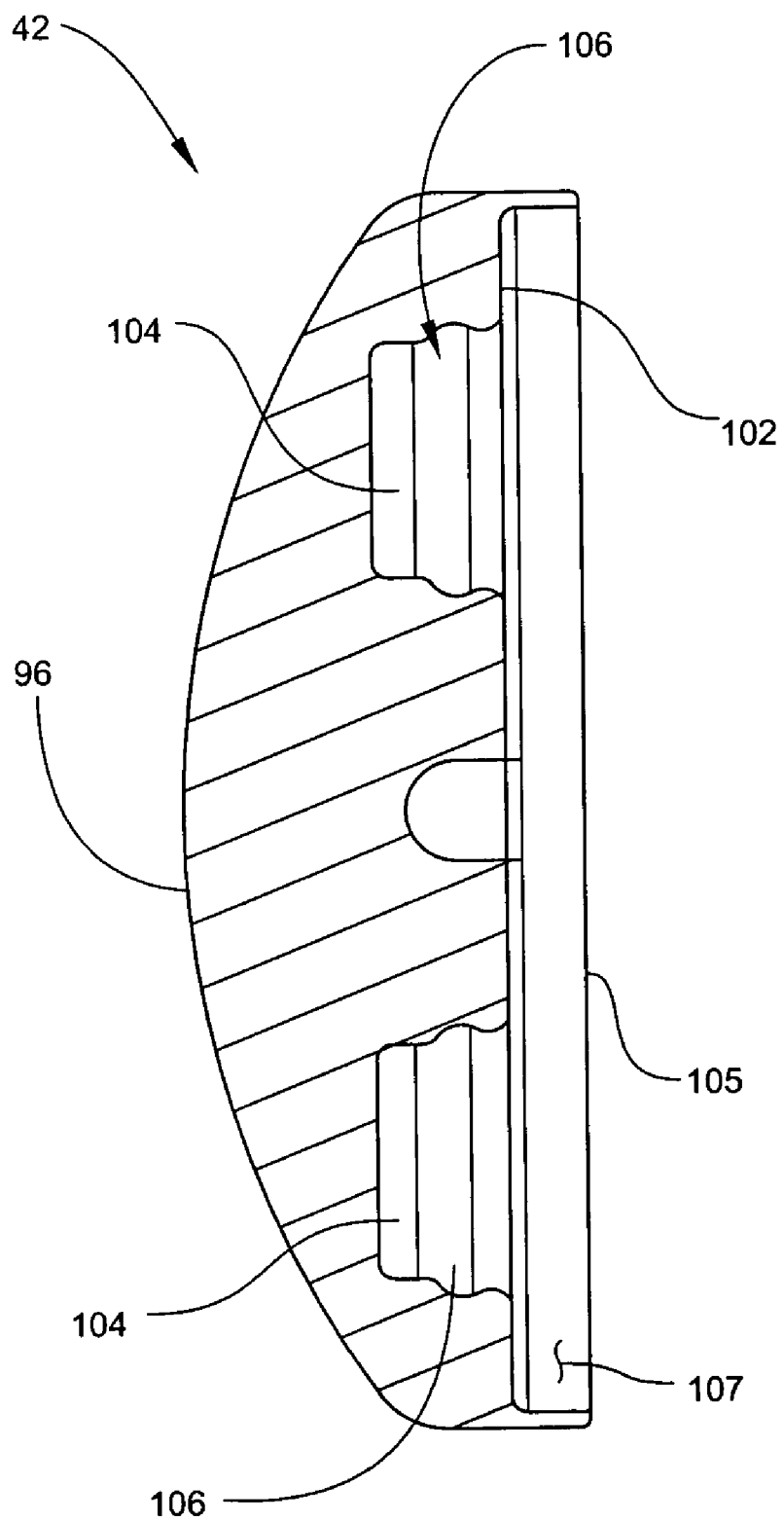
Figure 5E:
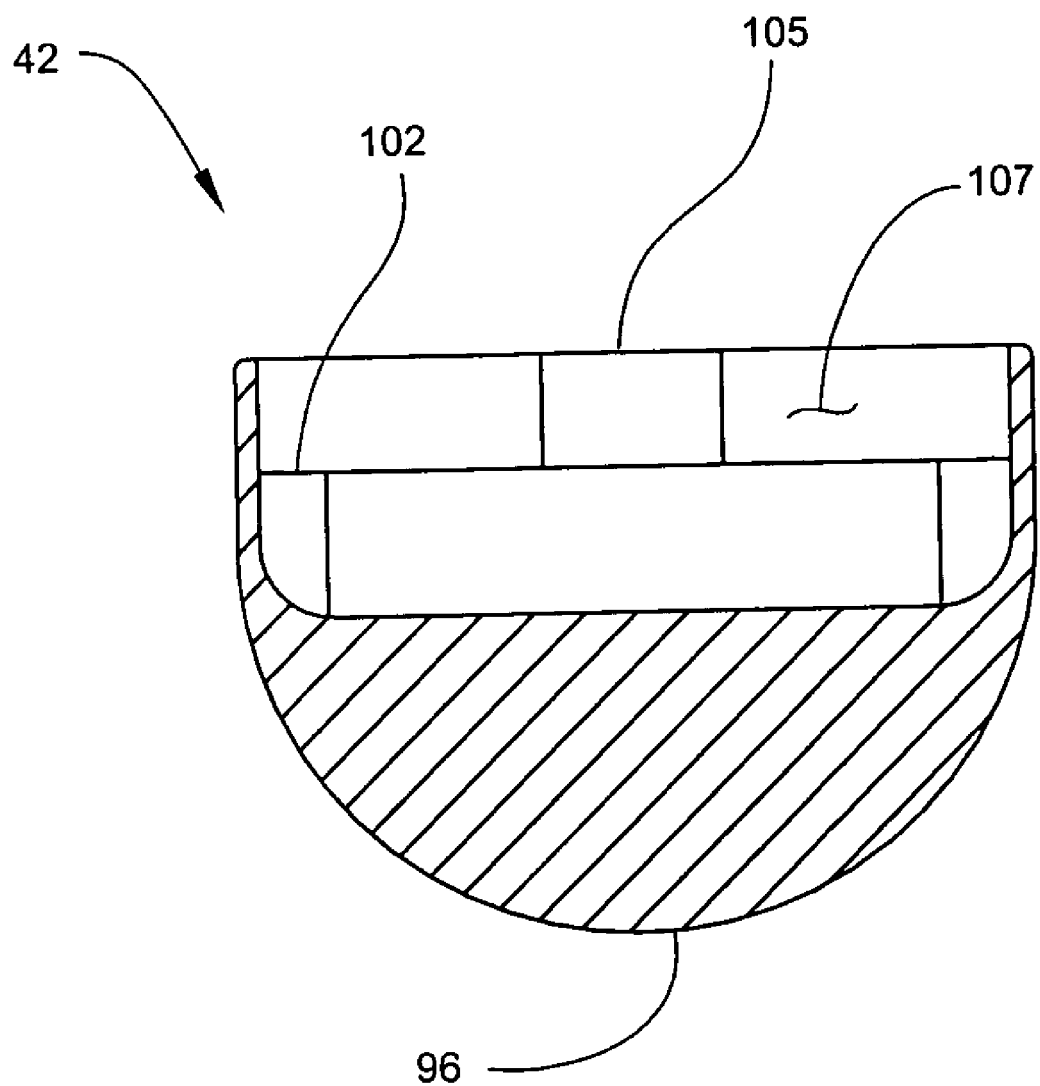

While upper surface 102 also preferably includes at least one socket recess 104, two socket recesses 104 are shown in FIGS. 5C and 5D, with end socket recess 104 having an internal socket groove portion 106. When installing or fitting bearing component 42 onto carpal implant component 44, each socket recess 104 engages with a locking socket protrusion 72 as bearing component 42 is compressed onto lower surface 70 of carpal implant component 44 through a linear compressive impaction load directed on carpal bearing component 42 towards carpal implant component 44. When fully engaged across lower surface 70, socket external lip or ring 80 of carpal locking socket protrusions 72 will fully engage with socket groove portion 106 of socket recesses 104 thereby preventing bearing component 42 from separating from lower surface 70 of carpal implant component 44 once installed.

Extended skirt 107 extending from upper surface 102 extends around carpal component planar base member 49, when fully fitted together, such that skirt 107 at least substantially surrounds carpal component outer edge 91. When bearing component 42 and carpal component 44 are fully engaged, skirt upper edge 105 is disposed upon a plane that is substantially coplanar with the upper surface 90 of base member 49 of carpal component 44. This fitting of skirt 107 around carpal component base member 49 can prevent any metal-on-metal contact between radial component 40 and carpal component 44. A problem encountered by prior art wrist implants, metal-on-metal contact between radial component 40 and carpal component 44 can lead to generation of metal particulate which can lead to contamination of tissue, degenerating the life of the tissue and leading to cell death. This degenerating effect can lead to implant loosening and failure. Therefore, the use of a linear attachment mechanism for attaching carpal component 44 and bearing component 42, along with protective skirt 107 leads to a longer lasting implant with lower risk of implant failure.

Articulating bearing component 42 in the preferred embodiment is made from ultra high molecular weight polyethylene (UHMWPe). However, it will be appreciated that other low friction polymeric materials may also be employed. In addition, other materials may also be used in some situations. In order to accommodate the different wrist sizes found in a variety of patients, bearing component 42 can be made in four sizes ranging from extra-small to large. Additionally, in order to accommodate the extent of radius bone 12 resection, bearing component 42 preferably has three variations of height: standard, +1 (2.5 mm taller), and +2 (5 mm taller).

Figure 6A:
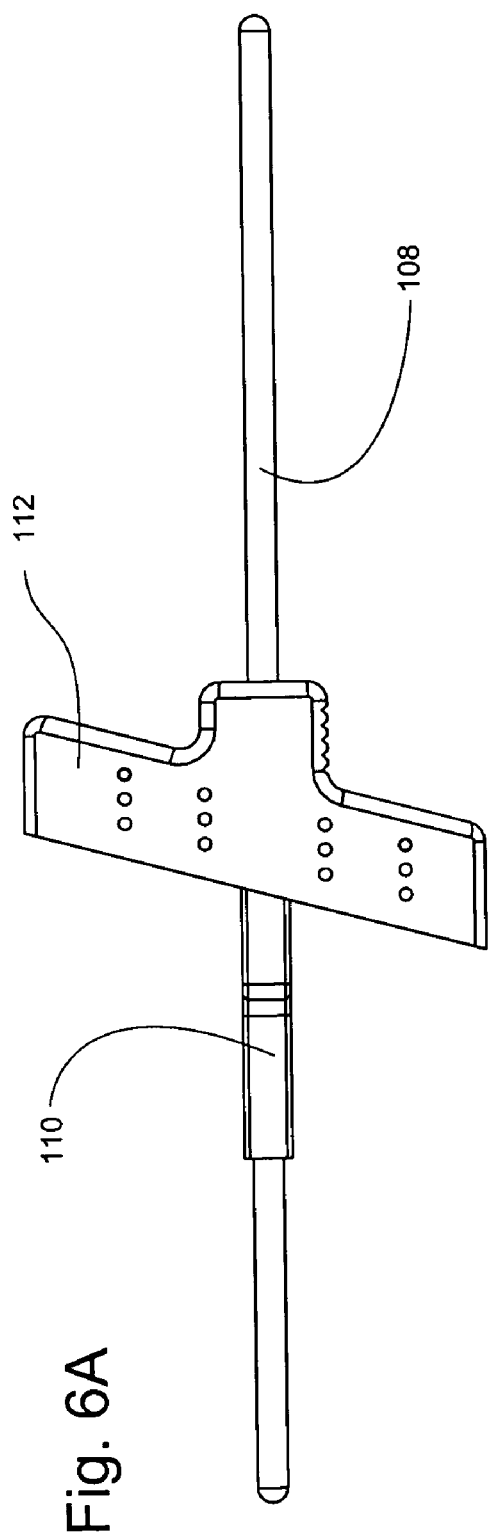
FIGS. 6A and 6B are a plan view and side elevation view of tools used for preparation of the radius in accordance with a method of the present disclosure.
Figure 6B:
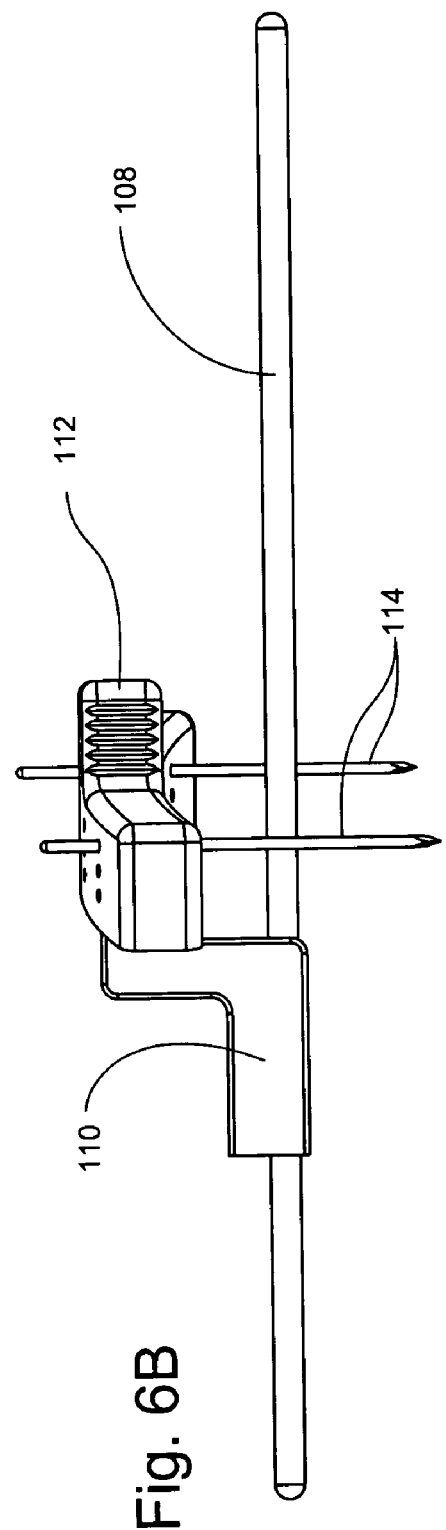

Referring now to FIGS. 6A and 6B, tools used to determine the correct angle and complete resection of the radial bone are shown. Radial alignment guide rod 108 is for insertion into the medullary canal of radius bone 12. Radial guide bar 110 is slid over radial alignment guide rod 108 and is used for placement of radial cutting block 112 over the distal end of radius bone 12. Once radial cutting block 112 is in the proper placement for resecting, K-wires 114 can be inserted through a series of 4 columns of holes in radial cutting block 112 to hold it in place. Each row of holes can have three holes to allow proximal relocation of the cutting guide. This is to permit additional parallel bone cuts at a distance of about 2.5 mm between each row of holes.

Figure 7A:
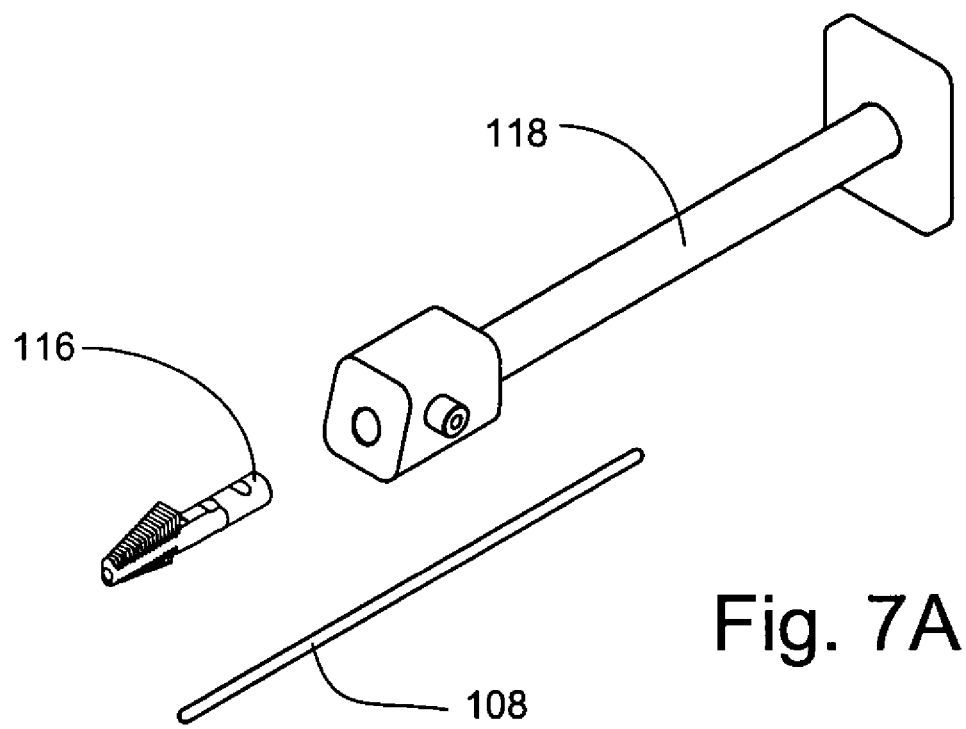
FIGS. 7A and 7B are perspective views of broaching tools used for preparation of the radius in accordance with a method of the present disclosure.
Figure 7B:
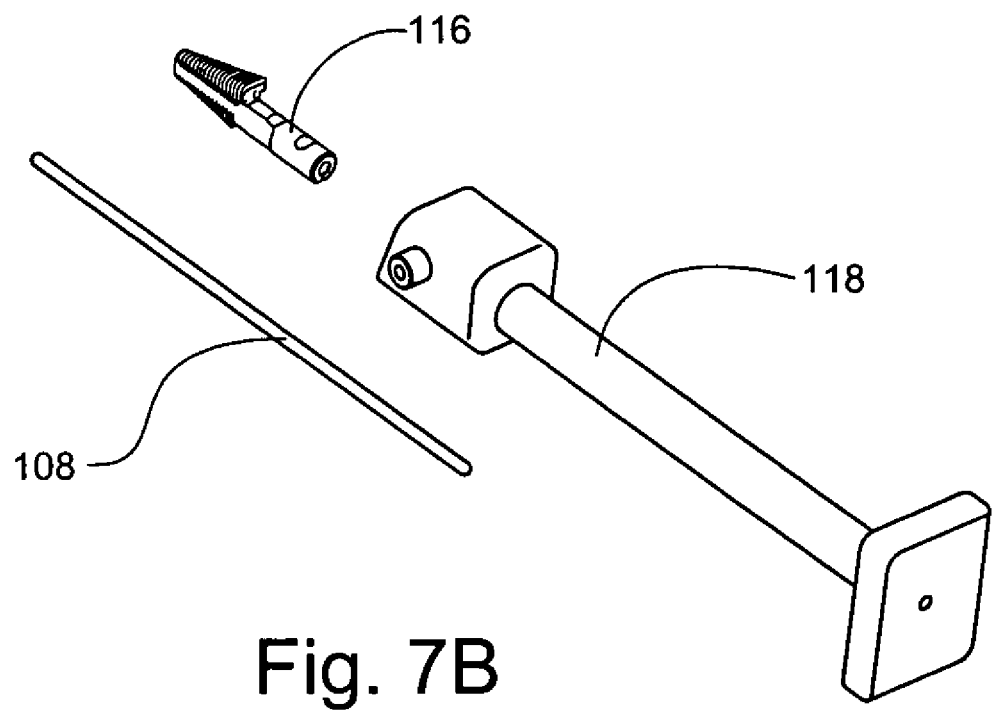

Referring now to FIGS. 7A and 7B, tools used to broach the radial bone for insertion of radial implant component 40 are shown. A proper size broach head 116 is selected depending on the size hole needed for insertion of the proper size radial implant component 40 (extra-small, small, medium, large). Broach head 116 is inserted into broach handle 118 and the resulting combination is slid over radial alignment guide rod 108 and abutted against the resected head of radius bone 12. A mallet (not shown) is used to drive broach head 116 into radius bone 12 to create the broach.

As described hereinabove, radial alignment guide rod 108 is entered into the distal radius and travels down the medullary canal of radius bone 12. This concentric alignment of guide rod with the intramedullary canal directs the optimal placement of radial broach head 116. Prior art prosthetic wrist implant methods included the placement of a radial component center stem in the center of the distal radius with no guide rod, which was preceded with the reaming of an unguided center broach hole that would sometimes impact the volar cortex wall and create cortex fracture. The anatomy of the distal radius is that the dorsal side remains uniform in thickness to the intramedullary canal while the volar cortex flairs out similar to a funnel to the volar surface with a thin bone cortex. Therefore, the novel combination of the use of a radial alignment guide rod 108 that guides broach head 116 with the axis-symmetrical and dorsal off-center radial stem 48 creates a radial implant component 40 that is directed for proper axial alignment and prohibited from possible volar cortex fracture.

Figure 8A:
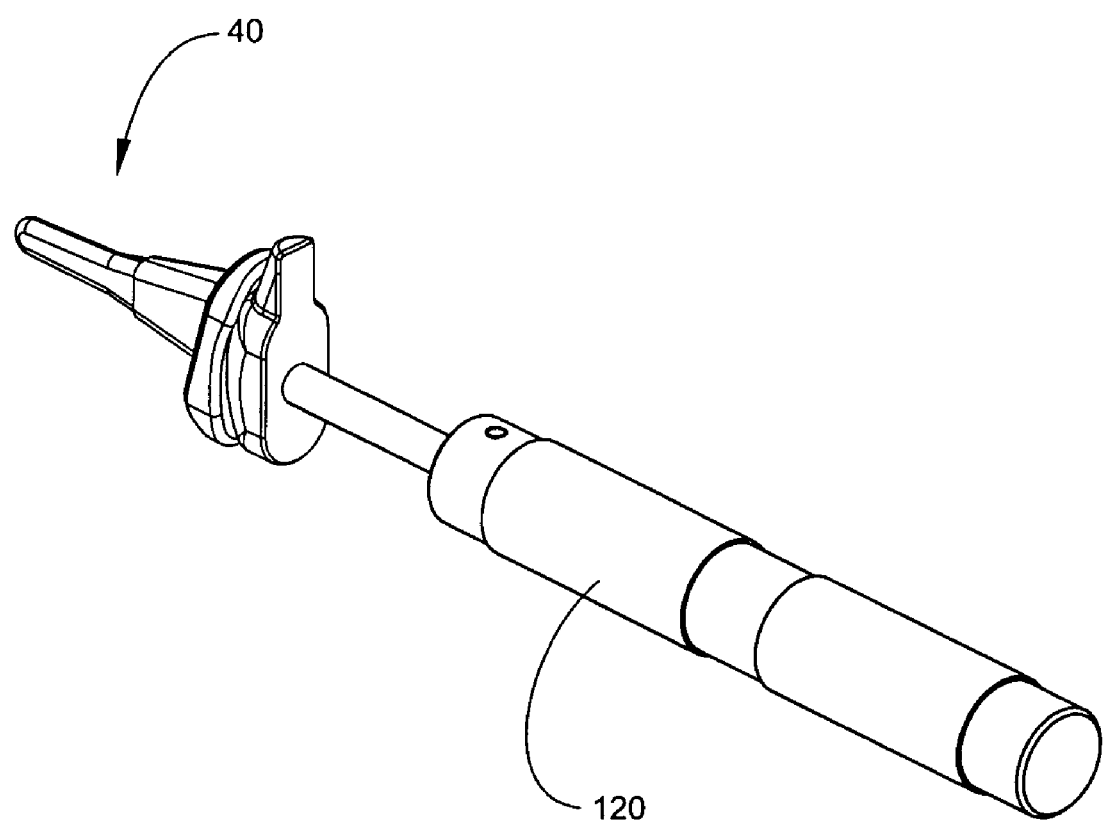
FIGS. 8A and 8B are perspective views of tools used for insertion and extraction of a trial radial implant component in accordance with a method of the present disclosure.
Figure 8B:
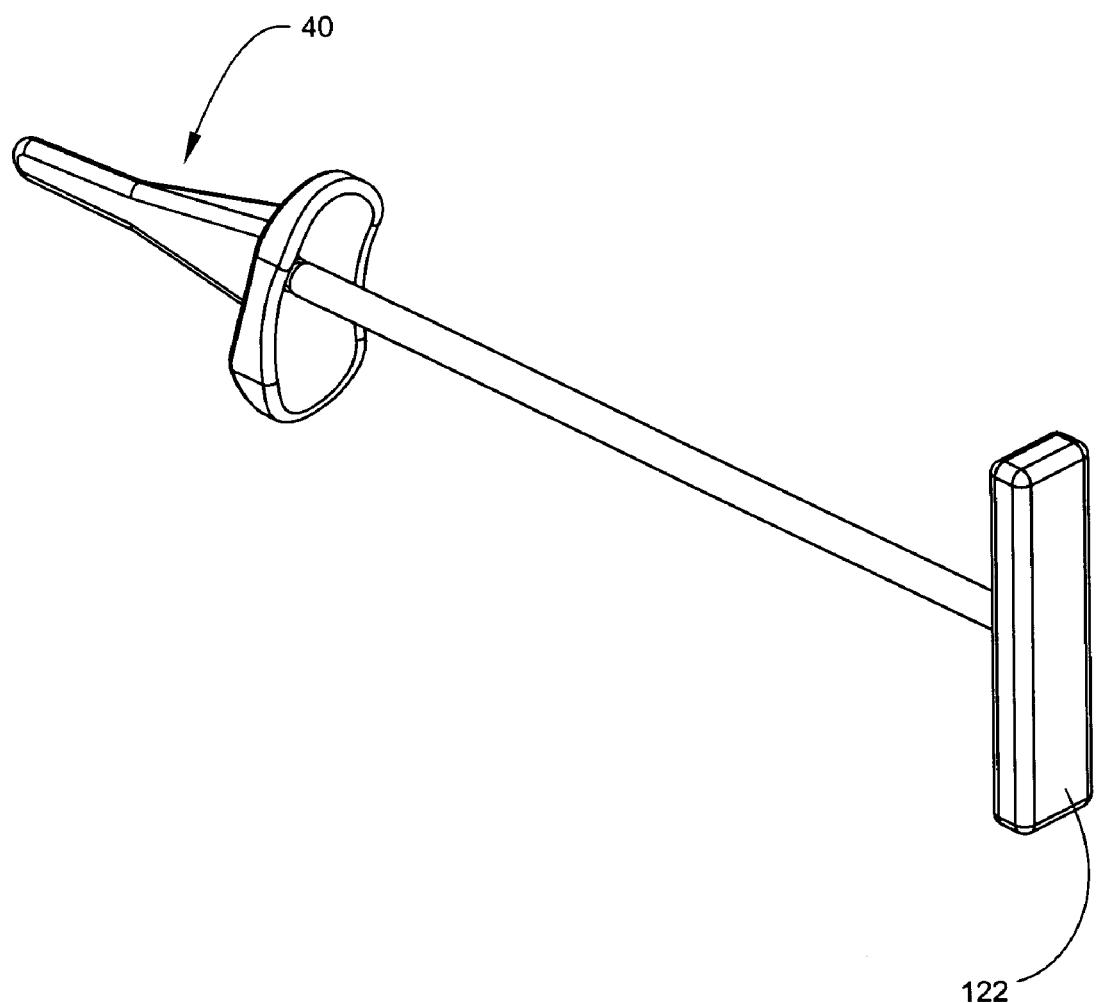
Figure 9A:
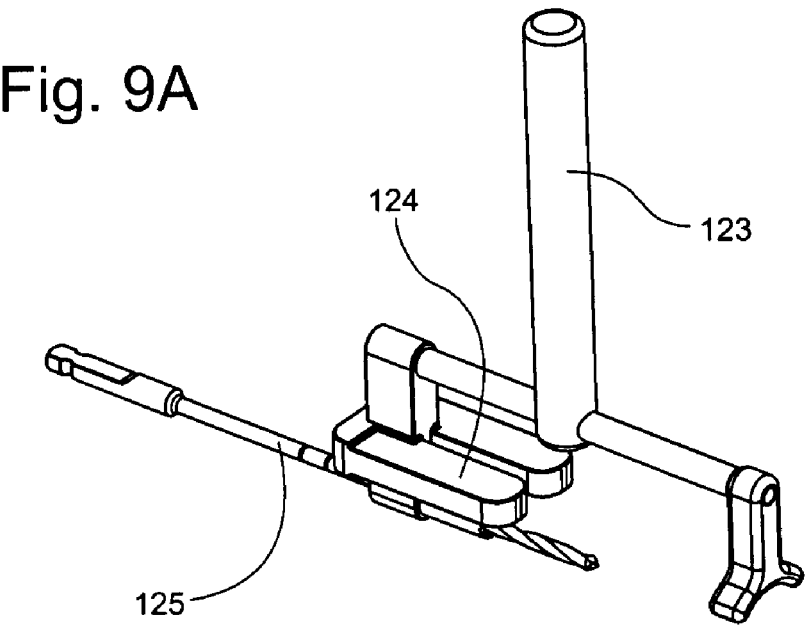
FIGS. 9A-9D are perspective views of tools used for preparation of the carpus in accordance with a method of the present disclosure.
Figure 9B:
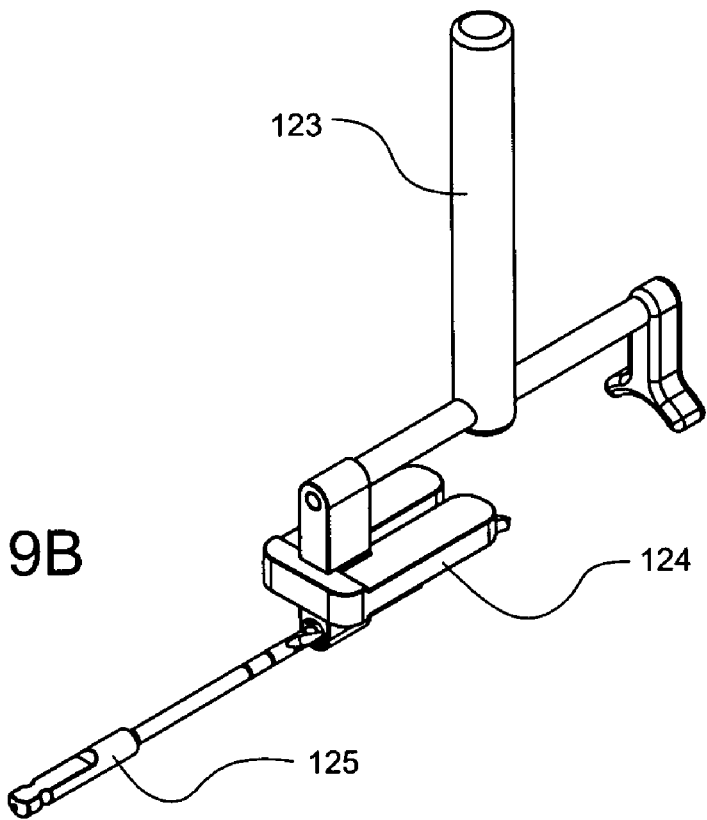
Figure 9C:
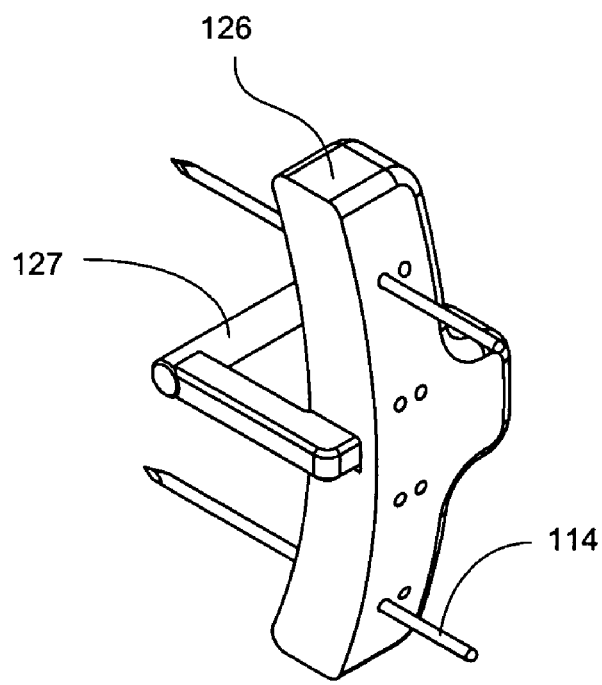
Figure 9D:
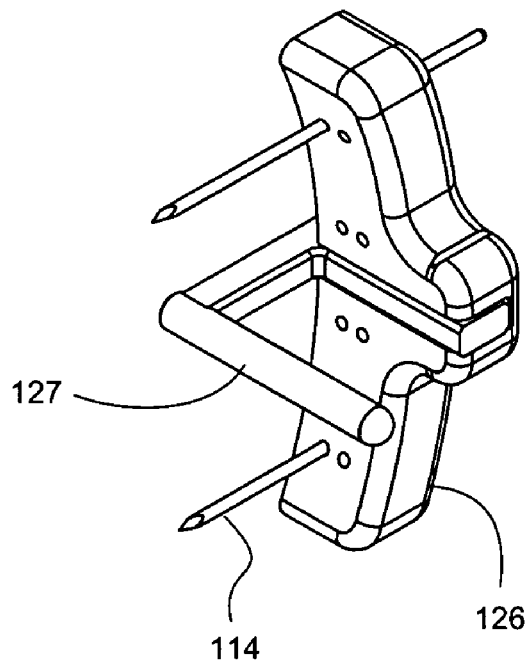
Figure 10A:
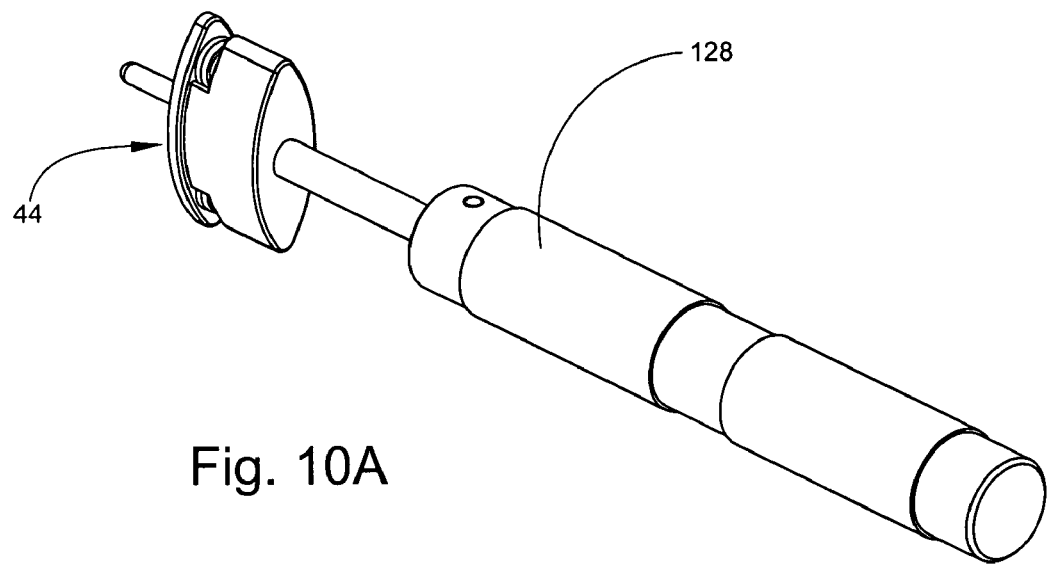
FIGS. 10A-10D are perspective views of tools used for insertion of a carpal implant component in accordance with the method of the present disclosure.
Figure 10B:
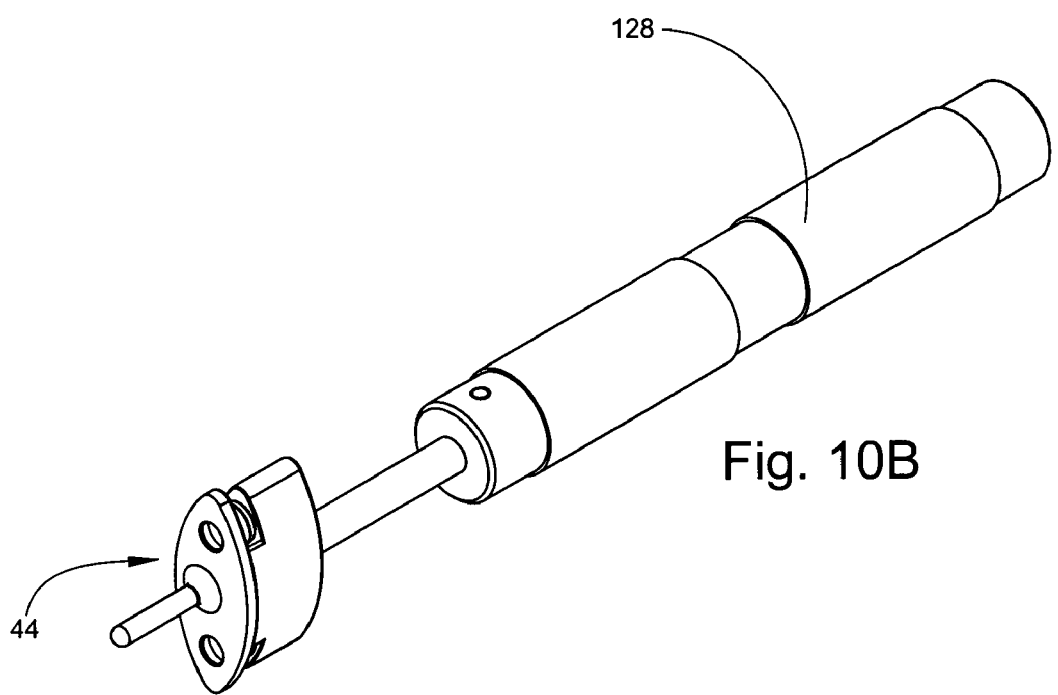
Figure 10C:
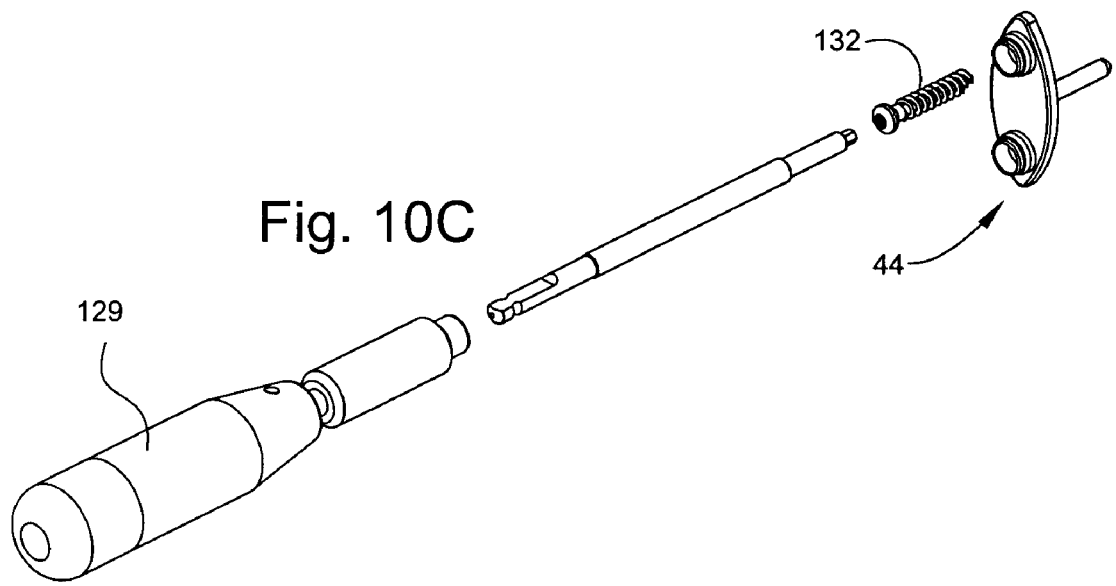
Figure 10D:
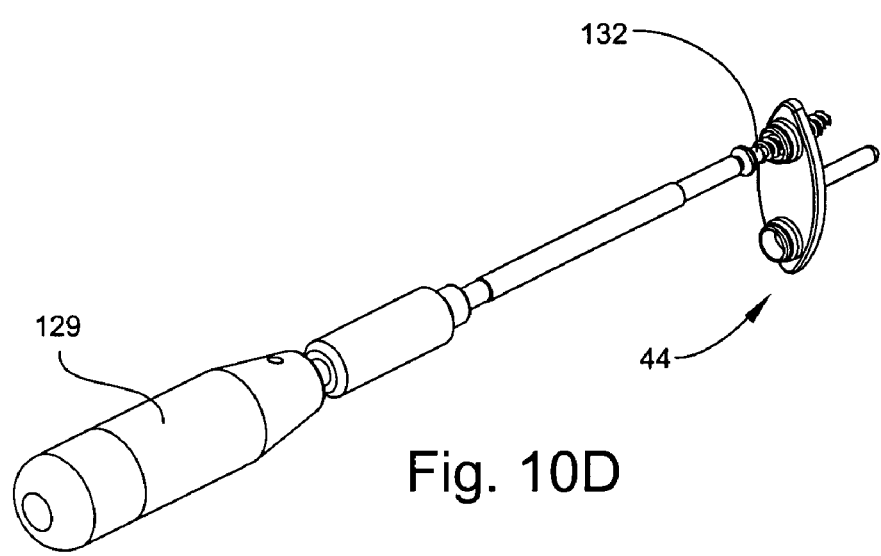
Figure 11A:
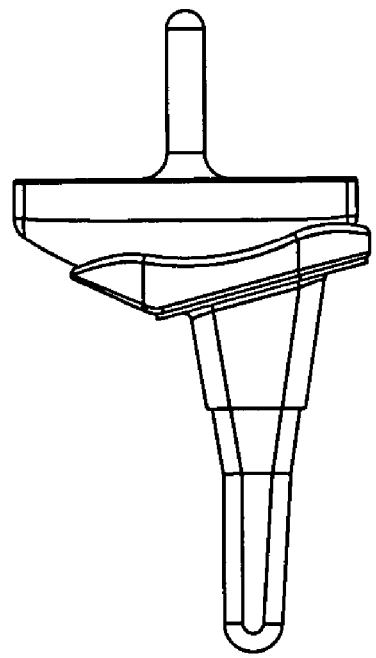
FIGS. 11A-11H show x-ray templates used for four sizes of the wrist implants.
Figure 11B:
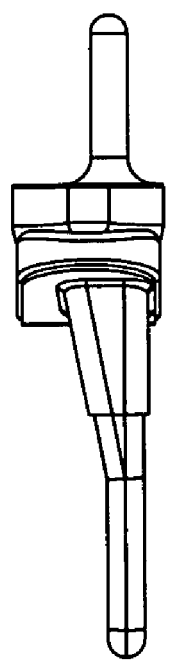
Figure 11C:
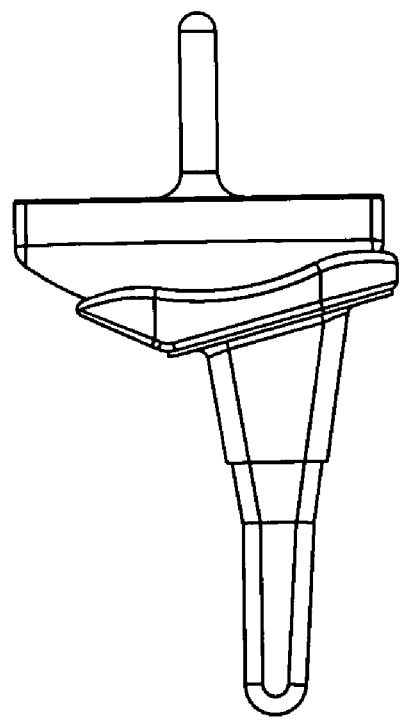
Figure 11D:
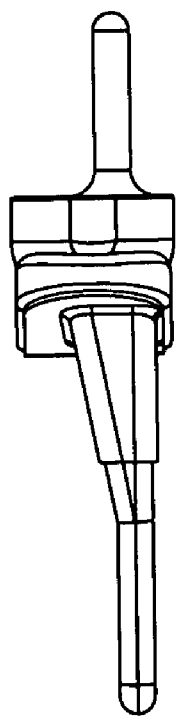
Figure 11E:
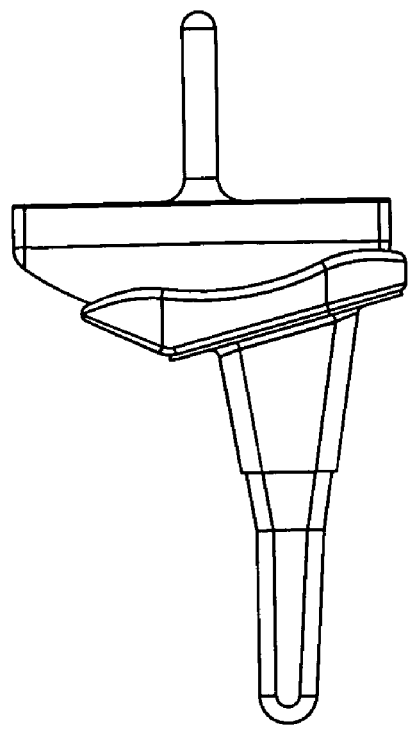
Figure 11F:
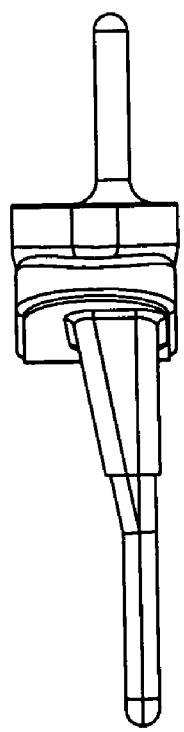
Figure 11G:
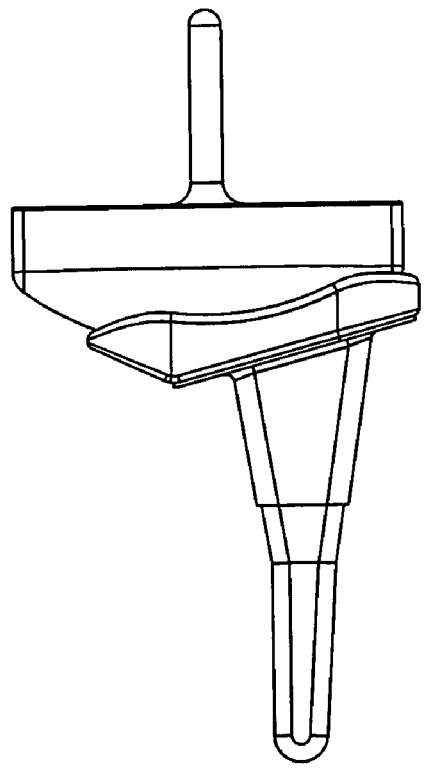
Figure 11H:
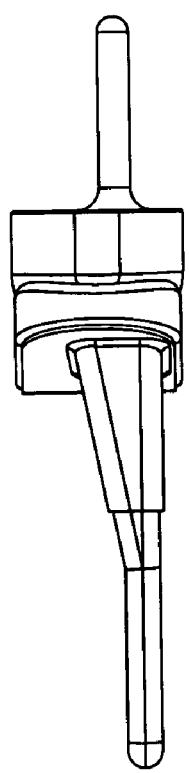

Referring now to FIGS. 8A and 8B, tools used to insert and extract trial versions of radial implant component 40 and insert the permanent radial implant component 40 into radius bone 12, are shown. Radial impactor 120 is designed to engage upper bearing surface 52 of radial implant component 40 as shown and drive radial component 40 into radius bone 12. If radial component 40 is to be removed, such as during trial runs prior to implantation of the permanent implant, radial T-handle extractor 122 can be used to matingly engage radial component 40 and extract the same out of radius bone 12. This mating engagement between radial T-handle extractor 122 and radial component 40 can be through threaded male and female portions or any other mating system known to those of skill in the art.

Referring now to FIGS. 9A-9D, tools used to determine the correct angle and complete resection of carpus bone complex 32, are shown. Carpal modular drill guide 123 and carpal modular drill guide plate 124 are used for positioning carpal drill bit 125 for production of a guide bar hole in the carpal capitate head. The yoke feature at the end of carpal modular drill guide 123 directs an axial alignment of carpal drill bit 125 to the opposite end of the drill bit guide hole. The Carpal modular drill guide 123 centers the axial alignment of the drill bit to drill to the center of metacarpal bones 34. Upon insertion of the guide hole, carpal guide bar 127 is inserted into the hole and carpal cutting guide block 126 is mounted onto carpal guide bar 127 and slid into proper position for resecting. Once carpal cutting guide block 126 is in the proper position for resecting, K-wires 114 can be inserted through holes in carpal cutting block 126 to hold it in place. Carpal cutting guide bar 127 can have a series of 4 columns of holes, two in each column, for relocation of the carpal cutting guide bar. This is to permit additional parallel bone cuts at a distance of about 2.5 mm between each row of holes.

Referring now to FIGS. 10A-10D, tools used to insert carpal implant component 44 into carpal bone complex 32, are shown. Carpal impactor 128 is designed to engage lower surface 70 of carpal implant component 44 as shown and drive carpal component 44 into carpal bone complex 32 for permanent fixation. Screwdriver 129 is used to insert bone screws 132 for complete fixation.

A surgical technique of implanting the prosthetic wrist implant WI will now be described in connection with FIGS. 11A-23.

FIGS. 11A-11H illustrate x-ray templets used in conjunction with prosthetic wrist implant WI to ensure proper sizing (for example extra-small, small, medium and large) of the implant prior to the surgical operation as discussed in more detail below. Extra-small, small, medium and large sizes of the implants are shown in two views in the x-ray template. Upon x-ray viewing, radial component 40 should not extend more than 2 mm over the margins of the carpus at the level of the osteotomy. In general, the surgeon should select the smaller implant size when deciding between two sizes.

Prior to performing the prosthetic wrist implant surgical procedure, the patient is placed under general or regional anesthesia. Alternatively auxiliary block anesthesia may be used. A non-sterile tourniquet is used to obtain a bloodless field. A strip of transparent adhesive film is applied to the dorsum of the hand and wrist to protect the skin from damage during instrumentation. Fluoroscopy is a helpful adjunct to confirm positions of the guides and implants. Save all resected bone during the procedure for use in bone grafting the carpus to achieve an intercarpal arthrodesis.

Figure 12:
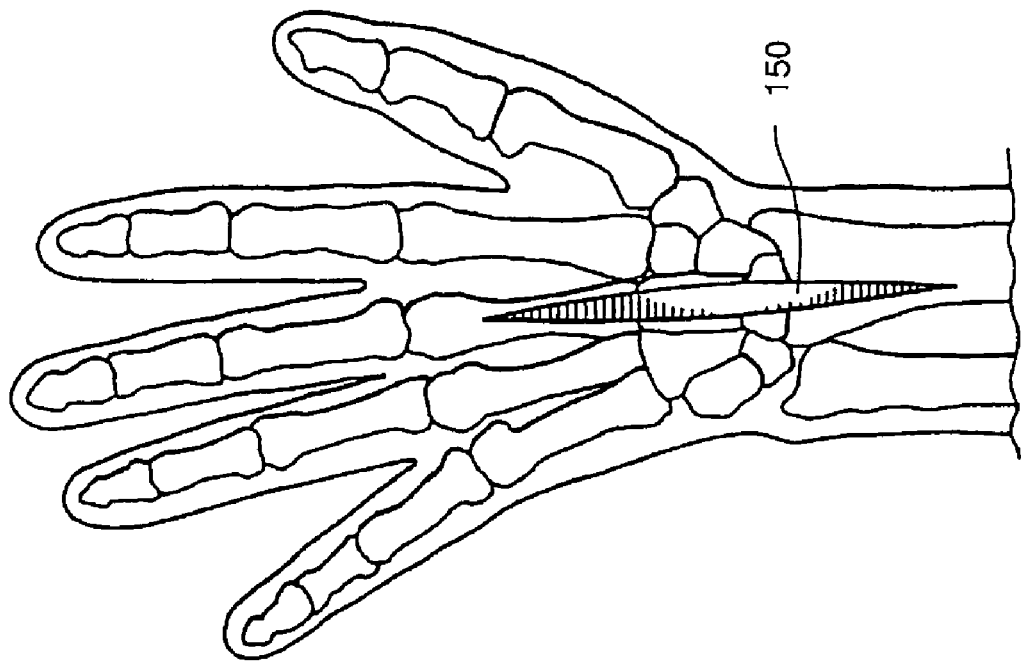
FIG. 12 is a phantom view of the left hand showing a surgical incision utilized in accordance with a method of the present disclosure.

Referring now to FIG. 12 a longitudinal dorsal incision 150 is made over the wrist along the line of the third metacarpal, extending proximally from its midshaft. Subcutaneous tissue and skin are elevated sharply from the extensor tendons and retracted medially and laterally using three zero silk retraction sutures, with care to protect the superficial radial nerve and the dorsal cutaneous branch of the ulnar nerve. The extensor retinaculum is opened over the fourth compartment and raised medially and laterally. A dorsal synovectomy is carried out and the wrist extensors are checked for structural integrity.

Figure 13:
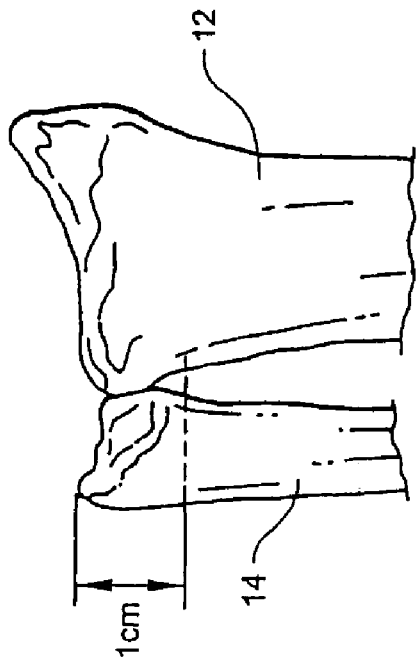
FIG. 13 is a phantom view of radius and ulnar bones showing ulnar resection.

To perform the ulnar head resection, which may be necessary to create a larger flap for closure over the prosthesis, the capsule over distal ulna 14 is opened longitudinally. As shown in FIG. 13, the distal one centimeter of the ulna 14 can be osteotimized and removed. A synovectomy of the ulnar compartments is then performed.

Figure 14A:
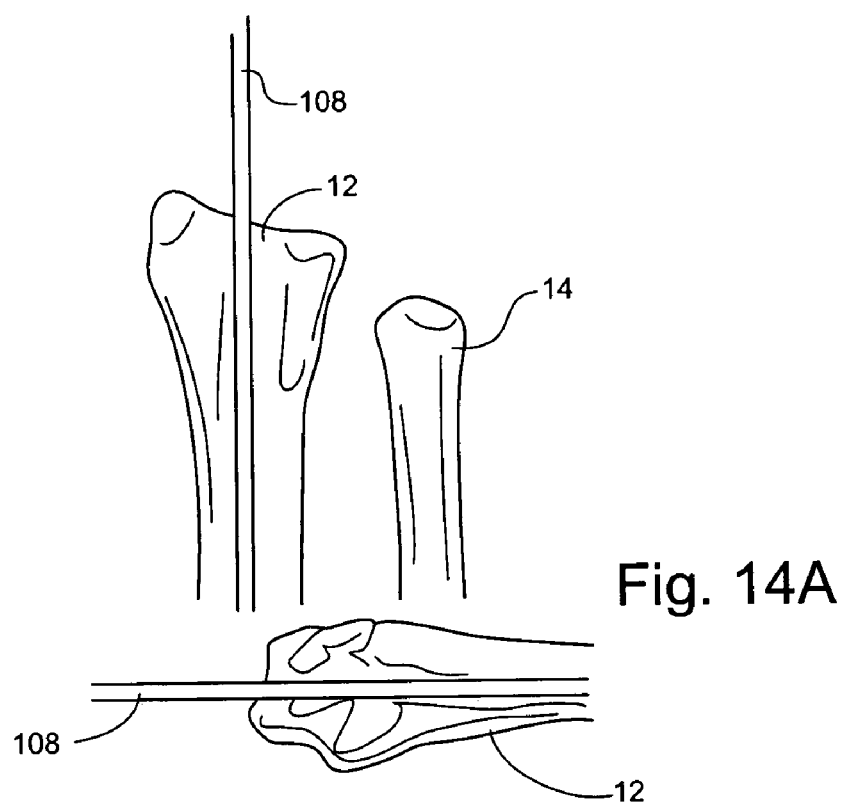
FIGS. 14A-14C are perspective views showing radius preparation.
Figure 14B:
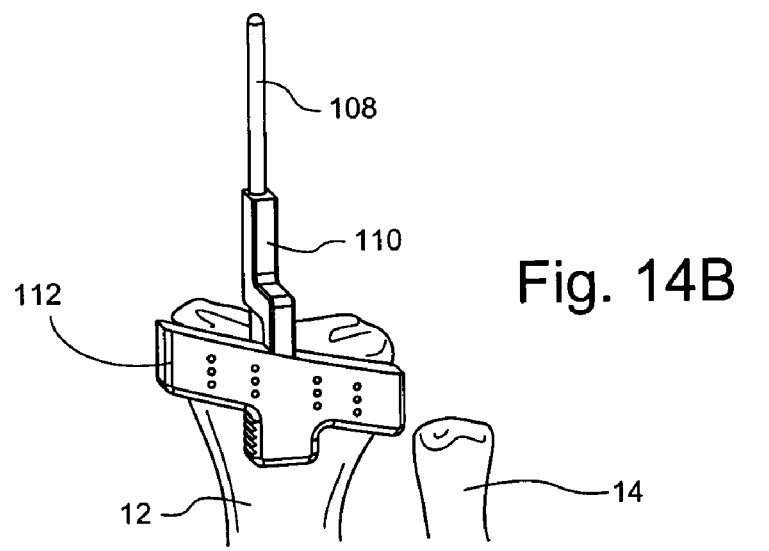
Figure 14C:
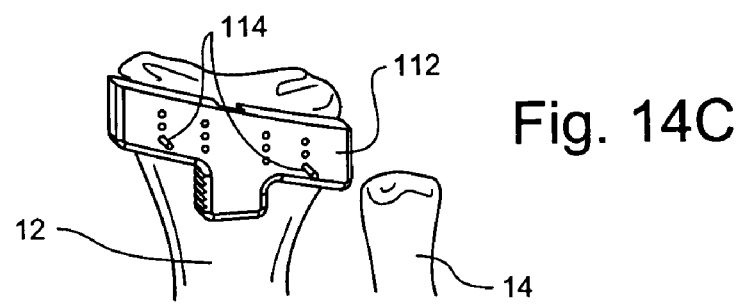

Referring now to FIGS. 14A-15B, preparation of radius bone 12 will now be described. Using a bone awl (not shown), a hole is made through the articular surface of radius 12 about 5 mm below its dorsal rim and just radial to Lister's tubercle. Enlarge the hole with a curette. Radial alignment guide rod 108 is inserted in the hole and advanced far into the medullary canal (FIG. 14A). Fluoroscopy may be used to confirm that guide rod 108 is centered within the canal. Radial guide bar 110 is slid over the rod until it abuts the radius. Radial cutting guide block 112 (left or right) is mounted onto guide bar 110 and slid into proper position. It is positioned to guide the saw cut just beneath the articular surface (FIG. 14B). While the curved under-surface of cutting block 112 is held aligned with the dorsal surface of radius bone 12, two or three 1.1 mm K-wires 114 are inserted through the holes in cutting block 112 and drilled into the distal end of radius bone 12. Cutting block 112 preferably has four rows of three holes spaced about 2.5 mm apart. By using the middle holes in the rows, cutting block 112 can be adjusted proximally or distally if the initial position was incorrect (FIG. 14C).

Alignment rod 108 and guide bar 110 are removed and cutting block 112 is slid down along K-wires 114 against radius 12. Lister's tubercle may have to be removed to fully seat the cutting block. K-wires 114 are cut a few millimeters above cutting block 112. The position of cutting block 112 is checked for proper level of resection and adjusted if needed. A small oscillating saw (not shown) is used to make the radial osteotomy. To complete the cut through the volar cortex, cutting block 112 may have to be removed. Cutting block 112 and K-wires 114 are removed.

Referring now to FIGS. 15A and 15B, the broaching of radius bone 12 will now be described. Alignment rod 108 is reinserted into the hole in radius bone 12. The proper size broach head 116 is inserted into broach handle 118 to the position for either "standard" or "minimal" broaching. Broach head 116 is slid over alignment rod 108 and its ulnar face is aligned parallel to the sigmoid notch of radius bone 12 (FIG. 15A). Using a mallet, broach head 116 is driven into the distal radius 12 until its collar is flush with the cut surface of radius 12 (FIG. 15B). Broach head 116 and alignment rod 108 are removed.

In order to determine the proper final implant size, a trial radial component 40 is inserted into radius bone 12 using the radial impactor 120, with care to maintain proper alignment within the prepared metaphysis. The radial T-handle extractor tool 122 is applied and trial radial component 40 is removed.

Referring now to FIGS. 16A-18B, preparation of carpus bone complex 32 will now be described. If scaphoid 16 and triquetrum 20 are mobile, carpus preparation is facilitated by first temporarily pinning these bones to capitate 24 and hamate 22 bones in their best-reduced positions. K-wires are inserted through their distal portions just beneath the dorsal cortices to avoid interfering with the osteotomy and the insertion of the carpal component implantation. Lunate 18 is excised by sharp dissection or rongeur.

Figure 16A:
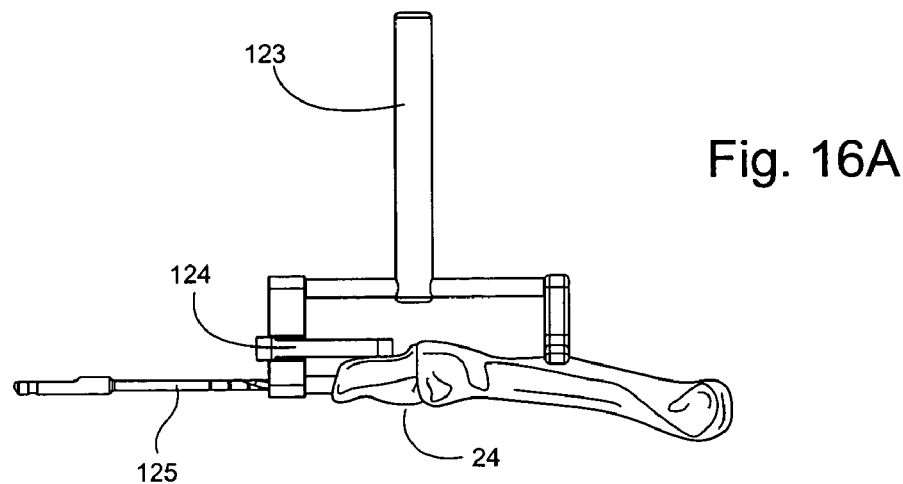
FIGS. 16A and 16B are perspective views showing initial carpus preparation.
Figure 16B:
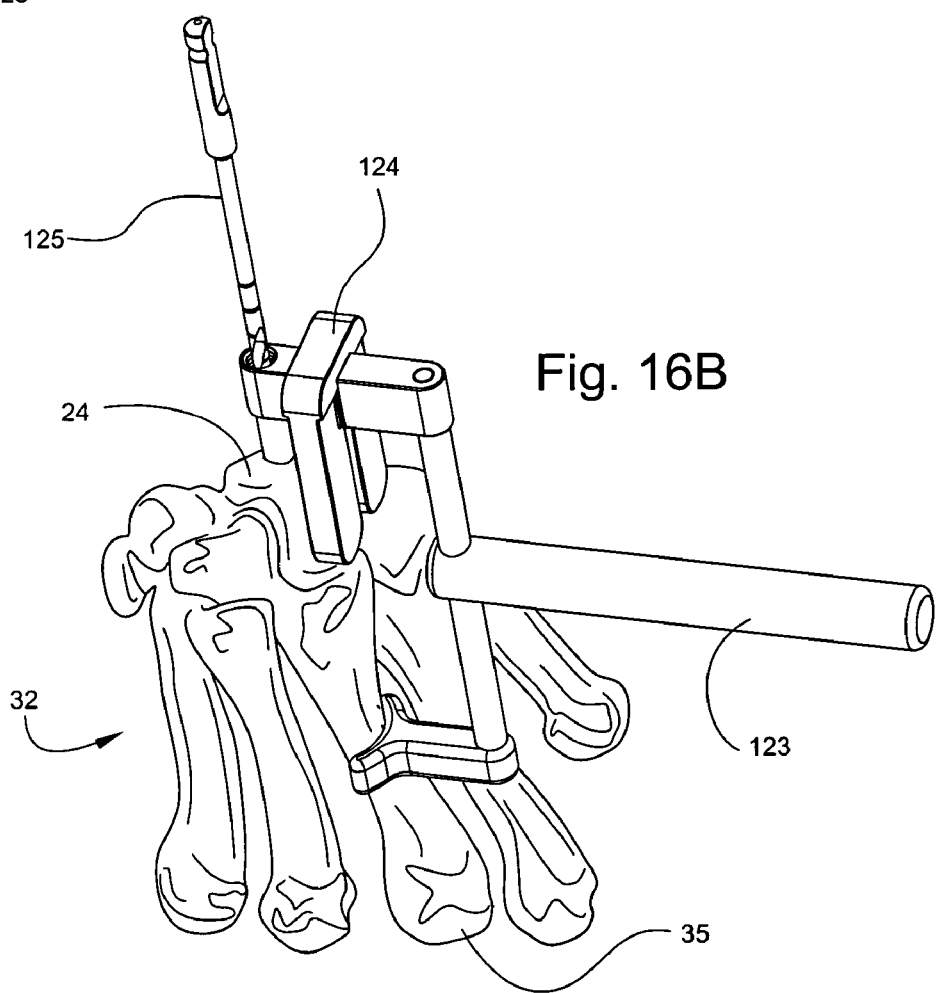

Referring now to FIGS. 16A and 16B, carpal modular drill guide plate 124 corresponding to the selected implant size is inserted into carpal modular drill guide 123. In applying drill guide 123, guide plate 124 is rested on the dorsum of capitate 24, the barrel is pressed against the capitate head, and the saddle is placed onto the $3^{rd}$ metacarpal shaft 35 over the skin. For a "minimal" hole diameter for carpal component post 50, the 2.5 mm drill bit is preferably used. While firmly holding drill guide 123, carpal drill bit 125 is inserted into the barrel and a hole is made in capitate 24 to the depth marked on the bit corresponding to the implant size (x-small-16 mm, small-18 mm, medium-20 mm, large-22 mm). The counter-sink is used to enlarge the opening of the hole to accommodate the "shoulder" of the implant stem. For a "standard" hole diameter for carpal component post 50, the sleeve for the guide wire is inserted in the drill guide barrel. The 1.4 mm guide wire is drilled through capitate 24 and into the $3^{rd}$ metacarpal. The sleeve and drill guide are removed sequentially. The 3.5 mm cannulated drill is placed over the guide wire and a hole is made in capitate 24 to the proper depth corresponding to the implant size. The counter-sink is used to enlarge the opening of the hole.

Figure 17A:
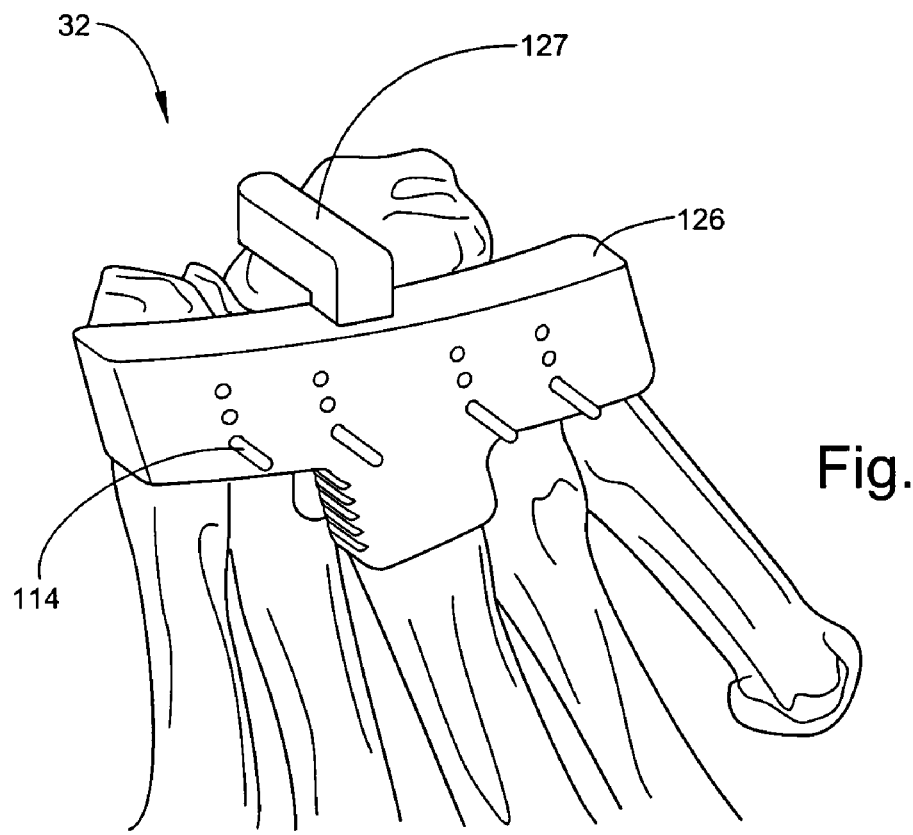
FIGS. 17A and 17B are perspective views showing carpus resecting.
Figure 17B:
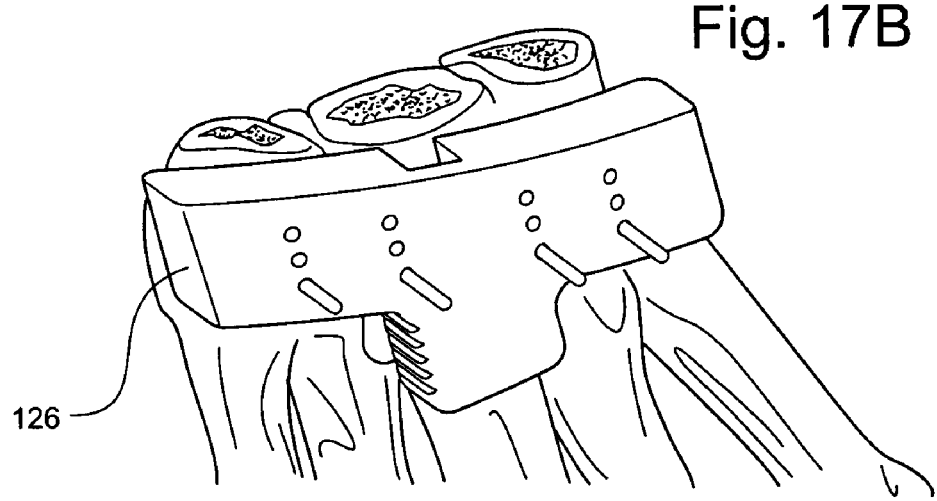

Referring now to FIGS. 17A and 17B, the appropriate carpal guide bar 127, for either a standard or minimal hole diameter, is inserted into the capitate hole, drilled as described above, to its full depth. Carpal cutting guide block 126 is mounted onto guide bar 127 and slid into proper position. It is positioned to guide the saw cut through the proximal 1 mm of hamate 22, which will pass through the capitate 24 head, scaphoid 16 waist, and mid-body triquetrum 20. While the curved under-surface of the cutting block is held aligned with the dorsal surface of the carpus 32, two to four 1.1 mm K-wires 114 are inserted through the holes in cutting block 126 and drilled into the carpus. Carpal cutting block 126 preferably has four rows of two holes spaced about 2.5 mm apart. By using the distal holes in the rows, cutting block 126 can be adjusted distally to resect more carpus if the initial position is incorrect.

K-wires 114 are cut a few millimeters above cutting block 126. The position of cutting block 126 is checked for proper level of resection and to confirm that the cut will be made nearly perpendicular to the $3^{rd}$ metacarpal shaft. A small oscillating saw (not shown) is used to make the carpal osteotomy (FIG. 17B). To complete the cut through the volar cortices cutting block 126 may have to be removed, but K-wires 114 should be retained. Cutting block 126 can be reapplied to help stabilize the carpal bones during the remaining carpal preparation.

Referring now to FIGS. 18A and 18B, in order to determine the proper final implant size, a trial carpal implant component 44 is inserted into the capitate hold and its dorsal edge is aligned with the dorsal surface of the carpus. Carpal modular drill guide 123 (without the drill guide plate) is applied with its barrel in the radial hole of carpal component 44 and its saddle on the $2^{nd}$ metacarpal shaft 33 over the skin. A 2.5 mm hole is drilled across the scaphoid, trapezoid, and $2^{nd}$ CMC joint to a depth (marked on the drill bit) of 30 to 35 mm (FIG. 18A). This hole is typically not perpendicular to the carpal component, however the component and screws heads are designed to accommodate screw insertions at oblique angles (see FIGS. 4E and 4F above). A 4.0 mm self-tapping trial screw 132 is inserted but not firmly tightened (FIG. 18B).

A similar technique is used for the ulnar trial screw insertion, with a few important differences. The saddle is placed on the $4^{th}$ metacarpal shaft 37 over the skin. The $4^{th}$ metacarpal must be held elevated ($4^{th}$ CMC extended) while drilling to ensure the hole is not directed volarly. The hole is drilled across the triquetrum and into the hamate but does not cross the mobile $4^{th}$ CMC joint. Its depth is typically 20 mm but a small wrist may accommodate only 15 mm. A 4.0 mm self-tapping trial screw is inserted but not firmly tightened.

Figure 19:
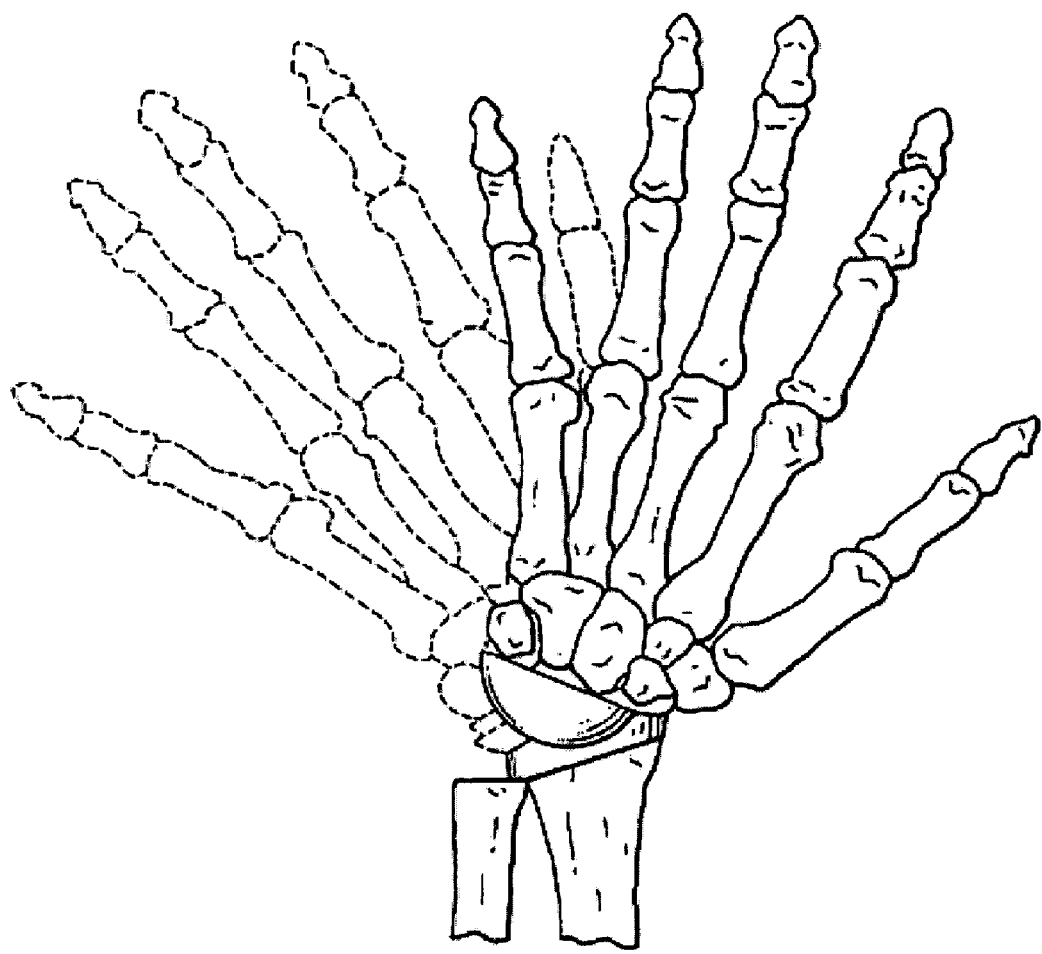
FIG. 19 is a perspective view of the bones of the left hand with a trial wrist implant in place showing range of motion of the wrist.

A trial reduction is then performed to verify all proper sizing of components prior to final implantation. Radial trial implant component 40 is reinserted into the medullary canal of radius bone 12. A trial carpal bearing component 42 is slid over the carpal plate, beginning with the standard thickness, and the joint is reduced as shown in FIG. 19 so that the range of motion and stability can be checked. The prosthesis is typically quite stable and should demonstrate approximately 35° of flexion and 35° of extension with modest tightness at full extension. If the volar capsule is tight and limiting extension, the radius may need to be shortened and re-broached using the previously described technique. If a preoperative flexion contracture was present, a step-cut tendon lengthening of the flexor carpi ulnaris and occasionally the flexor carpi radialis may be required to achieve proper balance and motion. When volar instability is present, the volar capsule is inspected and if detached it is repaired to the rim of the distal radius. If the volar capsule is intact, a thicker polyethylene component may be required to increase soft tissue tension. A mild dorsal instability should respond to capsule closure but a thicker polyethylene is considered for marked instability. The wrist should easily stay in neutral position or in the balance state.

When performing a trial reduction, an alternative to the procedure described immediately above is to use a trial set comprising a trial carpal implant component, a trial radial implant component, and a trial radial implant component that are identical to the implant components which will be permanently implanted during the implant procedure. However, the trial set has the advantage of sizing nine different trial carpal bearings during the trial process. After trial carpal component 44 and trial radial component 40 have been positioned, a trial bearing component 42 is slid over the carpal plate and the joint is reduced as shown in FIG. 19. If the joint is too tight, the first bearing component is removed and a second trial bearing component is inserted, the second bearing component being of either an increased dimension or a decreased dimension depending upon the results of the trial reduction. The trial bearing component can be made of an acetyl copolymer, a composite material, or any material having similar characteristics. The trial carpal implant component is preferably made of titanium and the radial implant component is preferably made of a cobalt-chrome material. However, the carpal implant component or the radial implant component may be made of any material having similar characteristics, such as a composite material.

An advantage to using the trial set during a trial reduction is that the size of the bearing component may be precisely selected for the particular implant being performed. This eliminates the necessity of having to remove additional bone from the radial bone in order to achieve a proper fit of the implant. Another advantage of using the trial set during the trial reduction is that the trial set may be reused after proper sterilization has been performed. Sterilization may include autoclaving or any sterilization method that would not dimensionally or physically affect the trial set.

Once a trial reduction is completed and the proper size implant decided upon, implantation must be performed in order to fixate the various components. Remove the trial components and irrigate the wound thoroughly. Three horizontal mattress sutures of 2-0 polyester are placed through small bone holes along the dorsal rim of the distal radius for later capsule closure. If the ulnar head was resected, sutures are placed through its dorsal neck.

Figure 20:
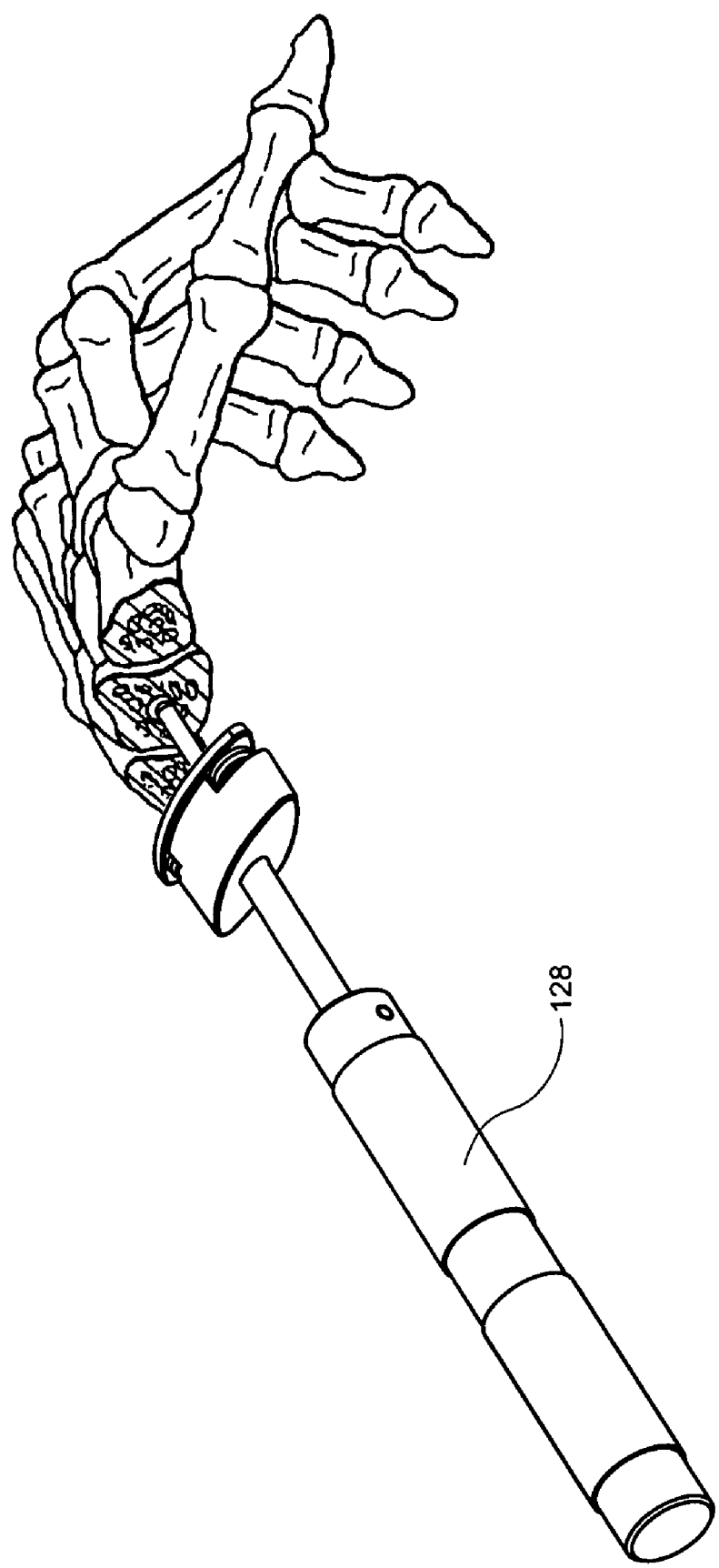
FIG. 20 is a perspective view of bones of the left hand illustrating fixation of the carpal component.

Next, carpal implant component 44 fixation is performed. First the wound is irrigated with pulsed lavage. Bone cement is introduced into the central peg hole in the capitate metacarpal complex. For example, in accordance with one embodiment this bone cement comprises methylemethacrylate. Carpal implant post 50 is introduced into this hole and tapped all of the way in as shown in FIG. 20 utilizing carpal plate impactor 128. It is important to keep the implant flush with the bone margins. Care must be taken to remove excess cement, especially from the intracarpal region. It is also understood that carpal component fixation may also be performed without the use of bone cement wherein carpal implant post 50 is press-fit or interference fit into the central peg hole in the capitate metacarpal complex through the use of an application of a beaded porous coating as described hereinabove.

The ulnar side of the plate is then drilled with a 2.5 millimeter bit. Two 4.5-millimeter screws 132 are then inserted through the peripheral holes in carpal planar base member 49. The radial screw is longer and could cross the carpal space mediocarpal joint. Since the carpal mediocarpal joint of the fourth and fifth metacarpals are mobile, care should be taken to avoid crossing these joints (unless it is necessary for better purchase). Screws 132 help hold the fragment of the triquetrum and the scaphoid in place and add strength to the carpal fixation. Bone screws 132 shown in FIG. 23 secure the hamate 22 and trapezoid 26, 28 bones respectively. These bone screws may comprise, for example, conventional 4.5-millimeter diameter bone screws that are between 20 and 40 millimeters in length depending on the size of the implant and patient. Remove any remaining K-wires from the carpus. Cancellous bone graphs obtained from the radius and resected carpal bones are packed into the defects between the carpal bones to obtain a uniform bony fusion.

Figures 21A, 21B:
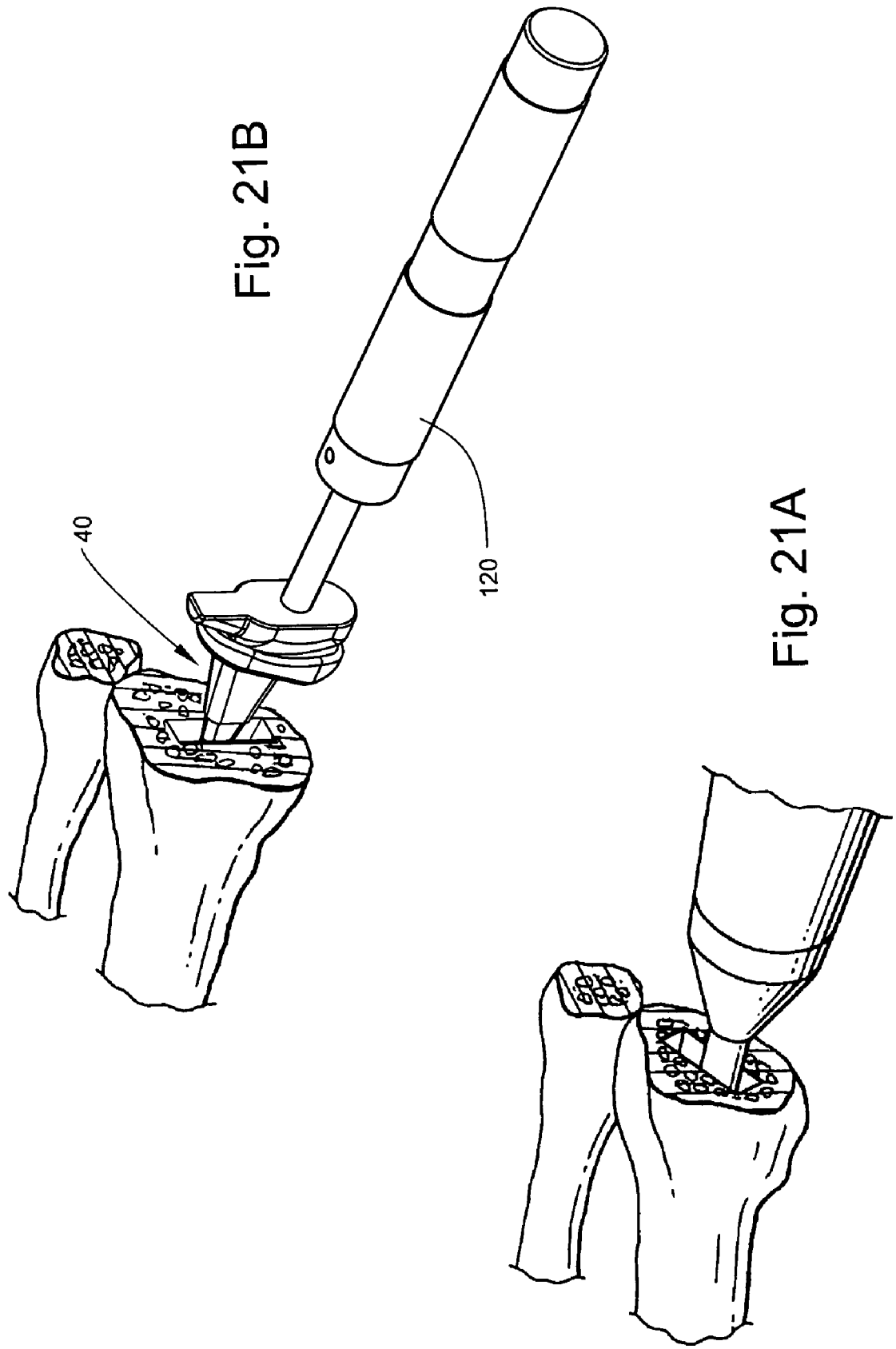
FIGS. 21A-21B are perspective views of the radius and ulnar bones illustrating a method of fixation of the radial component.

To perform radial implant component 40 fixation, a bone plug is inserted into the medullary canal of the radius to act as a cement restricter. The canal is cleaned with pulse lavage and dried. Bone cement is mixed and injected into the canal using a syringe as shown in FIG. 21A. The true radial component 40 is then introduced into the medullary canal as shown in FIG. 21B and is driven into the metaphysis using radial impactor 120. It is important to remove all excess cement from the immediate area. Care is taken to place the prosthesis in a valgus position. A varus angle of the component will result in a post-operative ulnar deviation deformity of the hand. It is also understood that radial component 40 fixation may also be performed without the use of bone cement wherein radial component stem 48 is press-fit or interference fit into the medullary canal of the radius through the use of an application of a beaded porous coating as described hereinabove.

The articulating bearing component 42 trial is applied to confirm the proper size. Once the correct size is verified, the bearing impactor (not shown) is placed over bearing component 42 and a firm impact is applied from a mallet in a linear motion. Bearing component 42 will snap into place when external lip 80 of socket protrusions 72 on carpal implant component 44 matingly join internal groove 106 of socket recesses 104 on bearing component 42. Then, bearing component 42 should be confirmed as completely engaged onto the carpal planar base member. A final assessment of wrist motion, balance and stability can then be made.

Wound closure is accomplished by first closing the ulnar joint capsule tightly, thereby stabilizing the distal ulnar. The ECU tendon is brought dorsally to obtain additional stability. The capsule of the radial carpal joint is reattached to the distal end of the radius. If the capsule is deficient, one-half of the extensor retinaculum is used to cover the defects. Meticulous closure of the capsule is mandatory to ensure stability in the post-operative. The hand is then immobilized in bulky dressing with the wrist in a neutral position for about two to three days.

Post-operative management initially involves strict elevation and early passive and active digital motion to reduce swelling. At approximately 10 days, the sutures are removed and an x-ray is obtained to confirm prosthetic reduction. A removable plastic wrist splint is fabricated and used when not performing exercises. A gentle wrist exercise program can begin within the first two weeks, including active flexion and extension, radial and ulnar deviation, and pronation and supination. A therapist may be engaged to ensure progress. The splint is discontinued at the $4^{th}$ postoperative week and hand use advanced. The exercise program is continued and strengthening is added. Power grip and lifting is discouraged for the first 8 weeks. A dynamic splint is occasionally used if recovery of motion is difficult or incomplete. The patient is advised against impact loading of the wrist and repetitive forceful use of the hand.

Figure 23:
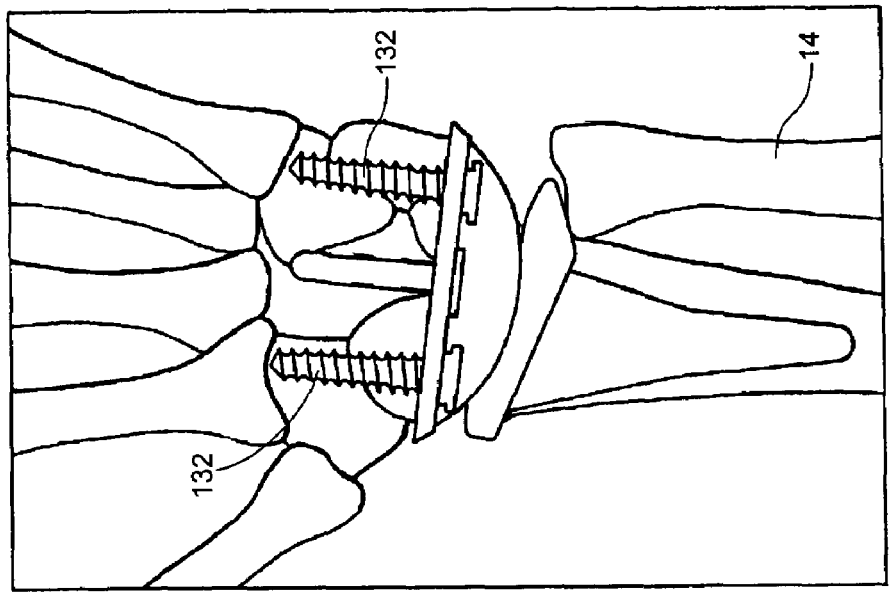
FIG. 23 is an x-ray of the patient's wrist shown in FIG. 22 at 32 months post-operative.
Figure 22:
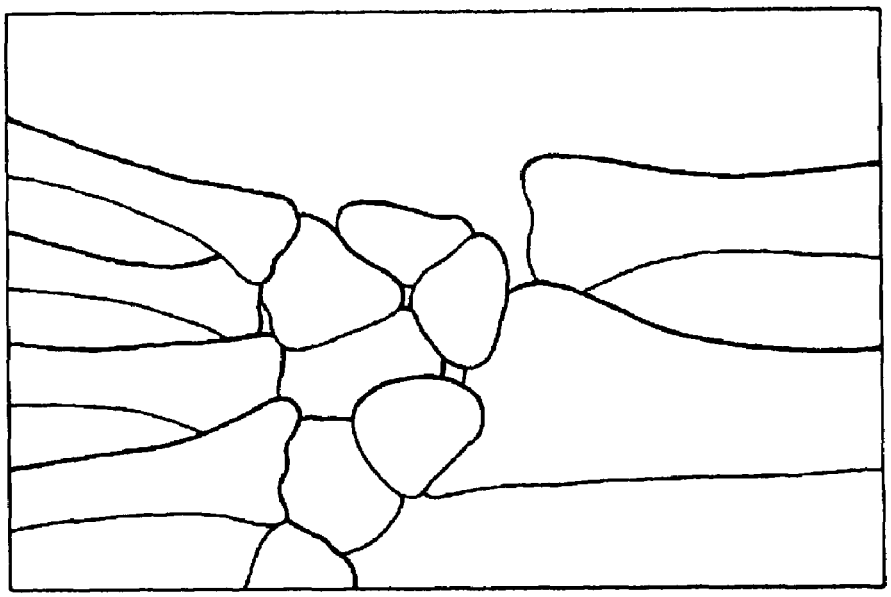
FIG. 22 is a pre-operative x-ray of a patient suffering from radio-carpal arthritis.
Figure 24:
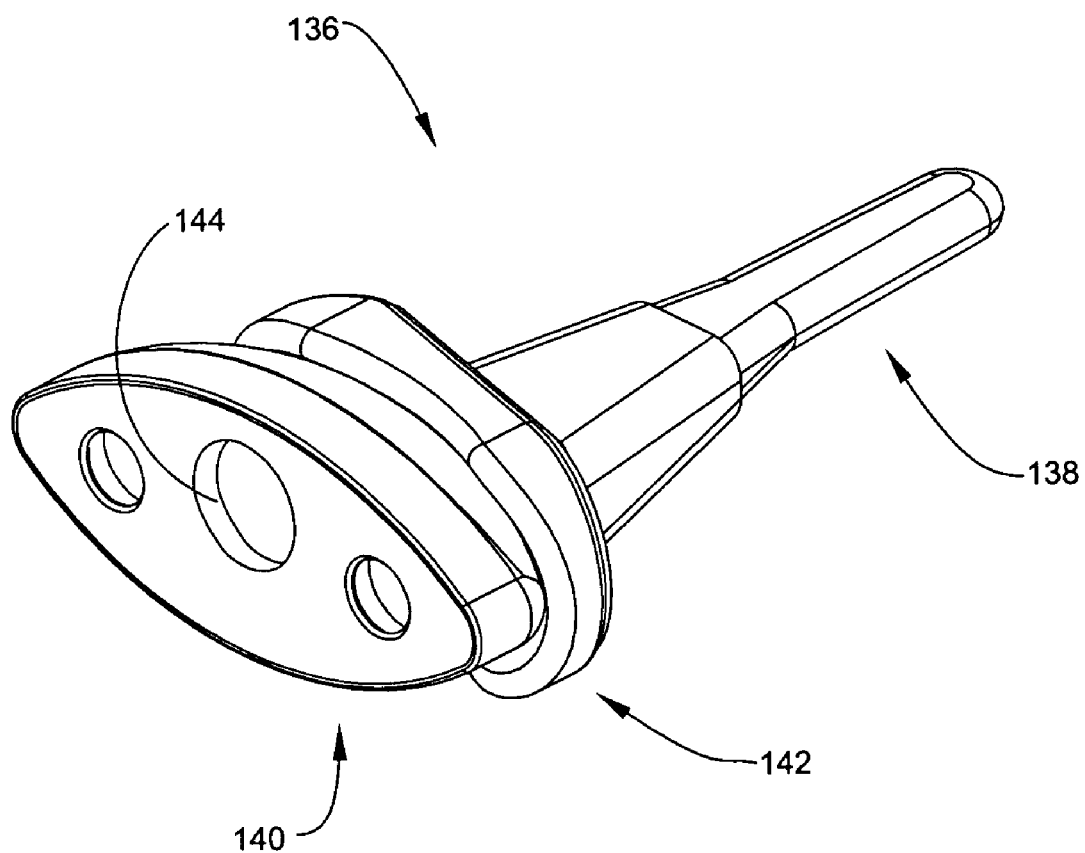
FIGS. 24-30 are various views of a wrist implant apparatus in accordance with an alternative embodiment of the present disclosure.
Figure 25:
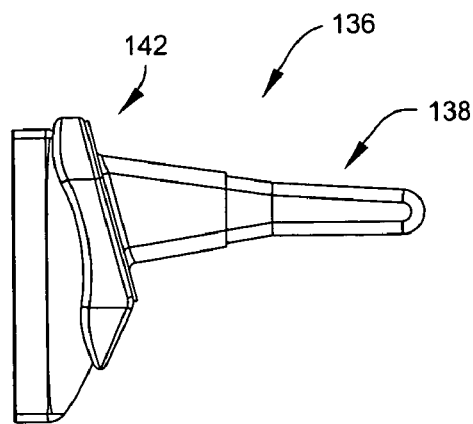
Figure 26:
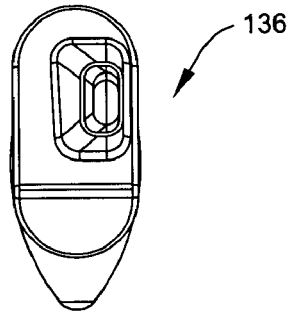
Figure 27:
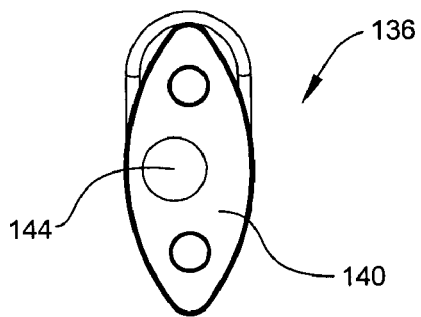
Figure 28:
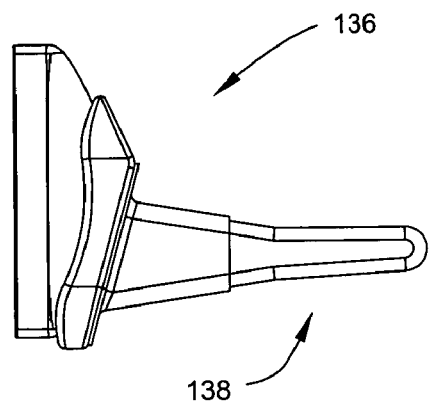
Figure 29:
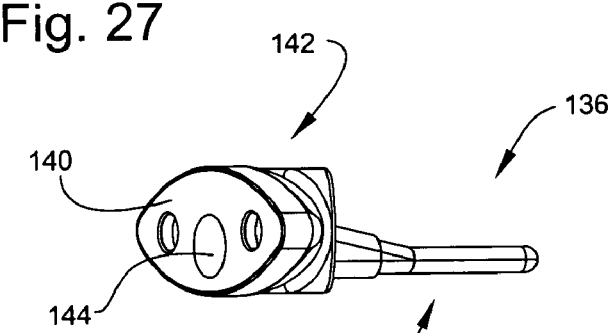
Figure 30:
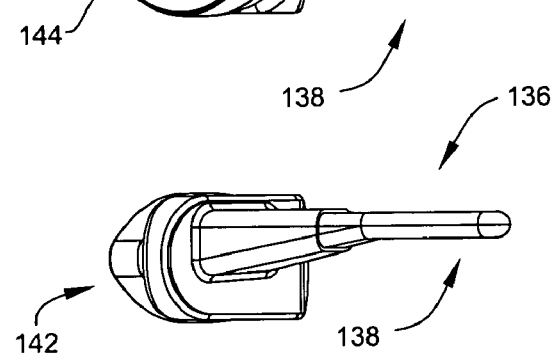

Referring now to FIG. 22, a pre-operative x-ray of a patient suffering from radio-carpal arthritis is shown. FIG. 23 shows the same patient 32 months post-operatively now asymptomatic and with good functional range of motion.

Referring now to FIGS. 24-30, there are shown various views of an alternative embodiment 136 of the prosthetic wrist implant disclosed herein. In particular, the implant includes a radial implant component 138, a carpal component 140 and a bearing component 142. As can be seen in FIGS. 24-30, radial component 138 and bearing component 142 are similar to radial component 40 and bearing component 42 and respectively shown in FIGS. 2A and 2B. However, in this embodiment carpal component 140 does not have a carpal post 50. Similarly, in accordance with another alternative embodiment (not shown), radial implant 136 may be secured using at least one screw that is inserted through the radial component into the radial bone 12.

It will be understood that various details of the present subject matter may be changed without departing from the scope of the subject matter. Furthermore, the foregoing description is for the purpose of illustration only, and not for the purpose of limitation.

What is claimed is:

1. A prosthetic wrist implant comprising:
   (a) a radial component including a base member having an upper bearing surface and a lower surface having an elongated radial stem extending therefrom for fixation to a radius bone;
   (b) a carpal component including a substantially planar base member having an upper surface having an elongated carpal post member for fixation to one or more carpal bones, an outer edge, and a lower surface with at least one socket protrusion extending therefrom;
   (c) an articulating bearing component for placement between the radial and carpal components, the bearing component having an upper surface defining at least one socket recess having a continuous inner circumference and a lower bearing surface for cooperative engagement with the upper bearing surface of the radial component; and
   (d) wherein the socket protrusion of the carpal component is configured for linearly and coaxially engaging the socket recess of the bearing component to minimize rotational and translational movement of the carpal component relative to the bearing component.

2. The prosthetic wrist implant according to claim 1 wherein the elongated radial stem of the radial component is in an off-center position in relation to a center of the lower surface of the radial component.

3. A prosthetic wrist implant comprising:
   (a) a radial component including a base member having an upper bearing surface and a lower surface having an elongated radial stem extending therefrom for fixation to a radius bone;
   (b) a carpal component including a substantially planar base member having an upper surface having an elongated carpal post member for fixation to one or more carpal bones, an outer edge, and a lower surface with at least one socket protrusion extending therefrom;
   (c) an articulating bearing component for placement between the radial and carpal components, the bearing component having an upper surface defining at least one socket recess and a lower bearing surface for cooperative engagement with the upper bearing surface of the radial component;
   wherein the socket protrusion of the carpal component is adapted to linearly engage the socket recess of the bearing component to desirably limit rotational and translational movement of the carpal component relative to the bearing component; and
   wherein the articulating bearing component further comprises a substantially continuous extended skirt of material around the perimeter of and extending from the upper surface of the bearing component, the extended skirt further defining a skirt upper edge furthest away from the upper surface.

4. The prosthetic wrist implant according to claim 3 wherein the skirt at least substantially surrounds the carpal component planar base member outer edge when the socket protrusion of the carpal component is engaged with the socket recess of the bearing component.

5. The prosthetic wrist implant according to claim 4 wherein the skirt upper edge is disposed upon a plane that is substantially coplanar with the carpal component planar base member upper surface.

6. A prosthetic wrist implant comprising:
   (a) a radial component including a base member having an upper bearing surface and a lower surface having an elongated radial stem extending therefrom for fixation to a radius bone;
   (b) a carpal component including a substantially planar base member having an upper surface having an elongated carpal post member for fixation to one or more carpal bones, an outer edge, and a lower surface with at least one socket protrusion extending therefrom;
   (c) an articulating bearing component for placement between the radial and carpal components, the bearing component having an upper surface defining at least one socket recess and a lower bearing surface for cooperative engagement with the upper bearing surface of the radial component;
   wherein the socket protrusion of the carpal component is adapted to linearly engage the socket recess of the bearing component to desirably limit otational and translational movement of the carpal component relative to the bearing component; and
   wherein the upper bearing surface of the radial component is at least substantially concave.

7. The prosthetic wrist implant according to claim 6 wherein the lower bearing surface of the bearing component is at least substantially convex in proportional relationship to the substantially concaved upper bearing surface of the radial component.

8. A prosthetic wrist implant comprising:
   (a) a radial component including a base member having an upper bearing surface and a lower surface having an elongated radial stem extending therefrom for fixation to a radius bone;
   (b) a carpal component including a substantially planar base member having an upper surface having an elongated carpal post member for fixation to one or more carpal bones, an outer edge, and a lower surface with at least one socket protrusion extending therefrom;
   (c) an articulating bearing component for placement between the radial and carpal components, the bearing component having an upper surface defining at least one socket recess and a lower bearing surface for cooperative engagement with the upper bearing surface of the radial component;
   wherein the socket protrusion of the carpal component is adapted to linearly engage the socket recess of the bearing component to desirably limit rotational and translational movement of the carpal component relative to the bearing component; and wherein the socket protrusion of the carpal component is substantially cylindrical and further comprises an external lip that is continuous around the circumference of the socket protrusion.

9. The prosthetic wrist implant according to claim 8 wherein the socket recess of the bearing component is substantially cylindrical and further comprises an internal groove that is continuous around the circumference of the socket recess.

10. The prosthetic wrist implant according to claim 9 wherein the upper surface of the articulating bearing component is attached to the planar base member lower surface of the carpal component by an external lip of the socket protrusion of the carpal component matingly engaging an internal groove of the socket recess of the bearing component.

11. The prosthetic wrist implant according to claim 1 wherein the articulating bearing component is constructed of a plastic material.

12. The prosthetic wrist implant according to claim 1 wherein the lower surface of the radial component has a first substantially flat portion and a second substantially flat portion disposed at an angle with respect to the first flat portion.

13. The prosthetic wrist implant according to claim 1 wherein the elongated radial stem of the radial component is fixated to the radius bone through the use of bone cement.

14. The prosthetic wrist implant according to claim 1 wherein the elongated radial stem of the radial component is fixated to the radius bone through press-fitting.

15. A prosthetic wrist implant comprising:
(a) a radial component including a base member having an upper bearing surface and a lower surface having an elongated radial stem extending therefrom for fixation to a radius bone;
(b) a carpal component including a substantially planar base member having an upper surface having an elongated carpal post member for fixation to one or more carpal bones, an outer edge, and a lower surface with a pair of socket protrusions extending therefrom, wherein each socket protrusion defines an opening therethrough adapted for receiving a screw;
(c) an articulating bearing component for placement between the radial and carpal components, the bearing component having an upper surface defining a pair of socket recesses having continuous inner circumferences, and the bearing component having a lower bearing surface for cooperative engagement with the upper bearing surface of the radial component; and
(d) wherein the pair of socket protrusions of the carpal component is configured for linearly and coaxially engaging the pair of socket recesses of the bearing component to minimize rotational and translational movement of the carpal component relative to the bearing component.

16. The prosthetic wrist implant according to claim 15 wherein the elongated radial stem of the radial component is in an off-center position in relation to a center of the lower surface of the radial component.

17. A prosthetic wrist implant comprising:
(a) a radial component including a base member having an upper bearing surface and a lower surface having an elongated radial stem extending therefrom for fixation to a radius bone;
(b) a carpal component including a substantially planar base member having an upper surface having an elongated carpal post member for fixation to one or more carpal bones, an outer edge, and a lower surface with a pair of socket protrusions extending therefrom, wherein each socket protrusion defines an opening therethrough adapted for receiving a screw;
(c) an articulating bearing component for placement between the radial and carpal components, the bearing component having an upper surface defining a pair of socket recesses, and the bearing component having a lower bearing surface for cooperative engagement with the upper bearing surface of the radial component;
wherein the pair of socket protrusions of the carpal component is adapted to linearly engage the pair of socket recesses of the bearing component to desirably limit rotational and translational movement of the carpal component relative to the bearing component; and
wherein the articulating bearing component further comprises a substantially continuous extended skirt of material around the perimeter of and extending from the upper surface of the bearing component, the extended skirt further defining a skirt upper edge furthest away from the upper surface.

18. The prosthetic wrist implant according to claim 17 wherein the skirt at least substantially surrounds the carpal component planar base member outer edge when the socket protrusion of the carpal component is engaged with the socket recess of the bearing component.

19. The prosthetic wrist implant according to claim 18 wherein the skirt upper edge is disposed upon a plane that is substantially coplanar with the carpal component planar base member upper surface.

20. A prosthetic wrist implant comprising:
(a) a radial component including a base member having an upper bearing surface and a lower surface having an elongated radial stem extending therefrom for fixation to a radius bone;
(b) a carpal component including a substantially planar base member having an upper surface having an elongated carpal post member for fixation to one or more carpal bones, an outer edge, and a lower surface with a pair of socket protrusions extending therefrom, wherein each socket protrusion defines an opening therethrough adapted for receiving a screw;
(c) an articulating bearing component for placement between the radial and carpal components, the bearing component having an upper surface defining a pair of socket recesses, and the bearing component having a lower bearing surface for cooperative engagement with the upper bearing surface of the radial component;
wherein the pair of socket protrusions of the carpal component is adapted to linearly engage the pair of socket recesses of the bearing component to desirably limit rotational and translational movement of the carpal component relative to the bearing component; and
wherein the upper bearing surface of the radial component is at least substantially concave.

21. The prosthetic wrist implant according to claim 20 wherein the lower bearing surface of the bearing component is at least substantially convex in proportional relationship to the substantially concaved upper bearing surface of the radial component.

22. A prosthetic wrist implant comprising:
(a) a radial component including a base member having an upper bearing surface and a lower surface having an elongated radial stem extending therefrom for fixation to a radius bone;
(b) a carpal component including a substantially planar base member having an upper surface having an elongated carpal post member for fixation to one or more carpal bones, an outer edge, and a lower surface with a pair of socket protrusions extending therefrom, wherein each socket protrusion defines an opening therethrough adapted for receiving a screw;

(c) an articulating bearing component for placement between the radial and carpal components, the bearing component having an upper surface defining a pair of socket recesses, and the bearing component having a lower bearing surface for cooperative engagement with the upper bearing surface of the radial component;

wherein the pair of socket protrusions of the carpal component is adapted to linearly engage the pair of socket recesses of the bearing component to desirably limit rotational and translational movement of the carpal component relative to the bearing component; and wherein the socket protrusion of the carpal component is substantially cylindrical and further comprises an external lip that is continuous around the circumference of the socket protrusion.

23. The prosthetic wrist implant according to claim 22 wherein the socket recess of the bearing component is substantially cylindrical and further comprises an internal groove that is continuous around the circumference of the socket recess.

24. The prosthetic wrist implant according to claim 23 wherein the upper surface of the articulating bearing component is attached to the planar base member lower surface of the carpal component by an external lip of the socket protrusion of the carpal component matingly engaging an internal groove of the socket recess of the bearing component.

25. The prosthetic wrist implant according to claim 15 wherein the articulating bearing component is constructed of a plastic material.

26. The prosthetic wrist implant according to claim 15 wherein the lower surface of the radial component has a first substantially flat portion and a second substantially flat portion disposed at an angle with respect to the first flat portion.

27. The prosthetic wrist implant according to claim 15 wherein the elongated radial stem of the radial component is fixated to the radius bone through the use of bone cement.

28. The prosthetic wrist implant according to claim 15 wherein the elongated radial stem of the radial component is fixated to the radius bone through press-fitting.

29. A prosthetic wrist implant for implantation between a patient's radius bone and carpal bone complex comprising:

(a) a radial component including a base member having an upper bearing surface and a lower surface having an elongated radial stem extending therefrom that is implanted into a radius bone;

(b) a carpal component including a substantially planar base member having an upper surface having an elongated carpal post member that is implanted into the capitate bone of the carpal bone complex, a lower surface with a pair of socket protrusions extending therefrom, wherein each socket protrusion defines an opening therethrough adapted for receiving a screw, and further wherein a screw is implanted into the trapezoid bone and another screw is implanted into the hamate bone of the carpal bone complex;

(c) an articulating bearing component for placement between the radial and carpal components, the bearing component having an upper surface defining a pair of socket recesses having continuous inner circumferences, and the bearing component having a lower bearing surface for cooperative engagement with the upper bearing surface of the radial component; and (d) wherein the pair of socket protrusions of the carpal component is configured for linearly and coaxially engaging the pair of socket recesses of the bearing component to minimize rotational and translational movement of the carpal component relative to the bearing component.

30. The prosthetic wrist implant according to claim 29 wherein the elongated radial stem of the radial component is in an off-center position in relation to a center of the lower surface of the radial component.

31. A prosthetic wrist implant system comprising:

(a) a plurality of different sized radial components, each radial component including a base member having an upper bearing surface and a lower surface having an elongated radial stem extending therefrom for fixation to a radius bone;

(b) a plurality of different sized carpal components, each carpal component including a substantially planar base member having an upper surface having an elongated carpal post member for fixation to one or more carpal bones and a lower surface with at least one socket protrusion extending therefrom;

(c) a plurality of different sized articulating bearing components for placement between correspondingly sized radial and carpal components, each bearing component having an upper surface defining at least one socket recess having a continuous inner circumference and a lower bearing surface for cooperative engagement with the upper bearing surface of a correspondingly sized radial component; and (d) wherein the socket protrusion of the selected carpal component is configured for linearly and coaxially engaging the socket recess of a correspondingly sized bearing component to minimize rotational and translational movement of the carpal component relative to the bearing component.

32. The prosthetic wrist implant system according to claim 31 wherein the elongated radial stem of the radial component is in an off-center position in relation to a center of the lower surface of the radial component.

* * * * *